US011480568B2

(12) United States Patent
Sorek et al.

(10) Patent No.: US 11,480,568 B2
(45) Date of Patent: Oct. 25, 2022

(54) DIAGNOSIS OF AUTOIMMUNE DISEASES

(71) Applicant: YEDA RESEARCH AND DEVELOPMENT CO. LTD., Rehovot (IL)

(72) Inventors: Rachel Sorek, Moshav Tzafaria (IL); Keren Jakobi-Brook, Tel Aviv (IL); Pennina Safer, Rehovot (IL); Irun R. Cohen, Rehovot (IL)

(73) Assignee: YEDA RESEARCH AND DEVELOPMENT CO. LTD., Rehovot (IL)

( * ) Notice: Subject to any disclaimer, the term of this patent is extended or adjusted under 35 U.S.C. 154(b) by 499 days.

(21) Appl. No.: 16/133,295

(22) Filed: Sep. 17, 2018

(65) Prior Publication Data

US 2019/0094219 A1 Mar. 28, 2019

Related U.S. Application Data

(60) Provisional application No. 62/564,344, filed on Sep. 28, 2017.

(51) Int. Cl.
*G01N 33/564* (2006.01)
*G01N 33/577* (2006.01)

(52) U.S. Cl.
CPC ......... *G01N 33/564* (2013.01); *G01N 33/577* (2013.01); *G01N 2800/102* (2013.01); *G01N 2800/104* (2013.01); *G01N 2800/50* (2013.01); *G01N 2800/52* (2013.01); *G01N 2800/54* (2013.01); *G01N 2800/7095* (2013.01)

(58) Field of Classification Search
CPC ........... G01N 33/577; G01N 2800/102; G01N 2800/104; G01N 2800/50; G01N 2800/52; G01N 2800/54
See application file for complete search history.

(56) References Cited

U.S. PATENT DOCUMENTS

| | | | | |
|---|---|---|---|---|
| 6,468,537 | B1 * | 10/2002 | Datta | A61K 38/1709 514/21.4 |
| 11,047,855 | B2 * | 6/2021 | Sorek | G01N 33/564 |
| 2002/0028830 | A1 * | 3/2002 | Deluca | A61K 33/06 514/310 |
| 2004/0191756 | A1 * | 9/2004 | Matthias | A61K 38/1709 435/6.16 |
| 2007/0196835 | A1 * | 8/2007 | Bankaitis-Davis | C12Q 1/6883 435/6.16 |
| 2009/0304686 | A1 * | 12/2009 | Meyaard | C07K 16/2803 435/375 |
| 2010/0261613 | A1 * | 10/2010 | Centola | G16B 40/30 506/8 |
| 2011/0281756 | A1 * | 11/2011 | Wu | C12N 15/111 435/6.12 |
| 2012/0129853 | A1 * | 5/2012 | Elmore | A61K 31/496 514/234.5 |
| 2014/0065634 | A1 * | 3/2014 | Walker | C07K 16/18 435/6.19 |
| 2017/0074875 | A1 | 3/2017 | Lüking | |
| 2019/0079083 | A1 * | 3/2019 | Harwanegg | G01N 33/68 |

FOREIGN PATENT DOCUMENTS

| | | |
|---|---|---|
| WO | 2011099012 A1 | 8/2011 |
| WO | 2014091490 A2 | 6/2014 |
| WO | 2015101987 A1 | 7/2015 |
| WO | 2015101988 A1 | 7/2015 |

OTHER PUBLICATIONS

Hu et al. (Medical Science Monitor 2015 vol. 21, p. 3690-3695). (Year: 2015).*
Schett et al. (Lupus 2002 vol. 11, p. 704-715). (Year: 2002).*
Ching et al. (J. Dent. Res. 2011 vol. 90, p. 445-449). (Year: 2011).*
Ingegnoli (Clin. Exp. Rheumatology 2004 22:499-501 (Year: 2004).*
Mullazehi (Arthritis Res & Therapy 2012 14:R100 total 7 pages) (Year: 2012).*
Stemmer (Cli. Immunology & Immunopathology 1995 76:82-89) (Year: 1995).*
Reed (Arthritis & Rheumatism 2008 58:1125-1129) (Year: 2008).*
Budde Lupus 2016 25: 812-822 (Year: 2016).*
Schett Rheumatology 2001 40:424-431 (Year: 2001).*
Katsumata Molecular & Cellular Proteomics 2011 10: 1-12 (Year: 2011).*
Budde (II) Scientific Abstracts Jun. 12, 2015, p. 633 (Year: 2015).*
Fattal et al., (2015) Guanine polynucleotides are self-antigens for human natural autoantibodies and are significantly reduced in the human genome. Immunology 146(3): 401-410.
Hu et al., (2011) Identification of autoantibody biomarkers for primary Sjögren's syndrome using protein microarrays Proteomics 11(8): 1499-1507.
Hueber et al., (2005) Antigen microarray profiling of autoantibodies in rheumatoid arthritis. Arthritis Rheum 52(9): 2645-2655.
Putterman et al., (2016) SLE-key(®) rule-out serologic test for excluding the diagnosis of systemic lupus erythematosus: Developing the ImmunArray iCHIP(®).J Immunol Methods 429: 1-6.
Szodoray and Alex (2011) Protein array diagnostics for guiding therapy in rheumatoid arthritis. Mol Diagn Ther 15(5): 247-254.

* cited by examiner

*Primary Examiner* — Changhwa J Cheu
(74) *Attorney, Agent, or Firm* — J.A. Lindeman & Co. PLLC

(57) ABSTRACT

Assays and methods for diagnosing and treating autoimmune diseases. Particularly, the invention provides methods for differential diagnosis of specific autoimmune diseases, including autoimmune rheumatic disorders.

9 Claims, 8 Drawing Sheets

Specification includes a Sequence Listing.

Table 15

| Antigen | Isotype | HC vs OAD | HC vs SLE | HC vs SSC | HC vs APS | HC vs SS | HC vs RA | SLE vs SSC | SLE vs APS | SLE vs SS | SLE vs RA | SSC vs SS | APS vs SS | SS vs RA |
|---|---|---|---|---|---|---|---|---|---|---|---|---|---|---|
| AITRL | IgG | | | | | 2.4E-06 | | | | 5.8E-02 | | 8.8E-09 | 1.9E-04 | 1.9E-13 |
| APEX1 | IgG | 3.4E-04 | 1.9E-27 | 4.6E-02 | 9.7E-01 | 2.5E-08 | 3.8E-01 | 2.3E-12 | 1.7E-05 | 5.9E-03 | 3.3E-10 | 5.8E-05 | 4.2E-02 | 8.4E-04 |
| ATF2 | IgG | 8.6E-05 | 4.7E-03 | 4.6E-09 | 3.6E-03 | 4.3E-01 | 1.3E-11 | 6.4E-06 | 1.2E-02 | 4.8E-01 | 4.0E-07 | 3.8E-03 | 1.5E-01 | 3.1E-04 |
| B2GP1 | IgG | 1.6E-03 | 4.5E-02 | 1.7E-07 | 3.7E-01 | 1.6E-01 | 3.9E-08 | 1.8E-03 | 1.1E-01 | 9.7E-01 | 1.6E-06 | 3.3E-02 | 2.0E-01 | 4.7E-05 |
| B7-2 | IgM | 1.7E-03 | 1.6E-07 | 4.3E-03 | 3.1E-02 | | | 2.0E-01 | 5.1E-01 | 1.8E-02 | 2.2E-03 | 1.7E-01 | 3.5E-01 | |
| B7H4 | IgG | | 2.7E-10 | | | 1.2E-01 | | 1.5E-08 | 6.9E-06 | 1.5E-01 | 8.5E-12 | 6.7E-03 | 8.1E-02 | 1.5E-04 |
| BCMO1p6-206 | IgG | 2.0E-05 | 8.1E-01 | 9.0E-06 | 4.1E-07 | 6.9E-01 | 4.6E-06 | 6.3E-03 | 1.5E-04 | 9.1E-01 | 2.4E-03 | 6.2E-02 | 1.2E-02 | 3.9E-02 |
| BCOADC-E2 | IgG | | 4.1E-09 | | | | | 1.3E-05 | 4.4E-04 | 1.7E-01 | 4.8E-08 | | | |
| BDNF | IgG | | 6.0E-08 | | | 2.4E-02 | | 4.5E-07 | 4.6E-04 | 3.7E-01 | 3.5E-11 | 1.1E-03 | 2.0E-02 | 1.3E-07 |
| BDNF | IgM | 1.2E-02 | 1.4E-07 | 8.6E-01 | 1.1E-01 | 1.6E-01 | 7.2E-01 | 3.6E-04 | 2.1E-01 | 2.7E-01 | 1.3E-03 | 4.4E-01 | 9.9E-01 | 4.3E-01 |
| BMP7 | IgM | 4.7E-08 | 1.3E-07 | 3.1E-02 | 1.3E-06 | 3.4E-02 | 2.5E-03 | 5.7E-02 | 6.5E-01 | 3.4E-01 | 2.2E-01 | 8.3E-01 | 1.5E-01 | 9.5E-01 |
| BPI | IgG | 8.6E-11 | 9.1E-01 | 2.3E-16 | 1.2E-07 | 9.0E-02 | 1.5E-25 | 2.9E-05 | 1.1E-02 | 4.4E-01 | 2.8E-08 | 3.5E-04 | 3.1E-02 | 5.1E-06 |
| BST2 | IgG | | 2.1E-07 | | | 1.0E-03 | | 6.0E-06 | 1.9E-06 | 9.5E-01 | 1.6E-07 | 3.3E-03 | 2.3E-03 | 4.3E-04 |
| C1q | IgG | 1.6E-19 | 1.4E-39 | 6.4E-08 | 8.1E-05 | 1.2E-03 | 3.0E-09 | 4.9E-12 | 5.8E-06 | 9.4E-06 | 6.8E-09 | 8.7E-01 | 8.4E-01 | 5.4E-01 |
| C1s | IgG | 5.8E-09 | 9.9E-08 | 5.8E-06 | 2.2E-03 | 1.5E-01 | 1.5E-06 | 4.4E-01 | 5.1E-01 | 5.0E-01 | 8.4E-01 | 7.0E-01 | 8.9E-01 | 5.7E-01 |
| C2 | IgG | | 7.6E-20 | | | 1.2E-07 | | 6.1E-14 | 5.8E-06 | 1.2E-01 | 9.8E-16 | 1.8E-07 | 3.7E-03 | 6.8E-10 |
| C3b | IgG | | 2.7E-19 | | | | | 3.1E-12 | 3.3E-06 | 5.5E-01 | 1.7E-08 | | | |
| C3c | IgG | 7.3E-03 | 6.6E-20 | 1.1E-01 | 2.3E-01 | 2.9E-01 | 4.3E-01 | 1.0E-06 | 5.9E-04 | 7.4E-03 | 4.8E-05 | 4.2E-01 | 8.5E-02 | 9.2E-01 |
| CA125 | IgG | 5.8E-08 | 9.9E-05 | 6.2E-12 | 4.2E-05 | 8.7E-01 | 4.6E-11 | 7.8E-03 | 3.0E-01 | 9.4E-02 | 2.4E-02 | 2.7E-02 | 2.7E-01 | 2.9E-02 |
| CD137L | IgG | | | | | 3.2E-07 | | | | 6.3E-04 | | 2.2E-06 | 6.5E-03 | 5.4E-05 |
| CD137 | IgM | 3.6E-08 | 2.7E-01 | 7.4E-05 | 2.4E-06 | 1.4E-06 | 3.2E-09 | 2.5E-01 | 9.9E-01 | 1.3E-01 | 2.5E-02 | 3.6E-01 | | |
| CD29 | IgG | 4.6E-05 | 3.0E-01 | 1.2E-07 | 9.7E-03 | 2.0E-03 | 1.3E-15 | 5.7E-04 | 9.2E-02 | 1.9E-01 | 4.7E-07 | 2.7E-04 | 4.6E-02 | 1.4E-06 |
| CD31 | IgG | 1.3E-01 | 6.8E-05 | 1.2E-07 | 9.3E-02 | 1.0E-02 | 1.6E-02 | 2.4E-06 | 3.5E-03 | 8.0E-01 | 1.7E-03 | 3.7E-04 | 3.2E-03 | 2.8E-02 |
| CD3E | IgG | 1.2E-02 | 3.7E-20 | 5.8E-02 | 9.1E-01 | 5.7E-01 | 2.2E-02 | 1.0E-04 | 2.9E-04 | 2.1E-03 | 7.9E-07 | 8.1E-01 | 8.9E-01 | 4.1E-01 |
| CD46 | IgG | 1.2E-03 | 6.9E-19 | 3.3E-01 | 9.8E-01 | 1.5E-01 | 9.7E-01 | 5.9E-05 | 1.6E-04 | 3.8E-02 | 1.9E-06 | 8.1E-01 | 7.3E-01 | 5.8E-01 |
| CD62P | IgG | 4.4E-17 | 2.6E-32 | 2.1E-06 | 1.4E-03 | 1.5E-06 | 6.6E-06 | 1.7E-10 | 9.4E-05 | 6.5E-03 | 3.4E-08 | 1.7E-01 | 5.5E-01 | 3.4E-01 |
| CD62P | IgM | 9.6E-08 | 1.3E-05 | 5.2E-03 | 1.7E-06 | 2.7E-02 | 6.5E-03 | 3.2E-01 | 5.1E-01 | 6.3E-01 | 3.2E-01 | 9.4E-01 | 2.4E-01 | 9.3E-01 |
| CD80 | IgM | 7.9E-03 | 2.2E-07 | 5.0E-02 | 9.4E-02 | 5.3E-01 | 5.6E-01 | 1.3E-01 | 4.6E-01 | 6.9E-02 | 1.8E-02 | 4.2E-01 | 5.7E-01 | 7.0E-01 |
| CD8A | IgG | 9.7E-06 | 8.6E-01 | 1.6E-08 | 1.2E-03 | 7.1E-01 | 8.0E-06 | 2.0E-03 | 6.9E-02 | 7.8E-01 | 1.1E-02 | 1.6E-02 | 1.6E-01 | 4.4E-02 | continued

| Antigen | Isotype | HC vs OAD | HC vs SLE | HC vs SSC | HC vs APS | HC vs SS | HC vs RA | SLE vs SSC | SLE vs APS | SLE vs SS | SLE vs RA | SSC vs SS | APS vs SS | SS vs RA |
|---|---|---|---|---|---|---|---|---|---|---|---|---|---|---|
| CRYAB | IgG | 5.1E-05 | 4.8E-01 | 4.1E-11 | 4.1E-06 | 8.4E-08 | 1.9E-12 | 1.1E-06 | 1.2E-04 | 1.7E-03 | 6.7E-09 | 9.7E-09 | 4.9E-05 | 7.7E-10 |
| CTLA4 | IgM | 4.2E-07 | 1.2E-08 | 1.6E-02 | 2.6E-02 | 2.3E-03 | 5.0E-05 | 6.3E-02 | 4.5E-01 | 3.7E-01 | | 6.0E-01 | 9.0E-01 | |
| CX3CL1 | IgG | | 1.8E-04 | | | 1.6E-05 | | 5.2E-06 | 6.1E-03 | 6.1E-03 | 5.5E-08 | 2.6E-06 | 2.0E-03 | 2.4E-08 |
| CXCL2 | IgG | | | | | 1.2E-08 | | | | 2.4E-05 | | 1.1E-11 | 4.9E-05 | 3.0E-13 |
| Catalase | IgG | 3.8E-05 | 9.4E-01 | 5.1E-07 | 7.1E-02 | 3.9E-02 | 1.3E-02 | 1.0E-03 | 2.6E-01 | 2.1E-01 | 1.0E-01 | 3.8E-01 | 9.5E-01 | 9.1E-01 |
| Chromatin | IgG | 6.6E-15 | 1.2E-42 | 1.9E-03 | 2.6E-04 | 1.0E-14 | 3.4E-02 | 9.9E-13 | 2.1E-06 | 8.8E-04 | 6.7E-13 | 1.7E-03 | 5.5E-02 | 9.7E-05 |
| Chromatin | IgM | 1.6E-12 | 2.2E-26 | 2.8E-02 | 1.7E-08 | 3.4E-04 | 5.4E-04 | 3.6E-08 | 6.0E-02 | 1.1E-02 | 1.8E-06 | 3.0E-01 | 5.1E-01 | 6.2E-01 |
| CollagenII | IgG | 5.0E-22 | 2.5E-12 | 1.1E-09 | 4.4E-04 | 6.3E-03 | 4.9E-13 | 3.2E-01 | 1.3E-01 | 1.4E-01 | 8.9E-01 | 4.2E-01 | 8.2E-01 | 4.7E-02 |
| CollagenX | IgG | 7.5E-03 | 5.8E-01 | 1.6E-06 | 2.5E-02 | 2.2E-12 | 5.2E-14 | 4.6E-04 | 2.8E-02 | 7.2E-06 | 1.1E-14 | 4.1E-09 | 1.3E-05 | 1.0E-17 |
| DLST | IgG | | 2.7E-20 | | | | | 7.4E-11 | 3.4E-05 | 5.2E-05 | 2.7E-15 | | | |
| DNAds | IgM | 1.9E-08 | 4.7E-14 | 3.8E-02 | 1.6E-06 | 4.9E-01 | 9.6E-04 | 3.5E-04 | 5.5E-01 | 1.3E-02 | 6.8E-03 | 7.8E-01 | 5.5E-02 | 4.1E-01 |
| DNAds | IgG | 2.3E-13 | 2.1E-34 | 1.8E-03 | 1.9E-03 | 2.7E-02 | 1.8E-05 | 2.3E-12 | 1.5E-05 | 3.8E-05 | 9.6E-09 | 9.1E-01 | 7.9E-01 | 6.8E-01 |
| DNAss | IgM | 6.9E-08 | 1.7E-06 | 2.8E-02 | 3.9E-06 | 4.2E-02 | 1.2E-03 | 1.1E-01 | 6.2E-01 | 4.6E-01 | 3.7E-01 | 8.5E-01 | 2.0E-01 | 9.0E-01 |
| DNAss | IgG | 6.4E-14 | 7.1E-27 | 1.5E-02 | 3.0E-02 | 1.5E-04 | 1.5E-06 | 6.7E-11 | 2.3E-04 | 1.0E-03 | 4.6E-07 | 1.0E-01 | 6.8E-01 | 9.0E-01 |
| DT | IgG | 4.7E-13 | 9.1E-03 | 4.2E-10 | 4.6E-04 | 6.3E-05 | 8.0E-14 | 2.3E-02 | 3.1E-01 | 2.4E-01 | 1.1E-03 | 7.8E-01 | 9.1E-01 | 3.8E-01 |
| EPO | IgM | 1.0E-07 | 4.6E-05 | 1.3E-02 | 4.1E-02 | 2.2E-02 | 8.8E-07 | 3.7E-01 | 6.7E-01 | 7.4E-01 | 4.5E-01 | 8.5E-01 | 9.8E-01 | 4.6E-01 |
| ESD | IgG | 9.6E-08 | 8.6E-01 | 1.0E-07 | 2.8E-06 | 6.5E-01 | 8.3E-13 | 7.9E-04 | 2.0E-03 | 8.5E-01 | 4.5E-06 | 6.0E-03 | 1.1E-02 | 1.5E-04 |
| EndostatinP1 | IgG | | | | | 1.1E-15 | | | | 1.3E-04 | | 3.7E-18 | 3.8E-05 | 7.0E-19 |
| EndostatinP1 | IgM | 6.5E-01 | 4.9E-01 | 2.3E-02 | 9.0E-01 | 1.9E-12 | 1.5E-03 | | 7.8E-01 | 1.3E-04 | | 3.4E-09 | 3.7E-03 | 1.6E-08 |
| Entactin | IgG | 6.3E-04 | 3.4E-01 | 6.0E-03 | 2.2E-03 | 8.9E-01 | 2.5E-07 | 1.2E-02 | 6.1E-03 | 5.2E-01 | 1.9E-04 | 3.4E-01 | 2.2E-01 | 4.0E-02 |
| FABP1 | IgG | | 5.6E-03 | | | | | 8.0E-07 | 7.2E-03 | 1.4E-01 | 6.3E-07 | | | |
| FASLG | IgG | | | | | 2.0E-04 | | 5.5E-15 | 9.4E-05 | 1.1E-01 | 4.2E-17 | 1.2E-12 | 3.1E-04 | 5.8E-14 |
| FGFb | IgG | | 1.7E-02 | | | 2.4E-06 | | | | 9.4E-03 | | 1.1E-11 | 2.0E-03 | 2.3E-13 |
| FPR1 | IgG | 9.4E-10 | 8.3E-01 | 3.3E-10 | 6.2E-03 | 2.2E-01 | 5.4E-18 | 3.2E-04 | 1.1E-01 | 5.3E-01 | 1.4E-07 | | | |
| FSCN1 | IgM | 9.2E-08 | 4.0E-03 | 3.7E-03 | 2.7E-01 | 4.2E-03 | 1.9E-05 | 7.5E-01 | 6.0E-01 | 7.5E-01 | 4.4E-01 | 4.2E-01 | 3.9E-01 | 9.1E-01 |
| FactorII | IgG | | 4.5E-03 | | | 1.3E-02 | | 1.4E-11 | 5.8E-06 | 8.2E-01 | 8.0E-18 | 2.7E-08 | 1.7E-04 | 7.4E-15 |
| FactorP | IgG | | 2.0E-19 | | | | | 9.4E-09 | 7.1E-05 | 1.1E-02 | 4.4E-08 | | | |
| Ferritin | IgG | 3.4E-09 | 1.7E-01 | 1.1E-09 | 2.9E-09 | 6.8E-01 | 3.1E-17 | 2.6E-06 | 1.0E-06 | 6.6E-01 | 8.5E-11 | 2.7E-03 | 9.5E-04 | 4.9E-06 |
| GBE1 | IgG | | 1.7E-01 | | | | | 1.2E-07 | 1.2E-04 | 3.6E-01 | 6.8E-11 | | | |
| GCSF | IgG | | | | | 6.5E-03 | | | | 5.8E-01 | | 3.1E-07 | 1.9E-04 | 6.4E-11 | continued

| Antigen | Isotype | HC vs OAD | HC vs SLE | HC vs SSC | HC vs APS | HC vs SS | HC vs RA | SLE vs SSC | SLE vs APS | SLE vs SS | SLE vs RA | SSC vs SS | APS vs SS | SS vs RA |
|---|---|---|---|---|---|---|---|---|---|---|---|---|---|---|
| GSTP1 | IgG | 1.5E-05 | 9.5E-01 | 5.4E-05 | 5.6E-02 | 9.3E-01 | 5.9E-12 | 1.9E-02 | 2.4E-01 | 9.7E-01 | 5.9E-06 | 1.1E-01 | 4.5E-01 | 6.9E-04 |
| Glypican6 | IgG | | | | | 7.3E-06 | | | | 1.7E-03 | | 1.1E-06 | 2.5E-02 | 3.7E-09 |
| H1 | IgG | 4.3E-02 | 4.3E-39 | 8.1E-05 | 9.9E-01 | 5.7E-24 | 3.9E-06 | 1.1E-12 | 4.8E-05 | 2.1E-01 | 6.1E-12 | 5.5E-07 | 1.1E-02 | 4.2E-07 |
| H1 | IgM | 6.6E-12 | 3.4E-12 | 4.1E-03 | 1.1E-08 | 9.3E-04 | 2.0E-04 | 9.3E-03 | 8.9E-01 | 3.0E-01 | 4.4E-02 | 6.0E-01 | 2.1E-01 | 8.6E-01 |
| H2BQ | IgG | 2.5E-03 | 8.1E-08 | 1.4E-08 | 4.6E-04 | 6.7E-01 | 4.0E-13 | 3.5E-06 | 1.1E-03 | 2.3E-01 | 2.8E-07 | 5.3E-02 | 3.0E-01 | 9.9E-03 |
| H2BQ | IgM | 1.2E-01 | 1.1E-07 | 4.3E-01 | 9.4E-01 | 1.9E-01 | 3.5E-01 | 1.2E-04 | 7.9E-02 | 1.8E-01 | 5.0E-04 | 1.4E-01 | 7.4E-01 | 1.7E-01 |
| H2B | IgG | | 3.7E-11 | | | 4.7E-08 | | 7.2E-16 | 1.0E-06 | 7.2E-01 | 1.5E-21 | 1.4E-11 | 5.5E-05 | 2.4E-17 |
| H2B | IgM | 1.8E-03 | 1.5E-08 | 2.8E-01 | 7.8E-04 | 3.3E-05 | 9.7E-01 | 3.5E-05 | 6.5E-01 | 8.4E-01 | 1.4E-03 | 5.0E-04 | 8.8E-01 | 8.2E-03 |
| H2a | IgG | | 9.1E-35 | | | 3.3E-24 | | 2.7E-15 | 3.5E-06 | 8.6E-01 | 8.9E-14 | 2.8E-11 | 1.3E-04 | 2.2E-10 |
| H2a | IgM | 2.0E-15 | 2.4E-14 | 2.2E-03 | 2.9E-09 | 7.2E-13 | 4.7E-06 | 3.7E-03 | 9.8E-01 | 8.1E-01 | 3.5E-02 | 2.7E-03 | 8.4E-01 | 8.9E-03 |
| H3 | IgG | 3.9E-08 | 7.4E-01 | 1.1E-10 | 8.3E-06 | 2.1E-01 | 1.5E-15 | 2.4E-04 | 7.5E-03 | 6.1E-01 | 1.9E-06 | 1.1E-03 | 7.0E-03 | 1.4E-05 |
| H4 | IgG | | 1.5E-11 | | | 2.1E-10 | | 1.4E-13 | 1.5E-06 | 3.0E-01 | 6.8E-21 | 4.1E-11 | 1.3E-05 | 7.0E-19 |
| H4 | IgM | 7.0E-04 | 1.5E-09 | 8.1E-01 | 4.0E-05 | 1.1E-03 | 6.4E-01 | 8.3E-05 | 7.4E-01 | 5.1E-01 | 4.3E-04 | 1.9E-02 | 8.1E-01 | 3.7E-02 |
| HLAB | IgG | 5.0E-08 | 1.4E-02 | 1.7E-07 | 7.3E-05 | 7.9E-01 | 7.8E-10 | 8.1E-02 | 1.3E-01 | 2.9E-01 | 1.7E-02 | 1.0E-01 | 1.2E-02 | 1.7E-02 |
| HLAC | IgG | 1.6E-08 | 6.9E-01 | 4.5E-13 | 1.2E-07 | 3.7E-01 | 4.2E-14 | 4.7E-04 | 2.1E-02 | 6.6E-01 | 3.1E-04 | 2.5E-02 | 1.3E-01 | 1.6E-02 |
| HNRNPA1 | IgG | | 3.9E-05 | | | 7.5E-02 | | 3.9E-09 | 1.8E-05 | 4.0E-01 | 2.5E-15 | 4.1E-05 | 2.2E-03 | 6.2E-11 |
| HSP90 | IgG | | 1.2E-03 | | | 3.7E-01 | | 1.3E-08 | 3.4E-04 | 3.7E-01 | 2.8E-07 | 1.1E-03 | 7.8E-02 | 4.2E-03 |
| Haptoglobin2-2 | IgG | 2.7E-04 | 2.2E-03 | 3.7E-07 | 3.6E-02 | 4.9E-03 | 3.8E-06 | 7.9E-02 | 7.5E-01 | 2.2E-02 | 1.8E-01 | 6.2E-02 | 4.3E-01 | 5.1E-02 |
| Histone3SCalf | IgG | 1.2E-03 | 1.5E-26 | | | 2.8E-19 | | 2.3E-13 | 3.8E-04 | 8.7E-01 | 4.9E-11 | 1.1E-10 | 3.2E-03 | 2.2E-09 |
| Histone3SCalf | IgM | 6.2E-15 | 9.1E-11 | 3.2E-04 | 1.1E-08 | 3.6E-10 | 2.7E-07 | 6.3E-02 | 7.0E-01 | 7.5E-01 | 3.3E-01 | 3.5E-02 | 9.8E-01 | 1.4E-01 |
| IFNa2 | IgG | | 1.6E-07 | | 2.6E-02 | 3.1E-04 | | 1.3E-02 | 5.2E-01 | 8.0E-01 | 3.4E-03 | 9.8E-02 | 7.9E-01 | 2.4E-02 |
| IL35 | IgG | | 1.4E-02 | | | 1.6E-02 | | 9.8E-07 | 4.8E-02 | 7.6E-01 | 2.2E-09 | 1.3E-04 | 1.4E-01 | 3.5E-06 |
| IL35 | IgM | 6.4E-08 | 1.4E-05 | 1.3E-05 | 8.6E-06 | 6.0E-02 | 2.0E-06 | | | 6.9E-01 | | 7.4E-01 | 5.5E-01 | 6.6E-01 |
| IL3 | IgG | | | | | 3.8E-13 | | | | 1.0E-03 | | 9.3E-13 | 2.3E-06 | 1.4E-14 |
| IL4 | IgG | 2.4E-14 | 3.4E-09 | 3.1E-08 | 3.0E-05 | 4.7E-01 | 1.5E-06 | 2.3E-01 | 9.0E-01 | 3.8E-02 | 3.2E-01 | 7.1E-03 | 7.4E-02 | 2.8E-02 |
| IL4 | IgM | 8.0E-05 | 4.9E-07 | 6.0E-02 | 4.3E-03 | 3.1E-02 | 1.5E-01 | 4.3E-02 | | 4.8E-01 | 4.3E-02 | 7.0E-01 | 8.4E-01 | 6.0E-01 |
| Integrin | IgG | 4.6E-04 | 2.1E-02 | 9.2E-09 | 1.5E-03 | 9.2E-05 | 7.8E-04 | 2.8E-02 | 5.7E-01 | 1.8E-02 | 3.5E-01 | 1.5E-02 | 2.2E-02 | 8.1E-02 |
| JO-1 | IgG | | 6.2E-03 | | | 3.4E-01 | | 4.0E-05 | 3.0E-05 | 1.5E-01 | 7.6E-13 | | | |
| Ki67 | IgG | 2.6E-04 | 8.1E-01 | 8.5E-08 | 1.9E-02 | 3.4E-01 | 9.1E-06 | 8.3E-03 | 2.8E-01 | 7.9E-01 | 2.2E-02 | 3.0E-02 | 2.7E-01 | 3.6E-02 | continued

| Antigen | Isotype | HC vs OAD | HC vs SLE | HC vs SSC | HC vs APS | HC vs SS | HC vs RA | SLE vs SSC | SLE vs APS | SLE vs SS | SLE vs RA | SSC vs SS | APS vs SS | SS vs RA |
|---|---|---|---|---|---|---|---|---|---|---|---|---|---|---|
| LAG3 | IgG | 8.4E-03 | 1.4E-01 | 7.6E-06 | 5.6E-01 | 1.5E-03 | 8.5E-11 | 1.4E-02 | 8.6E-01 | 4.5E-01 | 1.2E-04 | 3.0E-02 | 4.7E-01 | 4.3E-01 |
| LAIR1 | IgG | 2.8E-63 | 2.3E-33 | 3.4E-39 | 2.8E-25 | 2.9E-19 | 3.6E-51 | 2.9E-01 | 4.0E-01 | 2.3E-01 | 8.8E-01 | 3.9E-01 | 6.8E-01 | 3.5E-03 |
| LFA1 | IgG | | | | | 8.1E-06 | | | | 1.7E-03 | | 2.2E-14 | 1.5E-04 | 3.7E-20 |
| LIGHT | IgG | 1.6E-01 | 8.0E-15 | 3.5E-04 | 3.4E-01 | 2.0E-02 | 2.5E-13 | 8.5E-07 | 5.4E-04 | 1.6E-01 | 9.2E-09 | 3.3E-02 | 3.0E-01 | 1.0E-03 |
| LMNB1 | IgG | | 1.9E-01 | | 6.8E-01 | | | 4.1E-07 | 9.1E-01 | 4.7E-01 | 1.5E-05 | | 9.2E-01 | |
| La | IgG | 8.5E-01 | 3.8E-01 | 5.1E-01 | 1.4E-01 | 1.1E-08 | 4.8E-02 | 3.2E-01 | 3.0E-01 | 4.6E-03 | 1.2E-01 | 9.5E-05 | 1.5E-02 | 5.0E-04 |
| Laminin | IgG | | 1.0E-22 | | | 3.1E-02 | | 1.7E-10 | 3.4E-05 | 8.2E-03 | 1.1E-09 | 1.6E-02 | 3.4E-01 | 1.7E-02 |
| LeptintA | IgG | 1.1E-11 | 1.8E-03 | 6.3E-16 | 1.6E-06 | 2.4E-01 | 5.0E-21 | 5.5E-04 | 9.5E-02 | 5.4E-01 | 2.0E-05 | 1.2E-02 | 2.7E-01 | 1.7E-03 |
| MASP2 | IgG | 4.0E-06 | 7.2E-01 | 5.2E-09 | 1.8E-03 | 2.8E-01 | 9.5E-11 | 1.3E-03 | 1.5E-01 | 5.8E-01 | 5.9E-04 | 1.7E-01 | 6.2E-01 | 8.4E-02 |
| MICA | IgM | 6.1E-08 | 2.2E-08 | 6.7E-03 | 6.3E-04 | 1.2E-03 | 2.1E-03 | 4.7E-02 | 9.9E-01 | 7.3E-01 | 1.8E-01 | 4.8E-01 | 9.0E-01 | 7.1E-01 |
| MIP1b | IgG | | | | | 3.9E-12 | | | | 1.3E-02 | | 4.5E-17 | 2.6E-04 | 5.8E-22 |
| MX1 | IgG | 1.4E-07 | 6.4E-01 | 2.2E-08 | 6.6E-03 | 5.1E-01 | 2.2E-14 | 4.9E-03 | 2.2E-01 | 5.5E-01 | 1.8E-05 | 6.5E-03 | 1.5E-01 | 8.0E-05 |
| MYH1 | IgG | 4.7E-08 | 6.5E-01 | 4.0E-10 | 2.0E-08 | 4.1E-01 | 6.0E-12 | 1.7E-04 | 1.7E-04 | 7.2E-01 | 6.5E-06 | 3.8E-03 | 3.5E-03 | 3.5E-04 |
| Mi-2 | IgG | 4.1E-03 | 3.8E-04 | 2.3E-05 | 3.4E-04 | 7.5E-01 | 9.5E-07 | 6.7E-05 | 1.8E-03 | 2.0E-01 | 6.1E-05 | 7.1E-02 | 1.3E-01 | 4.1E-02 |
| Microglobulin-b2 | IgG | | | | | 2.8E-02 | | | | 6.1E-02 | | 2.0E-05 | 3.7E-02 | 1.4E-08 |
| MitoAg | IgG | 4.4E-03 | 6.3E-10 | 1.9E-01 | 1.4E-01 | 3.2E-01 | 6.1E-01 | 2.3E-02 | 2.7E-01 | 4.8E-02 | 2.5E-05 | 9.9E-01 | 9.0E-01 | 4.2E-01 |
| NFkB | IgG | 6.4E-01 | 8.7E-07 | 6.8E-02 | 7.1E-01 | 9.8E-04 | 2.4E-01 | 2.3E-02 | 1.1E-01 | 9.5E-01 | 1.1E-02 | 1.7E-01 | 3.8E-01 | 1.2E-01 |
| NGAL | IgM | 3.7E-06 | 2.3E-01 | 5.0E-04 | 9.0E-01 | 1.3E-04 | 4.4E-07 | 3.2E-01 | 6.7E-01 | 2.1E-01 | 3.9E-02 | 3.6E-01 | 6.4E-02 | |
| NOR90 | IgG | | 1.2E-04 | | | 1.5E-01 | | 1.7E-07 | 3.3E-02 | 3.6E-01 | 8.2E-12 | 4.3E-03 | 4.9E-01 | 2.0E-05 |
| NR2B | IgG | 9.2E-06 | 5.8E-01 | 8.2E-08 | 6.3E-04 | 5.6E-01 | 6.5E-04 | 3.0E-03 | 2.9E-02 | 2.2E-01 | 4.6E-02 | 5.6E-03 | 2.5E-02 | 2.6E-02 |
| NRBF2 | IgG | 4.6E-02 | 3.1E-05 | 1.1E-02 | 4.8E-02 | 5.1E-03 | 1.1E-17 | 1.2E-02 | 6.1E-02 | 7.9E-01 | 1.1E-06 | 1.4E-01 | 1.2E-01 | 9.4E-05 |
| Neurofilament 68 | IgG | 1.7E-04 | 2.1E-02 | 4.0E-09 | 3.8E-02 | 9.1E-01 | 5.7E-08 | 1.0E-06 | 5.0E-02 | 3.1E-01 | 4.5E-06 | 1.0E-02 | 5.5E-01 | 1.6E-02 |
| OX40L | IgG | | | | | 2.5E-13 | | | | 1.3E-04 | | 1.3E-16 | 9.6E-06 | 1.3E-19 |
| OX40L | IgM | | | | | 7.2E-07 | | | | 1.0E-03 | | 6.5E-04 | 4.8E-03 | 1.5E-05 |
| OX40 | IgG | | 8.9E-12 | | | 7.0E-05 | | 5.5E-06 | 4.6E-09 | 6.1E-01 | 1.5E-11 | 8.0E-03 | 2.6E-04 | 9.4E-06 |
| Oligo22 | IgG | | 4.7E-27 | | | | | 7.2E-15 | 9.5E-07 | 3.3E-03 | 1.3E-12 | | | |
| Oligo26 | IgG | | 2.1E-15 | | | | | 2.3E-12 | 3.7E-06 | 3.7E-01 | 3.2E-10 | | | |
| Oligo4 | IgG | 4.6E-06 | 1.6E-15 | 2.6E-01 | 4.6E-02 | 2.2E-02 | 7.6E-02 | 3.7E-05 | 6.8E-03 | 7.1E-02 | 3.9E-04 | 5.1E-01 | 9.2E-01 | 7.1E-01 | continued

| Antigen | Isotype | HC vs OAD | HC vs SLE | HC vs SSC | HC vs APS | HC vs SS | HC vs RA | SLE vs SSC | SLE vs APS | SLE vs SS | SLE vs RA | SSC vs SS | APS vs SS | SS vs RA |
|---|---|---|---|---|---|---|---|---|---|---|---|---|---|---|
| Oligo8 | IgG | 2.3E-06 | 2.7E-17 | 1.1E-01 | 1.1E-02 | 2.0E-01 | 2.9E-01 | 1.4E-06 | 7.6E-03 | 1.3E-04 | 1.3E-05 | 9.5E-01 | 6.0E-01 | 8.8E-01 |
| Oligo9 | IgG | 2.2E-09 | 4.1E-13 | 2.0E-02 | 5.5E-02 | 2.0E-02 | 3.2E-04 | 7.3E-05 | 5.0E-02 | 5.4E-02 | 2.0E-03 | 6.5E-01 | 9.6E-01 | 9.4E-01 |
| Oligo9 | IgM | 1.9E-07 | 1.8E-04 | 3.5E-01 | 2.0E-06 | 4.3E-04 | 8.5E-06 | 5.1E-02 | 3.9E-01 | 8.3E-01 | 7.3E-01 | 4.0E-02 | 7.1E-01 | 9.8E-01 |
| PARP1 | IgG | 2.0E-02 | 2.4E-19 | 3.9E-01 | 9.1E-04 | 5.7E-01 | 2.0E-02 | 8.0E-07 | 6.3E-02 | 2.7E-03 | 3.6E-07 | 6.5E-01 | 3.8E-01 | 3.5E-01 |
| PL-12 | IgG |  | 3.9E-04 |  |  | 3.7E-03 |  | 1.5E-04 | 5.3E-04 | 6.9E-01 | 3.5E-09 | 3.9E-03 | 1.2E-02 | 4.6E-06 |
| RANTES | IgM |  | 1.3E-09 |  | 4.1E-01 |  |  | 3.5E-06 | 4.2E-02 | 2.2E-02 | 5.4E-09 |  | 9.7E-01 |  |
| RNPsm | IgM | 1.1E-01 | 4.0E-11 | 1.3E-01 | 3.0E-02 | 4.6E-01 | 2.5E-02 | 8.2E-09 | 1.6E-01 | 1.1E-02 | 4.4E-08 | 1.5E-01 | 6.2E-01 | 8.2E-02 |
| RNPsm | IgG | 4.9E-05 | 2.6E-39 | 2.7E-01 | 5.9E-04 | 2.8E-01 | 2.4E-01 | 6.0E-16 | 1.5E-05 | 2.8E-07 | 3.9E-14 | 3.2E-01 | 4.0E-01 | 3.3E-01 |
| RO60 | IgG | 6.6E-07 | 8.5E-28 | 3.5E-01 | 1.1E-01 | 3.7E-25 | 6.1E-02 | 1.3E-07 | 1.9E-04 | 3.9E-01 | 9.5E-12 | 7.9E-07 | 2.3E-04 | 1.2E-10 |
| RO60 | IgM | 1.2E-02 | 3.8E-05 | 2.3E-01 | 2.7E-01 | 1.9E-13 | 5.0E-01 | 1.5E-04 | 4.7E-01 | 9.1E-03 | 1.9E-03 | 2.7E-07 | 2.7E-02 | 9.3E-06 |
| RPLP1 | IgG |  | 2.0E-07 |  |  | 5.1E-03 |  | 4.7E-08 | 1.7E-04 | 5.0E-01 | 1.2E-09 | 3.2E-05 | 1.0E-03 | 1.9E-07 |
| RPLP2 | IgG | 4.4E-06 | 1.9E-23 | 9.9E-01 | 5.8E-02 | 6.4E-06 | 4.8E-01 | 1.7E-10 | 2.1E-03 | 2.9E-02 | 2.3E-09 | 2.8E-05 | 3.9E-01 | 2.5E-06 |
| RPP0 | IgG | 9.3E-02 | 1.2E-24 | 5.2E-04 | 4.8E-01 | 1.6E-01 | 5.6E-02 | 7.5E-10 | 2.2E-03 | 8.2E-04 | 4.8E-08 | 6.3E-02 | 9.6E-01 | 2.0E-01 |
| RibosomalP | IgG | 1.7E-02 | 4.4E-18 | 8.0E-18 | 2.6E-01 | 5.0E-06 | 5.2E-28 | 6.6E-10 | 8.3E-03 | 1.0E-01 | 1.3E-10 | 5.8E-05 | 3.3E-01 | 5.9E-07 |
| RibosomalP | IgM | 4.9E-01 | 7.9E-08 | 7.7E-01 | 4.4E-01 | 1.7E-01 | 8.1E-02 | 4.4E-04 | 3.4E-02 | 9.9E-03 | 1.4E-04 | 4.8E-01 | 9.5E-01 | 9.6E-01 |
| C4 | IgM | 2.8E-10 | 3.5E-06 | 1.7E-03 | 2.2E-03 | 8.3E-04 | 9.6E-04 |  |  |  |  |  |  |  |
| C4c | IgM | 6.6E-10 | 2.1E-03 | 3.6E-06 | 6.2E-03 | 4.8E-08 | 1.0E-07 | 6.6E-01 | 8.6E-01 | 2.5E-01 | 2.7E-01 | 2.9E-01 | 6.2E-01 | 8.2E-01 |
| CENPB | IgG | 3.0E-10 | 1.5E-10 | 6.1E-12 | 4.2E-01 | 6.2E-05 | 1.2E-02 | 3.2E-01 | 1.5E-02 | 6.6E-01 | 4.1E-03 | 2.9E-01 | 2.0E-01 | 1.9E-01 |
| CENPH | IgM | 1.4E-05 | 4.5E-07 | 8.4E-02 | 2.2E-02 | 1.1E-02 | 2.8E-02 | 4.4E-02 | 6.6E-01 | 4.8E-01 | 4.9E-02 | 6.0E-01 | 9.7E-01 | 6.8E-01 |
| CHD4 | IgM | 1.5E-09 | 1.9E-06 | 1.1E-02 | 9.1E-04 | 3.9E-06 | 3.2E-03 | 4.6E-02 |  |  | 2.1E-01 | 1.7E-02 |  | 1.2E-01 |
| CHMP2A | IgM | 3.8E-07 | 1.1E-07 | 4.8E-02 | 5.5E-02 | 8.4E-04 | 5.7E-02 | 2.9E-03 | 2.2E-01 | 5.9E-01 | 1.5E-02 | 1.0E-01 | 6.6E-01 | 2.3E-01 |
| CollagenIII | IgM | 6.5E-26 | 5.4E-15 | 1.2E-10 | 5.5E-04 | 1.7E-10 | 1.7E-13 | 8.8E-02 | 8.0E-02 | 9.0E-01 | 7.0E-01 | 2.7E-01 | 1.5E-01 | 9.2E-01 |
| EBV | IgG | 2.5E-10 | 4.7E-15 | 9.8E-07 | 1.6E-03 | 2.7E-03 | 8.5E-02 | 3.2E-02 | 1.7E-01 | 1.2E-01 | 9.0E-05 | 8.5E-01 | 9.5E-01 | 4.1E-01 |
| EXOSC10 | IgM | 4.7E-13 | 1.4E-04 | 6.8E-07 | 6.4E-02 | 2.4E-09 | 1.6E-08 | 6.6E-01 | 6.5E-01 | 1.1E-01 | 2.3E-01 | 1.4E-01 | 8.6E-02 | 4.6E-01 |
| EXOSC5 | IgM | 2.4E-18 | 1.3E-07 | 5.7E-08 | 1.7E-07 | 4.5E-12 | 6.4E-11 |  |  |  |  |  |  |  |
| EXOSC9 | IgM | 2.5E-06 | 2.2E-01 | 7.0E-03 | 4.8E-02 | 4.6E-07 | 3.0E-04 | 4.4E-01 | 5.7E-01 |  | 1.2E-01 | 7.7E-02 | 3.8E-01 | 1.9E-01 |
| FABP | IgM | 9.2E-12 | 2.2E-07 | 2.5E-06 | 3.4E-04 | 1.2E-05 | 2.2E-04 | 5.8E-01 |  | 5.9E-03 | 4.5E-01 | 7.3E-01 |  | 6.2E-01 |
| HGF | IgM | 8.1E-13 | 2.6E-16 | 2.3E-05 | 9.0E-05 | 9.1E-05 | 9.6E-05 | 3.1E-02 | 1.2E-01 | 2.0E-01 | 3.0E-02 | 8.9E-01 | 9.9E-01 | 8.8E-01 |
| HSV2 | IgM | 2.7E-04 | 3.7E-09 | 1.6E-01 | 1.3E-01 | 1.7E-01 | 8.1E-01 | 2.0E-03 | 3.3E-02 | 1.7E-02 | 1.1E-06 | 9.0E-01 | 9.5E-01 | 4.0E-01 |
| IFNg | IgM | 1.4E-10 | 7.8E-03 | 8.3E-06 | 8.5E-03 | 9.9E-05 | 3.9E-07 |  |  |  |  |  |  |  |

| Antigen | Isotype | HC vs OAD | HC vs SLE | HC vs SSC | HC vs APS | HC vs SS | HC vs RA | SLE vs SSC | SLE vs APS | SLE vs SS | SLE vs RA | SSC vs SS | APS vs SS | SS vs RA |
|---|---|---|---|---|---|---|---|---|---|---|---|---|---|---|
| LPS (lipopolysaccharide) | IgG | 6.8E-07 | 4.9E-03 | 2.9E-04 | 2.3E-01 | 2.7E-01 | 1.7E-03 | 8.4E-01 | 6.2E-01 | 4.4E-01 | 8.8E-01 | 1.0E-01 | 9.3E-01 | 2.6E-01 |
| NAP1L1 | IgG | 2.6E-04 | 4.5E-01 | 1.2E-04 | 3.2E-02 | 1.7E-01 | 5.9E-07 | 5.2E-03 | 1.1E-01 | 3.2E-01 | 3.4E-04 | | | |
| NAP1L1 | IgM | 6.9E-08 | 1.3E-05 | 3.5E-03 | 4.3E-04 | 3.7E-02 | 1.9E-07 | | | | | | | |
| Ro52 | IgG | 3.8E-17 | 7.9E-14 | 1.8E-09 | 7.8E-02 | 4.1E-33 | 3.4E-04 | 1.5E-01 | 2.2E-02 | 4.0E-03 | 1.1E-02 | 5.7E-08 | 5.7E-08 | 3.4E-10 |
| Ro52 | IgM | 2.0E-01 | 1.6E-01 | 7.1E-01 | 5.1E-01 | 6.3E-06 | 2.1E-01 | 5.2E-01 | 4.5E-01 | 1.4E-01 | 1.2E-01 | 1.5E-02 | 1.2E-01 | 6.7E-03 |
| TNFRSF12A | IgG | | | | 1.2E-10 | | | | 8.3E-04 | | | | 8.4E-02 | |
| TPO | IgM | 2.0E-09 | 1.3E-05 | 1.2E-06 | 7.3E-05 | 9.6E-06 | 4.9E-03 | 9.9E-01 | 6.3E-01 | 6.9E-01 | 6.2E-01 | 6.8E-01 | 9.4E-01 | 4.9E-01 |
| TgondiiP24 | IgM | 2.1E-16 | 7.8E-07 | 2.6E-08 | 7.8E-04 | 4.6E-07 | 5.7E-05 | 8.2E-01 | 9.4E-01 | 4.8E-01 | 6.2E-01 | 6.9E-01 | 5.4E-01 | 2.7E-01 |
| Thyroglobulin | IgM | 6.0E-11 | 1.6E-03 | 2.1E-05 | 4.1E-03 | 3.1E-07 | 1.5E-08 | 8.0E-01 | 8.2E-01 | 2.8E-01 | 2.0E-01 | 2.4E-01 | 6.8E-01 | 8.5E-01 |
| VEGF | IgM | 2.6E-13 | 4.5E-05 | 1.2E-07 | 5.3E-03 | 3.1E-04 | 2.8E-06 | | | | | | | |
| Vimentin | IgM | 2.3E-07 | 8.9E-03 | 2.1E-06 | 5.4E-01 | 4.1E-05 | 2.2E-03 | 2.6E-01 | 4.5E-01 | 3.3E-01 | 7.9E-01 | 9.1E-01 | 9.7E-02 | 5.0E-01 |
| YLK40 | IgM | 2.3E-13 | 7.4E-07 | 2.8E-08 | 7.2E-03 | 1.3E-05 | 1.3E-08 | 8.8E-01 | 7.3E-01 | 9.7E-01 | 9.3E-01 | 8.8E-01 | 7.9E-01 | 9.9E-01 |
| oligo21 | IgM | 2.3E-10 | 1.3E-07 | 1.1E-05 | 7.3E-05 | 3.7E-03 | 3.2E-05 | 3.2E-02 | 8.9E-01 | 4.8E-01 | 3.2E-01 | 5.9E-01 | 5.7E-01 | 9.0E-01 |
| oligo21 | IgG | | 5.8E-30 | | | | | 1.3E-15 | 6.3E-06 | 1.7E-04 | 8.9E-11 | | | |
| SAP | IgM | 1.4E-05 | 3.7E-09 | 5.7E-01 | 7.7E-05 | 4.4E-01 | 3.1E-03 | 3.9E-04 | 9.5E-01 | 3.8E-02 | 1.2E-01 | 8.7E-01 | 1.9E-01 | 5.2E-01 |
| SAP | IgG | | 1.1E-05 | | | | | 1.9E-10 | 9.4E-02 | 8.4E-01 | 1.2E-09 | | | |
| SDF1a | IgG | | 9.3E-41 | | | 1.2E-17 | | 4.1E-20 | 1.5E-04 | 9.0E-02 | 3.9E-16 | 8.2E-11 | 1.2E-01 | 1.8E-08 |
| SM-D3 | IgG | | 2.0E-31 | | | 6.6E-14 | | 3.8E-17 | 2.8E-06 | 7.1E-02 | 1.8E-17 | 8.5E-11 | 2.0E-03 | 2.3E-13 |
| SM-D3 | IgM | 9.5E-08 | 3.7E-09 | 2.6E-01 | 7.1E-07 | 5.2E-05 | 8.3E-02 | 1.3E-03 | 8.9E-01 | 7.7E-01 | 5.0E-03 | 2.3E-02 | 6.8E-01 | 3.3E-02 |
| SNRPA | IgG | | 5.4E-25 | | | 3.3E-02 | | 9.4E-13 | 4.6E-09 | 1.6E-04 | 8.8E-14 | 4.2E-02 | 2.5E-02 | 5.1E-03 |
| SNRPA | IgM | 5.4E-02 | 1.9E-07 | 4.4E-01 | 2.9E-02 | 5.2E-01 | 3.7E-01 | 9.0E-05 | 3.4E-01 | 9.2E-02 | 3.3E-04 | 4.3E-01 | 4.4E-01 | 4.4E-01 |
| SNRPB | IgG | 1.9E-07 | 1.2E-42 | | | 1.2E-12 | | 1.0E-17 | 9.5E-09 | 1.3E-04 | 4.3E-17 | 2.2E-06 | 3.0E-03 | 1.7E-07 |
| SNRPB | IgM | 2.7E-04 | 1.8E-17 | 7.2E-01 | 5.4E-01 | 1.5E-01 | 9.1E-01 | 1.5E-09 | 1.8E-03 | 3.6E-03 | 2.4E-08 | 3.2E-01 | 8.6E-01 | 2.5E-01 |
| SNRPC | IgM | 1.6E-02 | 7.4E-20 | | 7.2E-01 | 6.0E-01 | | 5.4E-11 | 3.1E-04 | 5.2E-05 | 1.2E-09 | 5.2E-01 | 9.9E-01 | 3.8E-01 |
| SNRPC | IgG | 6.4E-15 | 3.1E-32 | 1.9E-06 | 3.8E-03 | 4.5E-04 | 5.8E-05 | 3.9E-09 | 9.8E-05 | 6.8E-04 | 1.0E-07 | 9.0E-01 | 8.9E-01 | 8.6E-01 |
| SP100 | IgG | | 9.6E-16 | | | 1.9E-03 | | 8.7E-04 | 2.5E-06 | 9.3E-03 | 5.5E-09 | | | |
| SPTAN1 | IgM | 3.5E-03 | 1.7E-07 | | | | | 2.5E-02 | 7.9E-02 | 7.9E-01 | 1.7E-04 | 3.0E-01 | 4.1E-01 | 2.6E-02 |
| SPTAN1 | IgG | 9.4E-03 | 2.4E-20 | 5.9E-01 | 9.1E-01 | 1.7E-01 | 3.8E-01 | 8.0E-07 | 2.8E-04 | 1.7E-03 | 1.3E-09 | 4.8E-01 | 7.4E-01 | 1.8E-01 | continued

| Antigen | Isotype | HC vs OAD | HC vs SLE | HC vs SSC | HC vs APS | HC vs SS | HC vs RA | SLE vs SSC | SLE vs APS | SLE vs SS | SLE vs RA | SSC vs SS | APS vs SS | SS vs RA |
|---|---|---|---|---|---|---|---|---|---|---|---|---|---|---|
| STAT1 | IgG | 6.6E-04 | 5.6E-04 | 1.2E-05 | 5.4E-01 | 1.9E-01 | 7.9E-18 | 3.1E-05 | 5.2E-02 | 3.7E-01 | 1.4E-11 | 1.4E-02 | 4.4E-01 | 8.9E-07 |
| STAT4 | IgG | 2.5E-03 | 1.1E-01 | 5.8E-05 | 5.1E-01 | 2.7E-02 | 3.8E-14 | 1.8E-03 | 8.3E-01 | 5.1E-01 | 1.6E-07 | 7.4E-03 | 5.9E-01 | 1.7E-05 |
| STAT5a | IgG | | 9.3E-06 | | | 1.9E-02 | | 4.8E-13 | 4.6E-09 | 6.1E-01 | 2.1E-13 | 1.6E-07 | 2.4E-05 | 4.0E-08 |
| STAT6 | IgG | 2.6E-03 | 3.2E-01 | 9.9E-03 | 6.7E-01 | 9.0E-01 | 6.0E-12 | 2.6E-02 | 8.5E-01 | 6.6E-01 | 5.2E-07 | 2.9E-01 | 9.1E-01 | 5.2E-04 |
| SYND1 | IgM | 3.5E-06 | 1.2E-07 | 2.1E-02 | 1.6E-03 | 4.5E-03 | 6.9E-03 | 1.1E-01 | 9.5E-01 | 5.7E-01 | 1.4E-01 | 7.0E-01 | 8.6E-01 | 7.6E-01 |
| SerpinG1 | IgG | 6.9E-02 | 1.4E-03 | 5.2E-08 | 3.5E-03 | 2.6E-04 | 4.9E-01 | 3.1E-04 | 2.5E-02 | 3.7E-01 | 2.3E-01 | 3.8E-03 | 7.1E-02 | 2.9E-01 |
| Sm-D1 | IgG | | 2.5E-30 | | | 1.7E-12 | | 6.6E-14 | 4.8E-05 | 4.1E-02 | 3.4E-12 | 6.0E-07 | 3.2E-02 | 1.4E-06 |
| Sm-D1 | IgM | 5.1E-08 | 3.4E-12 | 3.2E-01 | 2.0E-08 | 2.0E-04 | 3.0E-02 | 4.3E-04 | 9.4E-01 | 4.0E-01 | 3.0E-03 | 1.0E-01 | 4.1E-01 | 2.4E-01 |
| SmD | IgG | | 1.0E-34 | | | 3.8E-17 | | 4.0E-21 | 3.7E-06 | 1.0E-01 | 1.7E-19 | 7.4E-17 | 2.2E-03 | 1.2E-17 |
| SmD | IgM | 1.1E-09 | 9.7E-13 | 1.4E-01 | 8.2E-08 | 9.2E-08 | 2.3E-02 | 2.9E-04 | 9.5E-01 | 8.9E-01 | 2.3E-03 | 5.7E-03 | 9.7E-01 | 1.8E-02 |
| Sm | IgG | 1.7E-07 | 3.7E-39 | 2.4E-02 | 4.2E-03 | 5.6E-01 | 9.7E-01 | 1.4E-13 | 8.8E-05 | 5.3E-07 | 1.3E-12 | 1.0E-01 | 2.3E-01 | 7.1E-01 |
| Sm | IgM | 4.3E-01 | 2.7E-12 | 7.7E-02 | 9.0E-01 | 5.8E-01 | 2.8E-03 | 3.5E-06 | 6.3E-02 | 9.1E-03 | 1.1E-06 | 8.0E-01 | 9.2E-01 | 4.1E-01 |
| TGM2 | IgG | 2.4E-15 | 1.1E-07 | 1.2E-07 | 1.2E-07 | 4.0E-05 | 1.9E-06 | 7.1E-01 | 6.5E-01 | 9.3E-01 | 6.9E-01 | 9.1E-01 | 5.5E-01 | 8.9E-01 |
| THBS1 | IgG | 8.5E-10 | 9.2E-01 | 4.3E-16 | 3.9E-04 | 7.6E-02 | 9.5E-23 | 3.9E-05 | 6.9E-02 | 3.2E-01 | 2.6E-07 | 8.3E-04 | 8.9E-02 | 2.9E-05 |
| TNFa | IgG | 1.1E-03 | 3.7E-01 | 3.6E-02 | 4.6E-01 | 6.0E-02 | 4.7E-13 | 5.5E-01 | 9.7E-01 | 2.5E-01 | 1.2E-03 | 8.2E-02 | 4.3E-01 | 9.4E-03 |
| TNFb | IgG | 8.8E-05 | 4.8E-09 | 2.5E-02 | 3.5E-01 | 1.3E-01 | 7.5E-01 | 1.3E-02 | 6.4E-02 | 1.1E-01 | 9.3E-05 | 1.0E+00 | 8.9E-01 | 2.0E-01 |
| TRAIL | IgG | | 1.0E-13 | | | 1.4E-05 | | 1.4E-05 | 3.7E-03 | 6.0E-01 | 1.3E-03 | 6.0E-03 | 1.2E-01 | 7.2E-02 |
| Tyk2 | IgG | 1.9E-08 | 7.8E-01 | 1.4E-10 | 8.7E-07 | 9.8E-01 | 4.8E-14 | 1.8E-03 | 2.3E-02 | 9.1E-01 | 1.4E-04 | 1.8E-02 | 8.9E-02 | 3.5E-03 |
| Tyk2 | IgM | 4.2E-07 | 5.3E-04 | 3.3E-05 | 1.2E-03 | 1.1E-01 | 2.3E-04 | 8.1E-01 | 6.4E-01 | 7.2E-01 | 8.4E-01 | 6.0E-01 | 6.4E-01 | 6.6E-01 |
| U1snRNP | IgG | 3.3E-08 | 1.2E-27 | 4.4E-01 | 9.2E-02 | 1.3E-07 | 2.7E-01 | 3.4E-11 | 1.0E-03 | 1.2E-02 | 6.6E-09 | 6.1E-07 | 3.6E-01 | 2.5E-06 |
| WNV | IgM | 9.2E-02 | 1.2E-02 | 1.3E-02 | 8.6E-01 | 2.1E-01 | 4.1E-05 | 4.4E-04 | 5.1E-01 | 4.3E-02 | 5.7E-07 | 8.8E-01 | 8.9E-01 | 3.3E-01 |
| XRCC5 | IgG | 1.9E-02 | 9.2E-13 | 7.5E-01 | | 1.5E-01 | | 5.7E-04 | 2.2E-02 | 4.7E-02 | 2.0E-04 | 7.0E-01 | 6.8E-01 | 4.1E-01 |
| Zyxin | IgG | | 3.2E-02 | | | | | 1.3E-04 | 9.6E-04 | 7.6E-02 | 5.9E-07 | | | |
| huIgG | IgG | 9.6E-05 | 9.2E-11 | 3.5E-02 | 9.8E-02 | 8.8E-02 | 1.5E-01 | 8.6E-03 | 2.6E-01 | 3.3E-01 | 3.4E-03 | 8.7E-01 | 9.9E-01 | 7.6E-01 |
| oligo10 | IgG | 2.2E-08 | 2.4E-12 | 4.6E-02 | 5.8E-02 | 6.6E-02 | 2.8E-03 | 1.6E-05 | 3.9E-02 | 2.2E-02 | 3.0E-04 | 7.3E-01 | 9.9E-01 | 9.2E-01 |
| oligo11 | IgG | 5.3E-08 | 3.5E-13 | 3.7E-02 | 1.2E-01 | 1.8E-01 | 3.0E-03 | 1.3E-05 | 1.8E-02 | 8.2E-03 | 1.9E-04 | 9.9E-01 | 9.6E-01 | 6.8E-01 |
| oligo16 | IgG | | 1.8E-27 | | | | | 2.5E-12 | 1.7E-05 | 2.3E-03 | 1.5E-14 | | | |
| oligo17 | IgG | | 5.1E-30 | | | | | 2.4E-11 | 7.0E-05 | 1.2E-02 | 8.9E-14 | | | |
| oligo19 | IgG | 4.6E-03 | 1.1E-16 | 7.2E-01 | 7.1E-02 | 3.1E-01 | 4.1E-01 | 6.9E-08 | 5.5E-03 | 2.5E-03 | 5.8E-08 | 5.1E-01 | 8.6E-01 | 4.1E-01 |
| oligo1 | IgG | | 5.9E-20 | | | 3.8E-05 | | 2.3E-09 | 1.3E-03 | 3.1E-02 | 1.2E-09 | 2.4E-03 | 3.0E-01 | 2.6E-04 | continued

| Antigen | Isotype | HC vs OAD | HC vs SLE | HC vs SSC | HC vs APS | HC vs SS | HC vs RA | SLE vs SSC | SLE vs APS | SLE vs SS | SLE vs RA | SSC vs SS | APS vs SS | SS vs RA |
|---|---|---|---|---|---|---|---|---|---|---|---|---|---|---|
| oligo20 | IgG | | 8.7E-26 | | | | | | | | | | | |
| oligo27 | IgM | 7.6E-11 | 2.1E-09 | 2.4E-02 | 2.9E-09 | 1.2E-07 | 3.9E-05 | 8.0E-12 | 4.8E-05 | 1.0E-03 | 4.3E-13 | | | |
| oligo27 | IgG | 5.9E-09 | 6.1E-15 | 1.1E-02 | 4.3E-02 | 1.5E-01 | 3.3E-03 | 5.0E-03 | 6.0E-01 | 8.4E-01 | 3.6E-01 | 6.2E-03 | 8.9E-01 | 3.8E-01 |
| oligo28 | IgG | 8.2E-09 | 5.9E-20 | 1.8E-01 | 1.1E-01 | 2.5E-03 | 1.7E-03 | 1.9E-05 | 1.6E-02 | 1.3E-02 | 9.7E-05 | 9.7E-01 | 9.0E-01 | 8.2E-01 |
| oligo28 | IgM | 2.0E-08 | 3.5E-09 | 4.6E-01 | 1.7E-07 | 1.1E-05 | 2.4E-05 | 4.1E-09 | 3.3E-03 | 2.2E-02 | 3.8E-06 | 1.2E-01 | 7.5E-01 | 6.4E-01 |
| oligo29 | IgG | 5.6E-07 | 1.1E-18 | 4.3E-01 | 1.7E-01 | 1.9E-02 | 1.6E-02 | 2.4E-03 | 8.2E-01 | 8.5E-01 | 4.9E-01 | 2.4E-02 | 7.1E-01 | 8.3E-01 |
| oligo29 | IgM | 1.1E-09 | 9.6E-08 | 1.1E-01 | 3.2E-09 | 4.2E-05 | 1.1E-05 | 4.6E-09 | 2.1E-03 | 6.0E-03 | 5.8E-06 | 2.3E-01 | 8.4E-01 | 8.0E-01 |
| oligo30 | IgM | 1.6E-07 | 2.2E-07 | 4.9E-01 | 2.1E-07 | 2.5E-04 | 5.5E-04 | 1.9E-02 | 3.9E-01 | 9.6E-01 | 7.6E-01 | 7.9E-02 | 4.1E-01 | 9.0E-01 |
| oligo30 | IgG | 2.1E-07 | 7.7E-14 | 4.6E-02 | 8.3E-02 | 1.1E-01 | 2.0E-02 | 2.1E-01 | 6.2E-01 | 9.1E-01 | 3.2E-01 | 2.2E-02 | 6.2E-01 | 6.4E-01 |
| oligo5 | IgG | 1.0E-07 | 1.8E-19 | 8.7E-02 | 3.2E-02 | 4.4E-02 | 2.3E-02 | 1.8E-05 | 1.9E-02 | 3.5E-02 | 2.8E-04 | 8.5E-01 | 9.9E-01 | 9.8E-01 |
| oligo7 | IgG | 5.2E-07 | 7.8E-20 | 3.1E-01 | 2.8E-02 | 2.0E-03 | 5.4E-01 | 1.4E-06 | 3.7E-03 | 9.1E-03 | 2.2E-05 | 7.1E-01 | 9.9E-01 | 8.9E-01 |
| oxLDL | IgG | 7.5E-03 | 6.6E-07 | 7.3E-08 | 1.5E-04 | 1.3E-03 | 9.9E-02 | 1.9E-09 | 1.1E-02 | 1.4E-02 | 4.3E-10 | 7.9E-02 | 9.0E-01 | 1.8E-02 |
| pADPr | IgG | 2.8E-04 | 9.6E-11 | 3.2E-01 | 1.8E-02 | 1.1E-02 | | 3.7E-03 | 5.1E-02 | 9.8E-01 | 1.1E-01 | 5.5E-02 | 2.3E-01 | 3.6E-01 |
| | | | | | | | | 2.9E-04 | 2.4E-01 | 4.8E-02 | 1.1E-06 | 3.2E-01 | 9.9E-01 | 3.3E-02 |

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 1
aaaaaaaaaa aaaaaaaaaa                                            20

<210> SEQ ID NO 2
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 2
gggggggggg ggggggg                                               17

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 3
gggggggggg gggggggggg                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4
ccataattgc aaacgttctg                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5
ccataattgc aaagcttctg                                            20

<210> SEQ ID NO 6
<211> LENGTH: 20
<212> TYPE: DNA
```

```
<213> ORGANISM: Artificial Sequence
<220> FEATURE:
<223> OTHER INFORMATION: Synthetic oligonucleotide

<400> SEQUENCE: 6
tttttttttt tttttttttt                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7
ttgggggggg ggggggggtt                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ccataattcg aaacgttctg                                              20

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9
ttagggttag ggttagggtt aggg                                         24

<210> SEQ ID NO 10
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 10
gttttttttt tttttttg                                                18

<210> SEQ ID NO 11
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 11
gttttttttt ttttttt                                                 17

<210> SEQ ID NO 12
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 12
tttttttttt tttttg                                                  17
```

```
<210> SEQ ID NO 13
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 13
tttttttttt tttttttgg                                                    18

<210> SEQ ID NO 14
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 14
gggggggggg gggggt                                                       17

<210> SEQ ID NO 15
<211> LENGTH: 7
<212> TYPE: DNA
<213> ORGANISM: Artificial Sequence
<220> FEATURE:
<223> OTHER INFORMATION: Synthetic oligonucleotide

<400> SEQUENCE: 15 ggggggg                                                                  7

<210> SEQ ID NO 16
<211> LENGTH: 9
<212> TYPE: DNA
<213> ORGANISM: Artificial Sequence
<220> FEATURE:
<223> OTHER INFORMATION: Synthetic oligonucleotide

<400> SEQUENCE: 16 ggggggggg                                                                9

<210> SEQ ID NO 17
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 17
tggggggggg gggggg                                                       17

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18
cccccccccc cccccccccc                                                   20

<210> SEQ ID NO 19
<211> LENGTH: 20
<212> TYPE: DNA
<213> ORGANISM: Artificial Sequence
<220> FEATURE:
```

```
<223> OTHER INFORMATION: Synthetic oligonucleotide

<400> SEQUENCE: 19
cgcgcgcgcg cgcgcgcgcg                                           20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
gagagagaga gagagagaga                                           20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gtgtgtgtgt gtgtgtgtgt                                           20

<210> SEQ ID NO 22
<211> LENGTH: 14
<212> TYPE: DNA
<213> ORGANISM: Artificial Sequence
<220> FEATURE:
<223> OTHER INFORMATION: Synthetic oligonucleotide

<400> SEQUENCE: 22
gggggggggg gggg                                                 14
```

DIAGNOSIS OF AUTOIMMUNE DISEASES

FIELD OF THE INVENTION

The invention provides methods for diagnosing and treating autoimmune diseases. Particularly, the invention provides methods and antigen probe sets, array or chips for differential diagnosis of specific autoimmune diseases, including autoimmune rheumatic disorders.

BACKGROUND OF THE INVENTION

Many types of autoimmune diseases exist, among which autoimmune rheumatic disorders (ARDs) are included. In ARDs, the immune system attacks the joints and certain systems. The cause of many of the ARDs is unknown. Among these disorders are systemic lupus erythematosus (SLE), rheumatoid arthritis (RA), and Sjögren's syndrome (SS), each having a long list of characteristic symptoms. While some of the symptoms are unique to each disease, and can therefore assist in differential diagnosis, such symptoms are not always present. In addition, ARDs are often difficult to distinguish due to overlapping signs and symptoms. Non-limiting examples for overlapping symptoms include Raynaud's phenomenon, joint pain, joint stiffness, joint swelling, joint redness, joint tenderness, joint warmth, impaired joint range of motion, fatigue, and inflammation.

The presence of autoantibodies is a hallmark of many autoimmune diseases, which has long been used for the diagnosis and classification of these diseases. Autoantibodies may exist years before the diagnosis of an autoimmune disease, and thus could potentially be used for early prediction of the disease onset. Anti-nuclear antibodies (ANAs) have been observed in a variety of autoimmune disorders, including autoimmune rheumatic diseases, and in chronic inflammatory diseases, infectious diseases and malignancies, and can also be induced by certain drugs. Thus, while ANA testing is being considered as an auxiliary diagnostic tool by physicians, it may only be used as a general indicator of such diseases due to lack of specificity.

Lab-associated variances in test results of ANA have been demonstrated, reducing the reliability of this assay. Therefore, it is currently recommended that ANA positive test results be followed by additional diagnostic tools.

To date, no single autoantibody has demonstrated clinically significant sensitivity and specificity for the diagnosis of individual ARD, specifically at early stage of the disease. There remains an unmet need to discover serological tests for the diagnosis of individual ARDs and other autoimmune diseases.

SLE is a chronic, recurrent, potentially fatal multisystem inflammatory disorder mainly affecting women. SLE is associated with a large spectrum of autoantibodies. IgG antibodies to more than 100 different antigens including DNA, nucleosomes, histones, viral antigens, transcription factors and more have been reported in different SLE patients. As there is no approved serologic diagnosis of SLE, SLE is diagnosed on the basis of eleven criteria defined by the American College of Rheumatology (ACR). These criteria include malar rash, discoid rash, photosensitivity, oral ulcers, arthritis, serositis, renal disorder, neurologic disorder, hematologic disorder (e.g., leucopenia, lymphopenia, hemolytic anemia or thrombocytopenia), immunologic disorder and antibody abnormalities (particularly ANA and anti-DNA antibodies). According to these criteria, subjects can be clinically diagnosed with SLE if they meet at least four of the eleven criteria. Recently, the Systemic Lupus Collaborating Clinics (SLICC) revised these criteria. Nevertheless, SLE is still possible even in cases when less than four criteria are present ('pre-clinical' lupus). Patients with indeterminate findings are evaluated with extensive serologic testing and repeated clinical examinations until a definitive diagnosis of SLE or some other disease can be made. These patients are followed extensively, with a mean time from the initial visit until disposition of about 6 years.

RA is a chronic inflammatory autoimmune disease characterized by joint inflammation, joint swelling, joint tenderness, and destruction of synovial joints, leading to severe disability and premature mortality. RA can be difficult to diagnose as many other ARDs share arthritis manifestations. There is no single serologic test for this disease. The most widely used antibodies for RA diagnosis are anti-rheumatoid factor (RF) antibodies and anti-citrullinated protein antibodies (ACPA) (tested as anti-cyclic citrullinated peptide [anti-CCP]). Autoimmunity and the overall systemic and articular inflammatory load drive the destructive progression of the disease. Structural changes, which can be visualized by conventional radiography or other imaging techniques, are also used as part of the differential diagnosis. Established joint damage is rarely apparent in the very early stages of disease, but rather accumulates consistently over time. Early diagnosis of RA is crucial for treatment initiation which can stop disease progression. Therefore, early diagnosis of RA remains a challenge to rheumatologists.

SS is a chronic, progressive autoimmune disease primarily affecting women. Diagnosis of SS presently requires an invasive salivary gland tissue biopsy, and a long delay from the start of the symptoms to final diagnosis has been frequently observed. The most widely used biomarkers of SS are serum IgG autoantibodies against two nuclear proteins, Ro-52/SSA and La/SSB. Although anti-SSA and anti-SSB are clinically useful biomarkers, they are neither specific to SS nor correlated with clinical severity of SS. In addition, anti-SSA and anti-SSB antibodies are present only in 5-15% of the patients with SS secondary to RA and 38.5% of patients with SS secondary to SLE.

SSc is a group of autoimmune diseases that can result in changes to the skin, blood vessels, muscles, and internal organs. The disease can be either localized to the skin or involve other organs in addition to the skin. Symptoms can include thickened skin, stiffness, feeling tired, and poor blood flow to the fingers or toes with cold exposure. There is no single test for scleroderma and hence the diagnosis is often a matter of exclusion. Laboratory testing is based on evaluating the levels of antitopoisomerase antibodies, like anti-scl70 (causing a diffuse systemic form), or anticentromere antibodies (causing a limited systemic form). Other autoantibodies can be seen, such as anti-U3 or anti-RNA polymerase.

APS is an autoimmune, hypercoagulable state caused by antiphospholipid antibodies. APS provokes blood clots (thrombosis) in both arteries and veins as well as pregnancy-related complications such as miscarriage, stillbirth, preterm delivery, and severe preeclampsia. The diagnostic criteria require one clinical event, i.e. thrombosis or pregnancy complication, and two antibody blood tests spaced at least three months apart that confirm the presence of either lupus anticoagulant or anti-$\beta_2$-glycoprotein-I.

Attempts to develop diagnostic tests for various autoimmune diseases including ARDs have been reported. However, no test providing reliable and accurate differential diagnosis of these diseases has been approved for clinical use.

International Patent Application Publication No. WO 2011/099012 discloses methods and kits for diagnosing SLE in a subject. WO 2011/099012 further discloses a specific antibody profile useful in diagnosing SLE in a subject.

International Patent Application Publication No. WO 2014/091490 discloses methods and kits for diagnosing SLE or SSc in a subject. WO 2014/091490 further discloses a specific antibody reactivity profile useful in diagnosing SLE or scleroderma in a subject.

International Patent Application Publication No. WO 2015/101987 discloses method of assaying or monitoring the determining immunological competence in a subject. The method comprises measuring the levels of antibodies in a sample obtained from a subject to poly-guanine oligonucleotides.

International Patent Application Publication No. WO 2015/101988 discloses methods and kits for diagnosing SLE in a subject. WO 2015/101988 further discloses specific oligonucleotide antibody reactivities useful in diagnosing SLE in a subject.

U.S. Patent Application Publication No. 2017/0074875 discloses methods for identifying markers for SLE and to the markers identified with the aid of this method, which can differentiate between SLE and other autoimmune diseases and between different SLE subgroups.

Fattal et al. described the use of an antigen microarray and informatics analysis in investigating anti-DNA autoantibodies. Particularly, Fattal et al. examined IgM and IgG antibodies to poly-G and other oligonucleotides in the sera of healthy persons and those diagnosed with SLE, SSc, or pemphigus vulgaris (PV) (Immunology, 2015, Vol. 146(3): 401-410).

Putterman et al. described the development, verification and validation of a rule-out test for a definitive rule-out diagnosis of SLE. The test uses micro-array technology platform to identify discriminating patterns of circulating autoantibodies among SLE patients compared to self-declared healthy individuals (J. Immunol. Methods, 2016, Vol. 429:1-6).

Hueber et al. reported the attempts to develop an antigen microarray technology to identify distinct serum antibody profiles in patients with RA for providing diagnostic information and allowing stratification of patients with early RA into clinically relevant disease subsets (Arthritis Rheum., 2005, Vol. 52(9):2645-55).

Szodoray and Alex reviewed the technology and the applications for protein arrays in the diagnosis and prognosis of RA. According to the authors, clinical assessment tools could be derived from protein arrays, which may provide a means to continually track patients, allowing better evaluation of intervention strategies on a patient-specific basis and identification of diagnostic and disease activity biomarkers that could be used to guide optimal therapy in RA (Mol. Diagn. Ther., 2011, Vol. 15(5):247-254).

Hu and coworkers attempted to identify salivary autoantibody biomarkers for primary SS (pSS) using a protein microarray approach, and identified 24 potential autoantibody biomarkers that can discriminate patients with pSS from both patients with SLE and healthy individuals (Proteomics, 2011, Vol. 11(8): 1499-1507).

Although autoantibodies have long been used for diagnostics in autoimmune diseases, there are two major factors that confound the effective use of autoantibody biomarkers for clinical applications. First, an autoantibody biomarker is often present in multiple autoimmune diseases. For instance, several autoantibodies present in SS patients were also found in patients with SLE and RA, two diseases often coexisting with SS. Second, the development of autoantibodies to any given antigen is typically found in only a fraction of patients due to disease heterogeneity. Consequently, to provide sensitive and reliable clinical tests for a specific autoimmune disease, one needs to employ multiple diagnostic assays to improve the sensitivity and specificity.

Despite considerable progress in diagnosing autoimmune diseases and disorders, there remains a need for methods for the differential diagnosis of each one of the autoimmune diseases, particularly of ARDs, in order to develop therapeutic means so as to prevent disease progression and organ damage.

SUMMARY OF THE INVENTION

Subjects can express a variety of inflammatory symptoms that can be common to many autoimmune and non-autoimmune diseases. The invention provides methods and assays, including antigen probe sets, antigen arrays and antigen chips, for diagnosing a subject as having an autoimmune disease when the subject expresses one or more inflammatory and possibly rheumatic symptoms, to identify the specific autoimmune disease, i.e., rheumatoid arthritis (RA), Sjögren's syndrome (SS), systemic lupus erythematosus (SLE), Scleroderma (SSc) or anti-phospholipid syndrome (APS), and to identify therapeutic targets for treating the autoimmune disease.

The methods and assays constructed according to the principles of the invention are based, in part, on the unexpected findings that different antibody reactivities to antigen arrays were observed when serum samples obtained from subjects having different autoimmune diseases were compared to serum samples obtained from healthy control subjects or from patients with other diseases. Surprisingly, distinct antibody reactivity profiles were identified in the serum samples obtained from patients having different diseases. Unexpectedly, specific antibody reactivities to selected antigens were identified which enable not only differentiation between subjects afflicted with an autoimmune disorder and healthy control subjects, but also differentiation between autoimmune diseases, including symptomatically and serologically related diseases such as RA, SS, SLE, SSc and APS.

According to one aspect of the invention, methods are provided for diagnosing an autoimmune disease in a subject, the method including:
  i. obtaining a sample from the subject;
  ii. determining the reactivity of antibodies in the sample obtained from said subject to a plurality of antigens selected from Table 1, thereby obtaining a reactivity pattern of said sample to the plurality of antigens;
  iii. comparing the reactivity pattern of said sample to a healthy control reactivity pattern to said plurality of antigens by a supervised classification algorithm, wherein a significantly different reactivity of the sample obtained from the subject compared to the healthy control reactivity pattern indicates that said subject has an autoimmune rheumatic disease.

According to some embodiments, the autoimmune disease to be diagnosed is selected from the group consisting of Systemic Lupus Erythematosus (SLE), Rheumatoid Arthritis (RA), Scleroderma (SSc), Sjögren's syndrome (SS), and Anti-Phospholipid Syndrome (APS).

According to additional embodiments, if the subject has been diagnosed by the above method as having an autoimmune disease, the method can further include identifying the autoimmune disease in said subject by the steps including:

i. determining the reactivity of antibodies in the sample obtained from the subject to a plurality of antigens selected from at least one of Tables 8-12, thereby obtaining a reactivity pattern of said sample to the plurality of antigens;

ii. comparing the reactivity pattern of said sample to a healthy control reactivity pattern to said plurality of antigens, by a supervised classification algorithm, wherein:

a significantly different reactivity pattern of the sample obtained from the subject to a plurality of antigens selected from Table 8 compared to the healthy control reactivity pattern indicates that said subject has SLE, a significantly different reactivity pattern of the sample obtained from the subject to a plurality of antigens selected from Table 9 compared to the healthy control reactivity pattern indicates that said subject has SSc, a significantly different reactivity pattern of the sample obtained from the subject to a plurality of antigens selected from Table 10 compared to the healthy control reactivity pattern indicates that said subject has APS, a significantly different reactivity pattern of the sample obtained from the subject to a plurality of antigens selected from Table 11 compared to the healthy control reactivity pattern indicates that said subject has SS, and/or a significantly different reactivity pattern of the sample obtained from the subject to a plurality of antigens selected from Table 12 compared to the healthy control reactivity pattern indicates that said subject has RA.

According to another aspect of the invention, methods are provided for diagnosing an autoimmune disease selected from the group consisting of systemic lupus erythematosus (SLE), rheumatoid arthritis (RA), scleroderma (SSc), Sjögren's Syndrome (SS), and anti-phospholipid syndrome (APS) in a subject, the method may include:

i. obtaining a sample from a subject suspected of having an autoimmune rheumatic disease;

ii. determining the reactivity of antibodies in the sample obtained from the subject to a plurality of antigens selected from at least one of Tables 8-12, thereby obtaining a reactivity pattern of said sample to the plurality of antigens;

iii. comparing the reactivity pattern of said sample to a healthy control reactivity pattern to said plurality of antigens, by a supervised classification algorithm, wherein:

a significantly different reactivity pattern of the sample obtained from the subject to a plurality of antigens selected from Table 8 compared to the healthy control reactivity pattern indicates that said subject has SLE, a significantly different reactivity pattern of the sample obtained from the subject to a plurality of antigens selected from Table 9 compared to the healthy control reactivity pattern indicates that said subject has SSc, a significantly different reactivity pattern of the sample obtained from the subject to a plurality of antigens selected from Table 10 compared to the healthy control reactivity pattern indicates that said subject has APS, a significantly different reactivity pattern of the sample obtained from the subject to a plurality of antigens selected from Table 11 compared to the healthy control reactivity pattern indicates that said subject has SS, and/or a significantly different reactivity pattern of the sample obtained from the subject to a plurality of antigens selected from Table 12 compared to the healthy control reactivity pattern indicates that said subject has RA.

According to another aspect of the invention, methods are provided for differentially diagnosing an autoimmune disease, including:

(i) obtaining a sample from a subject diagnosed as having the autoimmune disease;

(ii) contacting the sample, under conditions such that a specific antigen-antibody complex is formed, with antigens selected from at least one of Tables 2-7;

(iii) determining the reactivity of antibodies in said sample to the antigens, thereby determining the reactivity pattern of said sample to said antigens; and (iv) comparing the reactivity pattern of said sample obtained from the subject to a control reactivity pattern to said antigens by a supervised classification algorithm, wherein:

a significantly different reactivity pattern of the sample obtained from the subject to a plurality of antigens selected from Table 2 compared to a RA control reactivity pattern to said antigens indicates that said subject has SLE, a significantly different reactivity pattern of the sample obtained from said subject to a plurality of antigens selected from Table 2 compared to a SLE control reactivity pattern to said antigens indicates that said subject has RA, a significantly different reactivity pattern of the sample obtained from said subject to a plurality of antigens selected from Table 3 compared to a SSc control reactivity pattern to said antigens indicates that said subject has SLE, a significantly different reactivity pattern of the sample obtained from said subject to a plurality of antigens selected from Table 3 compared to a SLE control reactivity pattern to said antigens indicates that said subject has SSc, a significantly different reactivity pattern of the sample obtained from said subject to a plurality of antigens selected from Table 4 compared to an APS control reactivity pattern to said antigens indicates that said subject has SLE, a significantly different reactivity pattern of the sample obtained from said subject to a plurality of antigens selected from Table 4 compared to an SLE control reactivity pattern to said antigens indicates that said subject has APS, a significantly different reactivity pattern of the sample obtained from said subject to a plurality of antigens selected from Table 5 compared to a SSc control reactivity pattern to said antigens indicates that said subject has SS, a significantly different reactivity pattern of the sample obtained from said subject to a plurality of antigens selected from Table 5 compared to a SS control reactivity pattern to said antigens indicates that said subject has SSc, a significantly different reactivity pattern of the sample obtained from said subject to a plurality of antigens selected from Table 6 compared to a RA control reactivity pattern to said antigens indicates that said subject has SS, a significantly different reactivity pattern of the sample obtained from said subject to a plurality of antigens selected from Table 6 compared to a SS control reactivity pattern indicates that said subject has RA, a significantly different reactivity pattern of the sample obtained from said subject to a plurality of antigens comprising the antigen of Table 7 compared to a SS control reactivity pattern to said antigens indicates that said subject has SLE, and/or a significantly different reactivity pattern of the sample obtained from said subject to a plurality of antigens comprising the antigen of Table 7 compared to a SLE control reactivity pattern indicates that said subject has SS.

According to some embodiments, the method of differentially diagnosing if the subject is having SLE or RA includes:

(a) determining the reactivity of antibodies in the sample obtained from the subject to a plurality of antigens selected from Table 2, thereby obtaining a reactivity pattern of said sample to the plurality of antigens selected from Table 2;

(b) comparing the reactivity pattern of said sample to the plurality of antigens selected from Table 2 to a control reactivity pattern to said plurality of antigens selected from Table 2 by a supervised classification algorithm, wherein the control is a RA control, and a significantly different reactivity pattern of the sample obtained from said subject compared to the RA control reactivity pattern indicates that said subject has SLE, and/or wherein the control is a SLE control, and a significantly different reactivity pattern of the sample obtained from said subject compared to the SLE control reactivity pattern indicates that said subject has RA.

According to additional embodiments, the method of differential diagnosing if the subject is having SLE or SSc includes:

(a) determining the reactivity of antibodies in the sample obtained from the subject to a plurality of antigens selected from Table 3, thereby obtaining a reactivity pattern of said sample to the plurality of antigens;

(b) comparing the reactivity pattern of said sample obtained from the subject to the plurality of antigens selected from Table 3, to a control reactivity pattern to said plurality of antigens selected from Table 3 by a supervised classification algorithm, wherein the control is a SSc control, and a significantly different reactivity pattern of the sample obtained from said subject compared to the SSc control reactivity pattern indicates that said subject has SLE, and/or wherein the control is a SLE control, and a significantly different reactivity pattern of the sample obtained from said subject compared to the SLE control reactivity pattern indicates that said subject has SSc.

According to still further embodiments, the method of differential diagnosing if the subject is having SLE or APS includes:

(a) determining the reactivity of antibodies in the sample obtained from the subject to a plurality of antigens selected from Table 4, thereby obtaining a reactivity pattern of said sample to the plurality of antigens;

(b) comparing the reactivity pattern of said sample obtained from the subject to the plurality of antigens selected from Table 4 to a control reactivity pattern to said plurality of antigens selected from Table 4 by a supervised classification algorithm, wherein the control is an APS control, and a significantly different reactivity pattern of the sample obtained from said subject compared to the APS control reactivity pattern indicates that said subject has SLE, and/or wherein the control is a SLE control, and a significantly different reactivity pattern of the sample obtained from said subject compared to the SLE control reactivity pattern indicates that said subject has APS.

According to yet further embodiments, the method of differential diagnosing if the subject is having SS or SSc includes:

(a) determining the reactivity of antibodies in the sample obtained from the subject to a plurality of antigens selected from Table 5, thereby obtaining a reactivity pattern of said sample to the plurality of antigens;

(b) comparing the reactivity pattern of said sample obtained from the subject to the plurality of antigens selected from Table 5 to a control reactivity pattern to said plurality of antigens selected from Table 5 by a supervised classification algorithm, wherein the control is a SSc control, and a significantly different reactivity pattern of the sample obtained from said subject compared to the SSc control reactivity pattern indicates that said subject has SS, and/or wherein the control is a SS control, and a significantly different reactivity pattern of the sample obtained from said subject compared to the SS control reactivity pattern indicates that said subject has SSc.

According to yet further embodiments, the method of differential diagnosing if the subject is having SS or RA includes:

(a) determining the reactivity of antibodies in the sample obtained from the subject to a plurality of antigens selected from Table 6, thereby obtaining a reactivity pattern of said sample to the plurality of antigens;

(b) comparing the reactivity pattern of said sample obtained from the subject to the plurality of antigens selected from Table 6 to a control reactivity pattern to said plurality of antigens selected from Table 6 by a supervised classification algorithm, wherein the control is a RA control, and a significantly different reactivity pattern of the sample obtained from said subject compared to the RA control reactivity pattern indicates that said subject has SS, and/or wherein the control is a SS control, and a significantly different reactivity pattern of the sample obtained from said subject compared to the SS control reactivity pattern indicates that said subject has RA.

According to still further embodiments, the method of differential diagnosing if the subject is having SLE or SS includes:

(a) determining the reactivity of antibodies in the sample obtained from the subject to a plurality of antigens comprising the antigen of Table 7, thereby obtaining a reactivity pattern of said sample to the plurality of antigens;

(b) comparing the reactivity pattern of said sample obtained from the subject to the plurality of antigens to a control reactivity pattern to said plurality of antigens by a supervised classification algorithm, wherein the control is a SS control, and a significantly different reactivity pattern of the sample obtained from said subject compared to the SS control reactivity pattern indicates that said subject has SLE, and/or wherein the control is a SLE control, and a significantly different reactivity pattern of the sample obtained from said subject compared to the SLE control reactivity pattern indicates that said subject has SS.

According to some embodiments, the sample being used for any one of the methods disclosed herein is selected from the group consisting of a serum sample, a plasma sample, and a blood sample.

According to additional embodiments, the reactivity of antibodies may include IgM reactivity, IgG reactivity, or a combination thereof. Exemplary embodiments of specific IgG and IgM reactivities are provided in Tables 1-28 and 30-34 herein.

According to further embodiments, the supervised classification algorithm is selected from the group consisting of Support Vector Machine (SVM), Quadratic Discriminant Analysis (QDA), and Naïve Bayesian Classifier (NB).

According to yet further embodiments, the reactivity of the antibodies to the plurality of antigens in the sample obtained from a control subject is selected from the group consisting of reactivity of antibodies in multiple samples of control subjects, and a stored set of data from control subjects.

The term "plurality of antigens" as used herein refers to at least three antigens. According to still further embodiments, the reactivity of antibodies is determined to a plurality of antigens such as to at least 5 antigens, alternatively to at least 7 antigens, 10 antigens, 15 antigens, 20 antigens and any integer in between (e.g. at least 4, 6, 7, 8 or 9 antigens), or to more than 20 antigens. According to yet further embodiments, the plurality of antigens may comprise or consist of the entire antigens listed in a Table as disclosed herein.

According to additional embodiments, determining the reactivity of antibodies to a plurality of antigens selected from tables 1-12 can further include determining the reactivity of the antibodies to one or more additional antigens selected from any one of tables 16-28. Thus, reactivity of antigens can be determined to a plurality of antigens in Table 1, and optionally to one or more antigens in Table 16. Similarly, reactivity of antigens can be determined to a plurality of antigens in Table 8, and optionally to one or more antigens in Table 17, etc. Additionally or alternatively, the reactivity to one or more antigens selected from any one of tables 30-34 may be determined in certain embodiments, as detailed herein.

According to still further embodiments, the antigens are in the form of an antigen probe set, an antigen array, or an antigen chip.

According to further embodiments, the subject being diagnosed by the methods disclosed herein manifests inflammation and optionally at least one rheumatic symptom selected from the group consisting of: joint pain, joint stiffness, joint swelling, joint redness, joint tenderness, joint warmth, and loss of joint range of motion.

According to additional embodiments of the invention, the methods can further include treating the subject diagnosed as having the autoimmune disease with a disease-specific treatment.

According to further embodiments, the disease-specific treatment is selected from the group consisting of nonsteroidal anti-inflammatory drugs (NSAIDs), corticosteroids, glucocorticoids, immunosuppressants, hydroxychloroquine, cyclophosphamide, TNF-α inhibitors, chelating agents, endothelin receptor antagonist, PAH, PDE-5 inhibitors, gastrointestinal agents, immunomodulators, analgesics, anticoagulants, antiplatelet and other biologic medications.

According to still further embodiments, if the disease is RA, said disease-specific treatment is selected from the group consisting of Etanercept (Enbrel), Adalimumab (Humira), Infliximab (Remicade), Certolizumab pegol (Cimzia), Golimumab (Simponi), Anakinra (Kineret), Tocilizumab (Actemra), Tofacitinib (Xeljanz), and any combination thereof.

According to yet further embodiments, if the disease is SS, said disease-specific treatment is selected from the group consisting of pilocarpine (Salagen), cevimeline (Evoxac), cyclosporine (Restasis), and any combination thereof.

According to still further embodiments, if the disease is SLE, said disease-specific treatment is selected from the group consisting of NSAIDs, Ibuprofen, Naproxen, Prednisone, Methylprednisolone (A-Methapred, Medrol, Solu-Medrol, Depo-Medrol), Cellcept, Methotrexate, Imuran, mycophenolate mofetil, Abatacept, Arava, Immune globulin intravenous (Hizentra, Gammagard, Octagam, Privigen), Plaquenil, Myfortic, Endoxan, Cytoxan, Neosar, Procytox, Revimmune, Benilimumab (Benlysta), Rituximab, Cyclosporine (Gengraf, Neoral, Sandimmune).

According to yet further embodiments, if the disease is APS, said disease-specific treatment is selected from the group consisting of warfarin, rivaroxaban (Xarelto), dabigatran (Pradaxa), apixaban (Eliquis), edoxaban (Lixiana), heparin, aspirin, clopidogrel, Rituximab.

According to further embodiments, if disease is SSc, said disease-specific treatment is selected from the group consisting of Ibuprofen, Naproxen, Prednisone, Cellcept, Methotrexate, Imuran, Cytoxan, Rituximab, Penicillamine (Cuprimine, Depen), Bosentan (Tracleer), Ambrisentan (Letairis), Macitentan (Opsumit), Tadalafil (Adcirca), Sildenafil (Revatio).

According to some embodiments, the methods of diagnosing an autoimmune disease (including differential diagnosis) according to the principles of the invention can further include a step of identifying an antigen-specific treatment for the subject diagnosed as having an autoimmune disease, wherein the antigen is selected from the group consisting of the antigens listed in any one of Tables 1 to 12, and wherein the reactivity of antibodies in the sample obtained from said subject to said antigen is significantly different from the control reactivity pattern to said antigen.

According to additional embodiments, the disease-specific treatment is an inhibitor of an antibody to an antigen selected from the group consisting of the antigens listed in any one of Tables 1 to 12, wherein the reactivity of the antibody to the antigen in the sample obtained from said subject is significantly different from the reactivity of an antibody to said antigen in a sample obtained from a healthy control subject.

According to yet further embodiments, the antigen being identified for the antigen-specific treatment is selected from the antigens listed in Table 1. According to a certain embodiment, the antigen is LAIR-1. In another embodiment, the antigen is selected from the antigens listed in any one of Tables 1, 8-12, 16, 30 and 34. Each possibility represents a separate embodiment of the invention.

According to some embodiments of the invention, an antigen probe set is provided, including the antigens listed in at least one of Tables 1-12. According to other embodiments, the antigen probe set comprises the antigens listed in a Table as disclosed herein. Each possibility represents a separate embodiment of the invention.

According to further embodiments of the invention, an article of manufacture including the antigen probe set of the invention is provided.

According to some embodiments, the article of manufacture is in the form of an antigen probe set, an antigen array, or an antigen chip.

In another exemplary aspect, a method of diagnosing an autoimmune disease selected from the group consisting of systemic lupus erythematosus (SLE), rheumatoid arthritis (RA), scleroderma (SSc), Sjögren's Syndrome (SS), and anti-phospholipid syndrome (APS) in a subject comprises:

i. obtaining a sample from a subject suspected of having an autoimmune rheumatic disease due to inflammation and at least one rheumatic symptom selected from the group consisting of: joint pain, joint stiffness, joint swelling, joint redness, joint tenderness, joint warmth, and loss of joint range of motion;

ii. determining the reactivity of antibodies in the sample obtained from the subject to a plurality of antigens selected from Table 1, thereby obtaining a reactivity pattern of said sample to the plurality of antigens;

iii. comparing the reactivity pattern of said sample to a healthy control reactivity pattern to said plurality of antigens by a supervised classification algorithm, wherein a significantly different reactivity pattern of the sample obtained from the subject compared to the healthy control reactivity pattern indicates that said subject has an autoimmune rheumatic disease.

In another exemplary embodiment, the method further comprises identifying the autoimmune disease in said subject by the steps comprising:

iv. determining the reactivity of antibodies in the sample obtained from the subject to a plurality of antigens selected from at least one of Tables 8-12, thereby obtaining a reactivity pattern of said sample to the plurality of antigens;

v. comparing the reactivity pattern of said sample to a healthy control reactivity pattern to said plurality of antigens, by a supervised classification algorithm, wherein:

a significantly different reactivity pattern of the sample obtained from the subject to a plurality of antigens selected from Table 8 compared to the healthy control reactivity pattern indicates that said subject has SLE, a significantly different reactivity pattern of the sample obtained from the subject to a plurality of antigens selected from Table 9 compared to the healthy control reactivity pattern indicates that said subject has SSc, a significantly different reactivity pattern of the sample obtained from the subject to a plurality of antigens selected from Table 10 compared to the healthy control reactivity pattern indicates that said subject has APS, a significantly different reactivity pattern of the sample obtained from the subject to a plurality of antigens selected from Table 11 compared to the healthy control reactivity pattern indicates that said subject has SS, and/or a significantly different reactivity pattern of the sample obtained from the subject to a plurality of antigens selected from Table 12 compared to the healthy control reactivity pattern indicates that said subject has RA.

In another embodiment, the subject is suspected as having SLE or RA and the method comprises:

(a) determining the reactivity of antibodies in the sample obtained from the subject to a plurality of antigens selected from Table 2, thereby obtaining a reactivity pattern of said sample to the plurality of antigens selected from Table 2;

(b) comparing the reactivity pattern of said sample to the plurality of antigens selected from Table 2 to a control reactivity pattern to said plurality of antigens selected from Table 2 by a supervised classification algorithm, wherein the control is a RA control, and a significantly different reactivity pattern of the sample obtained from said subject compared to the RA control reactivity pattern indicates that said subject has SLE, and/or wherein the control is a SLE control, and a significantly different reactivity pattern of the sample obtained from said subject compared to the SLE control reactivity pattern indicates that said subject has RA;

or the subject is suspected as having SLE or SSc and the method comprises:

(a) determining the reactivity of antibodies in the sample obtained from the subject to a plurality of antigens selected from Table 3, thereby obtaining a reactivity pattern of said sample to the plurality of antigens;

(b) comparing the reactivity pattern of said sample obtained from the subject to the plurality of antigens selected from Table 3, to a control reactivity pattern to said plurality of antigens selected from Table 3 by a supervised classification algorithm, wherein the control is a SSc control, and a significantly different reactivity pattern of the sample obtained from said subject compared to the SSc control reactivity pattern indicates that said subject has SLE, and/or wherein the control is a SLE control, and a significantly different reactivity pattern of the sample obtained from said subject compared to the SLE control reactivity pattern indicates that said subject has SSc;

or the subject is suspected as having SLE or APS and the method comprises:

(a) determining the reactivity of antibodies in the sample obtained from the subject to a plurality of antigens selected from Table 4, thereby obtaining a reactivity pattern of said sample to the plurality of antigens;

(b) comparing the reactivity pattern of said sample obtained from the subject to the plurality of antigens selected from Table 4 to a control reactivity pattern to said plurality of antigens selected from Table 4 by a supervised classification algorithm, wherein the control is an APS control, and a significantly different reactivity pattern of the sample obtained from said subject compared to the APS control reactivity pattern indicates that said subject has SLE, and/or wherein the control is a SLE control, and a significantly different reactivity pattern of the sample obtained from said subject compared to the SLE control reactivity pattern indicates that said subject has APS;

or the subject is suspected as having SS or SSc and the method comprises:

(a) determining the reactivity of antibodies in the sample obtained from the subject to a plurality of antigens selected from Table 5, thereby obtaining a reactivity pattern of said sample to the plurality of antigens;

(b) comparing the reactivity pattern of said sample obtained from the subject to the plurality of antigens selected from Table 5 to a control reactivity pattern to said plurality of antigens selected from Table 5 by a supervised classification algorithm, wherein the control is a SSc control, and a significantly different reactivity pattern of the sample obtained from said subject compared to the SSc control reactivity pattern indicates that said subject has SS, and/or wherein the control is a SS control, and a significantly different reactivity pattern of the sample obtained from said subject compared to the SS control reactivity pattern indicates that said subject has SSc;

or the subject is suspected as having SS or RA and the method comprises:

(a) determining the reactivity of antibodies in the sample obtained from the subject to a plurality of antigens selected from Table 6, thereby obtaining a reactivity pattern of said sample to the plurality of antigens;

(b) comparing the reactivity pattern of said sample obtained from the subject to the plurality of antigens selected from Table 6 to a control reactivity pattern to said plurality of antigens selected from Table 6 by a supervised classification algorithm, wherein the control is a RA control, and a significantly different reactivity pattern of the sample obtained from said subject compared to the RA control reactivity pattern indicates that said subject has SS, and/or wherein the control is a SS control, and a significantly different reactivity pattern of the sample obtained from said subject compared to the SS control reactivity pattern indicates that said subject has RA;

or the subject is suspected as having SLE or SS and the method comprises:

(a) determining the reactivity of antibodies in the sample obtained from the subject to a plurality of antigens comprising the antigen of Table 7, thereby obtaining a reactivity pattern of said sample to the plurality of antigens;

(b) comparing the reactivity pattern of said sample obtained from the subject to the plurality of antigens to a control reactivity pattern to said plurality of antigens by a supervised classification algorithm, wherein the control is a SS control, and a significantly different reactivity pattern of the sample obtained from said subject compared to the SS control reactivity pattern indicates that said subject has SLE, and/or wherein the control is a SLE control, and a significantly different reactivity pattern of the sample obtained from said subject compared to the SLE control reactivity pattern indicates that said subject has SS.

In another embodiment the method further comprises treating said subject diagnosed as having the autoimmune disease with a disease-specific treatment. In various embodiments, the disease-specific treatment is selected from the group consisting of nonsteroidal anti-inflammatory drugs (NSAIDs), corticosteroids, glucocorticoids, immunosuppressants, hydroxychloroquine, cyclophosphamide, TNF-α inhibitors, chelating agents, endothelin receptor antagonist, PAH, PDE-5 inhibitors, gastrointestinal agents, immunomodulators, analgesics, anticoagulants, antiplatelet and other biologic medications. In other specific embodiments, said disease is RA and said disease-specific treatment is selected from the group consisting of Etanercept (Enbrel), Adalimumab (Humira), Infliximab (Remicade), Certolizumab pegol (Cimzia), Golimumab (Simponi), Anakinra (Kineret), Tocilizumab (Actemra), Tofacitinib (Xeljanz), and any combination thereof. In other specific embodiments, said disease is SS and said disease-specific treatment is selected from the group consisting of pilocarpine (Salagen), cevimeline (Evoxac), cyclosporine (Restasis), and any combination thereof. In other specific embodiments, said disease is SLE and said disease-specific treatment is selected from the group consisting of NSAIDs, Ibuprofen, Naproxen, Prednisone, Methylprednisolone (A-Methapred, Medrol, Solu-Medrol, Depo-Medrol), Cellcept, Methotrexate, Imuran, mycophenolate mofetil, Abatacept, Arava, Immune globulin intravenous (Hizentra, Gammagard, Octagam, Privigen), Plaquenil, Myfortic, Endoxan, Cytoxan, Neosar, Procytox, Revimmune, Benilimumab (Benlysta), Rituximab, Cyclosporine (Gengraf, Neoral, Sandimmune). In other specific embodiments, said disease is APS and said disease-specific treatment is selected from the group consisting of warfarin, rivaroxaban (Xarelto), dabigatran (Pradaxa), apixaban (Eliquis), edoxaban (Lixiana), heparin, aspirin, clopidogrel, Rituximab. In other specific embodiments, said disease is SSc and said disease-specific treatment is selected from the group consisting of Ibuprofen, Naproxen, Prednisone, Cellcept, Methotrexate, Imuran, Cytoxan, Rituximab, Penicillamine (Cuprimine, Depen), Bosentan (Tracleer), Ambrisentan (Letairis), Macitentan (Opsumit), Tadalafil (Adcirca), Sildenafil (Revatio).

In other embodiments, the sample is selected from the group consisting of a serum sample, a plasma sample, and a blood sample, and the reactivity of antibodies comprises IgM reactivity, IgG reactivity, or a combination thereof. In other embodiments, the supervised classification algorithm is selected from the group consisting of Support Vector Machine (SVM), Quadratic Discriminant Analysis (QDA), and Naïve Bayesian Classifier (NB). In other embodiments, the reactivity of the antibodies to the plurality of antigens in the sample obtained from a control subject is selected from the group consisting of reactivity of antibodies in multiple samples of control subjects, and a stored set of data from control subjects, and wherein the antigens are in the form of an antigen probe set, an antigen array, or an antigen chip.

In a particular embodiment, said plurality of antigens selected from Table 1 includes: LAIR1, MICA, RO60calf, CD62P, Ferritin, Chromatin, and CENPB.

In another exemplary aspect, a method of diagnosing an autoimmune disease selected from the group consisting of systemic lupus erythematosus (SLE), rheumatoid arthritis (RA), scleroderma (SSc), Sjogren's Syndrome (SS), and anti-phospholipid syndrome (APS) in a subject comprises:
 i. obtaining a sample from a subject suspected of having an autoimmune rheumatic disease;
 ii. determining the reactivity of antibodies in the sample obtained from the subject to a plurality of antigens selected from at least one of Tables 8-12, thereby obtaining a reactivity pattern of said sample to the plurality of antigens;
 iii. comparing the reactivity pattern of said sample to a healthy control reactivity pattern to said plurality of antigens, by a supervised classification algorithm,
 wherein:
 a significantly different reactivity pattern of the sample obtained from the subject to a plurality of antigens selected from Table 8 compared to the healthy control reactivity pattern indicates that said subject has SLE,
 a significantly different reactivity pattern of the sample obtained from the subject to a plurality of antigens selected from Table 9 compared to the healthy control reactivity pattern indicates that said subject has SSc,
 a significantly different reactivity pattern of the sample obtained from the subject to a plurality of antigens selected from Table 10 compared to the healthy control reactivity pattern indicates that said subject has APS,
 a significantly different reactivity pattern of the sample obtained from the subject to a plurality of antigens selected from Table 11 compared to the healthy control reactivity pattern indicates that said subject has SS, and/or a significantly different reactivity pattern of the sample obtained from the subject to a plurality of antigens selected from Table 12 compared to the healthy control reactivity pattern indicates that said subject has RA.

In another embodiment, the method further comprises identifying an antigen-specific treatment for said subject, wherein the antigen is selected from the group consisting of the antigens listed in any one of Tables 1 to 12, and the reactivity of antibodies in the sample obtained from said subject to said antigen is significantly different from the control reactivity pattern to said antigen. In other specific embodiments, the disease-specific treatment is an inhibitor of an antibody to an antigen selected from the group consisting of the antigens listed in any one of Tables 1 to 12, wherein the reactivity of the antibody to the antigen in the sample obtained from said subject is significantly different from the reactivity of an antibody to said antigen in a sample obtained from a healthy control subject. In a particular embodiment the antigen is selected from Table 1, preferably the antigen is LAIR-1.

In another exemplary aspect, a method for differentially diagnosing an autoimmune disease comprises:
  i. obtaining a sample from a subject diagnosed as having the autoimmune disease;
  ii. contacting the sample, under conditions such that a specific antigen-antibody complex is formed, with antigens selected from at least one of Tables 2-7;
  iii. determining the reactivity of antibodies in said sample to the antigens, thereby determining the reactivity pattern of said sample to said antigens; and
  iv. comparing the reactivity pattern of said sample obtained from the subject to a control reactivity pattern to said antigens by a supervised classification algorithm,
wherein:
a significantly different reactivity pattern of the sample obtained from the subject to a plurality of antigens selected from Table 2 compared to a RA control reactivity pattern to said antigens indicates that said subject has SLE, a significantly different reactivity pattern of the sample obtained from said subject to a plurality of antigens selected from Table 2 compared to a SLE control reactivity pattern to said antigens indicates that said subject has RA, a significantly different reactivity pattern of the sample obtained from said subject to a plurality of antigens selected from Table 3 compared to a SSc control reactivity pattern to said antigens indicates that said subject has SLE, a significantly different reactivity pattern of the sample obtained from said subject to a plurality of antigens selected from Table 3 compared to a SLE control reactivity pattern to said antigens indicates that said subject has SSc, a significantly different reactivity pattern of the sample obtained from said subject to a plurality of antigens selected from Table 4 compared to an APS control reactivity pattern to said antigens indicates that said subject has SLE, a significantly different reactivity pattern of the sample obtained from said subject to a plurality of antigens selected from Table 4 compared to an SLE control reactivity pattern to said antigens indicates that said subject has APS, a significantly different reactivity pattern of the sample obtained from said subject to a plurality of antigens selected from Table 5 compared to a SSc control reactivity pattern to said antigens indicates that said subject has SS, a significantly different reactivity pattern of the sample obtained from said subject to a plurality of antigens selected from Table 5 compared to a SS control reactivity pattern to said antigens indicates that said subject has SSc, a significantly different reactivity pattern of the sample obtained from said subject to a plurality of antigens selected from Table 6 compared to a RA control reactivity pattern to said antigens indicates that said subject has SS, a significantly different reactivity pattern of the sample obtained from said subject to a plurality of antigens selected from Table 6 compared to a SS control reactivity pattern indicates that said subject has RA, a significantly different reactivity pattern of the sample obtained from said subject to a plurality of antigens comprising the antigen of Table 7 compared to a SS control reactivity pattern to said antigens indicates that said subject has SLE, and/or a significantly different reactivity pattern of the sample obtained from said subject to a plurality of antigens comprising the antigen of Table 7 compared to a SLE control reactivity pattern indicates that said subject has SS.

In another embodiment, the method further comprises identifying an antigen-specific treatment for said subject, wherein the antigen is selected from the group consisting of the antigens listed in any one of Tables 1 to 12, and the reactivity of antibodies in the sample obtained from said subject to said antigen is significantly different from the control reactivity pattern to said antigen. In other specific embodiments, the disease-specific treatment is an inhibitor of an antibody to an antigen selected from the group consisting of the antigens listed in any one of Tables 1 to 12, wherein the reactivity of the antibody to the antigen in the sample obtained from said subject is significantly different from the reactivity of an antibody to said antigen in a sample obtained from a healthy control subject. In a particular embodiment the antigen is selected from Table 1, preferably the antigen is LAIR-1.

Other objects, features and advantages of the invention will become clear from the following description and drawings.

DETAILED DESCRIPTION OF THE DRAWINGS

FIG. 1 shows Table 15, listing exemplary antigens to be used in embodiments of the invention.

DETAILED DESCRIPTION OF THE INVENTION

Provided are assays and methods for diagnosis of an autoimmune disease in a subject, and particularly identifying the specific autoimmune disease, namely systemic lupus erythematosus (SLE), rheumatoid arthritis (RA), scleroderma (SSc), Sjögren's syndrome (SS), or anti-phospholipid syndrome (APS) in a subject. As conventional methods, such as symptom-profiling, e.g., inflammation, joint pains, joint swelling, frequently correlate with a plurality of medically-relevant diseases and as such are not sufficient to identify a specific autoimmune disease, embodiments of the invention provide accurate means for such identification.

According to some embodiments of the invention, an antibody-containing sample is obtained from a subject in order to diagnose whether the subject has an autoimmune disease. Next, the antibodies are allowed to form complexes with a plurality of pre-determined antigens. The reactivity of the antibodies of the subject to the plurality of pre-determined antigens is then evaluated so as to form a reactivity pattern which is then compared to the reactivity of antibodies of healthy control subjects towards the same three antigens. The similarity and/or difference between the reactivity pattern of the subject's antibodies and the control antibodies towards the antigens is then used to diagnose whether the subject has an autoimmune disease. Exemplary antigens to be used in embodiments of the invention are listed in Table 15 herein.

Methods and assays constructed according to the principles of the invention further provide differential diagnosis between different autoimmune diseases such as SLE, SS, RA, SSc and APS. According to some embodiments of the invention, an antibody-containing sample is obtained from a subject in order to differentially diagnose between autoimmune diseases, such as between SLE and RA, or between SLE and SS, between SLE and SSc, between RA and SSc, between RA and SC, between SSc and APS, etc. Next, the antibodies are allowed to form complexes with at least three pre-determined antigens listed in the respective Tables 2-7. The reactivity of the antibodies of the subject to the antigens is then evaluated so as to form a reactivity pattern which is then compared to the reactivity of the antibodies of control samples, i.e. samples obtained from other subjects having a specific autoimmune disease, e.g., RA, SSc, SS or APS, towards the same antigens. The similarity and/or difference between the reactivity pattern of the subject's antibodies and the control antibodies towards the antigens is then used to differentially diagnose the subject. The antibodies being tested by the present methods can be of the IgG isotype or the IgM isotype, although any other isotype can be tested as well.

Comparing reactivity patterns can be performed using suitable classifiers or algorithms, including, but not limited to, learning and pattern recognition algorithms, supervised classifiers, and the like. A significant difference from control reactivities, such as from a healthy control as disclosed herein, may typically and conveniently be performed considering the respective values of both negative and positive control groups (e.g. healthy control subjects and autoimmune rheumatic diseased patients, respectively). The methods according to embodiments of the invention may include a step of determining the respective reactivity values to the test antigens in positive and/or negative control samples, or may employ comparison of the values measured in the test sample to the respective predetermined values or stored data. The test sample may thereby be classified as corresponding to (substantially similar to, or not substantially different from) either the positive or negative control group (e.g. health control or autoimmune disease), as disclosed herein. The positive and negative controls referred to herein typically and conveniently represent control sets, such as a panel of control samples from a set of similarly-diagnosed individuals, or a stored set of data obtained from similarly-diagnosed individuals.

It should therefore be noted that the step of identifying the subject as being afflicted with a specific disease, e.g. SLE, RA, SSc, SS, or APS can alternatively and/or additionally include a step of identifying the subject as having said disease, based on a significant similarity in the reactivity pattern of said sample compared to the reactivity pattern of an SLE, RA, SSc, SS, or APS control sample set. This can conveniently be done by detecting the similarity in the reactivity pattern of said sample compared to the reactivity pattern of a specific disease set (e.g. SLE, RA, SSc, SS, and/or APS).

In other embodiments of the invention, methods are provided for treatment of the diagnosed autoimmune disease including autoimmune rheumatic disorder. It is known that while certain therapeutic agents show some efficacy in a number of autoimmune rheumatic disorders, other therapeutic agents are specific for a particular disorder (e.g. RA, SLE or SS), and/or may be harmful when administered to subjects having other diseases. In addition, early diagnosis and initiation of therapy have proven to prevent disease progression and reduce morbidity. Additionally, certain dosage adjustments may be disease-specific, and accurate early diagnosis may ensure a fast onset of an effective treatment regimen.

According to some embodiments, the sample obtained from the subject can be an antibody-containing fluid sample, including, but not limited to, a blood derived sample (e.g. serum, plasma and whole blood). In certain embodiments, the sample may be processed prior to contacting with the antigens, e.g. by dilution, antibody purification and the like.

According to additional embodiments, the antigens are arranged on the surface of a solid support, typically a planar support such as a chemically activated glass support. In a particular embodiment, the support is planar glass support coated with an epoxy silane organic layer. Conveniently, the antigens are arranged in the form of an antigen array.

In other embodiments, the reactivity of the antibodies may be determined by various immunoassays enabling quantitative measurement of antigen-antibody binding, which may be subjected to image analysis and data analysis steps. For example, without limitation, images acquired by fluorescent scanning of fluorescently-labeled antibodies bound onto an antigen array may be pre-processed by methods including one or more of the following steps:

Determining representation of each spot through subtraction of background intensity from the foreground intensity; imputing negative values with low intensity spots, as negative spots has no meaning in the context of our platform; performing log transformation on each spot and combining spot replicates per array, wherein outliers spots may be removed based on Grubb's test; adjusting the mean per array per channel, wherein the mean per array may be calculated based on a set of antigens per channel, and the mean may then be adjusted against a constant value and the correction is applied to all antigens; and correcting for print lot and test session effect using reference sera, wherein the correction may be performed per test session per print lot, by subtraction of reference serum intensities from corresponding antigens in order to express all intensities as relative to the reference serum.

Advantageously, methods according to embodiments of the invention may employ the use of learning and pattern recognition analyzers, clustering algorithms and the like, in order to discriminate between reactivity patterns of control subjects to control sets of patients having autoimmune diseases such as RA, SLE, SSC, SS or APS. As such, this term specifically includes a difference measured by, for example, determining the reactivity of antibodies in a test sample to a plurality of antigens, and comparing the resulting reactivity pattern to the reactivity patterns of negative and positive control samples (e.g. samples obtained from healthy control subjects or patients afflicted with a specific disease, respectively) using such algorithms and/or analyzers. The difference may also be measured by comparing the reactivity pattern of the test sample to a predetermined classification rule obtained in such manner.

According to one aspect of the invention, methods are provided for detecting an autoimmune disease in a subject, the method including:
  i. obtaining a sample from the subject;
  ii. contacting the sample with a plurality of antigens selected from Table 1, under conditions such that a specific antigen-antibody complex may be formed for each antigen, and quantifying the amount of antigen-antibody complex formed for each antigen to generate a reactivity pattern of said sample to the plurality of antigens;

iii. comparing the reactivity pattern of said sample to a healthy control reactivity pattern to said plurality of antigens by a supervised classification algorithm, and iv. detecting the autoimmune disease by quantifying whether the reactivity pattern of the sample obtained from the subject is significantly different from the healthy control reactivity pattern, wherein a significantly different reactivity pattern of the sample obtained from the subject compared to the healthy control reactivity pattern indicates that said subject has an autoimmune rheumatic disease.

According to some embodiments, the autoimmune disease to be diagnosed is selected from the group consisting of SLE, RA, SSc, SS, and APS.

According to additional embodiments, if the subject has been diagnosed by the above method as having an autoimmune disease, the method can further include identifying the autoimmune disease in said subject by the steps including:

v. determining the reactivity of antibodies in the sample obtained from the subject to a plurality of antigens selected from at least one of Tables 8-12, thereby obtaining a reactivity pattern of said sample to the plurality of antigens;

vi. comparing the reactivity pattern of said sample to a healthy control reactivity pattern to said plurality of antigens, by a supervised classification algorithm, wherein:

a significantly different reactivity pattern of the sample obtained from the subject to a plurality of antigens selected from Table 8 compared to the healthy control reactivity pattern indicates that said subject has SLE, a significantly different reactivity pattern of the sample obtained from the subject to a plurality of antigens selected from Table 9 compared to the healthy control reactivity pattern indicates that said subject has SSc, a significantly different reactivity pattern of the sample obtained from the subject to a plurality of antigens selected from Table 10 compared to the healthy control reactivity pattern indicates that said subject has APS, a significantly different reactivity pattern of the sample obtained from the subject to a plurality of antigens selected from Table 11 compared to the healthy control reactivity pattern indicates that said subject has SS, and/or a significantly different reactivity pattern of the sample obtained from the subject to a plurality of antigens selected from Table 12 compared to the healthy control reactivity pattern indicates that said subject has RA.

According to another aspect of the invention, methods are provided for detecting an autoimmune disease selected from the group consisting of SLE, RA, SSc, SS, and APS in a subject, the method may include:

i. obtaining a sample from a subject suspected of having an autoimmune rheumatic disease;

ii. contacting the sample with a plurality of antigens selected from at least one of Tables 8-12 under conditions such that a specific antigen-antibody complex may be formed for each antigen, and quantifying the amount of antigen-antibody complex formed for each antigen to generate a reactivity pattern of said sample to the plurality of antigens;

iii. comparing the reactivity pattern of said sample to a healthy control reactivity pattern to said plurality of antigens, by a supervised classification algorithm, and iv. detecting the autoimmune disease by quantifying whether the reactivity pattern of the sample obtained from the subject is significantly different from the healthy control reactivity pattern wherein:

a significantly different reactivity pattern of the sample obtained from the subject to a plurality of antigens selected from Table 8 compared to the healthy control reactivity pattern indicates that said subject has SLE, a significantly different reactivity pattern of the sample obtained from the subject to a plurality of antigens selected from Table 9 compared to the healthy control reactivity pattern indicates that said subject has SSc, a significantly different reactivity pattern of the sample obtained from the subject to a plurality of antigens selected from Table 10 compared to the healthy control reactivity pattern indicates that said subject has APS, a significantly different reactivity pattern of the sample obtained from the subject to a plurality of antigens selected from Table 11 compared to the healthy control reactivity pattern indicates that said subject has SS, and/or a significantly different reactivity pattern of the sample obtained from the subject to a plurality of antigens selected from Table 12 compared to the healthy control reactivity pattern indicates that said subject has RA.

According to another aspect of the invention, methods are provided for detecting an autoimmune disease, including:

(v) obtaining a sample from a subject diagnosed as having the autoimmune disease;

(vi) contacting the sample with antigens selected from at least one of Tables 2-7, under conditions such that a specific antigen-antibody complex is formed for each antigen, and quantifying the amount of antigen-antibody complex formed for each antigen to generate a reactivity pattern of said sample to the plurality of antigens;

(vii) comparing the reactivity pattern of said sample obtained from the subject to a control reactivity pattern to said antigens by a supervised classification algorithm, and (viii) detecting the autoimmune disease by quantifying whether the reactivity pattern of the sample obtained from the subject is significantly different from the control reactivity pattern, wherein:

a significantly different reactivity pattern of the sample obtained from the subject to a plurality of antigens selected from Table 2 compared to a RA control reactivity pattern to said antigens indicates that said subject has SLE, a significantly different reactivity pattern of the sample obtained from said subject to a plurality of antigens selected from Table 2 compared to a SLE control reactivity pattern to said antigens indicates that said subject has RA, a significantly different reactivity pattern of the sample obtained from said subject to a plurality of antigens selected from Table 3 compared to a SSc control reactivity pattern to said antigens indicates that said subject has SLE, a significantly different reactivity pattern of the sample obtained from said subject to a plurality of antigens selected from Table 3 compared to a SLE control reactivity pattern to said antigens indicates that said subject has SSc, a significantly different reactivity pattern of the sample obtained from said subject to a plurality of antigens selected from Table 4 compared to an APS control reactivity pattern to said antigens indicates that said subject has SLE, a significantly different reactivity pattern of the sample obtained from said subject to a plurality of antigens selected from Table 4 compared to an SLE control reactivity pattern to said antigens indicates that said subject has APS, a significantly different reactivity pattern of the sample obtained from said subject to a plurality of antigens selected from Table 5 compared to a SSc control reactivity pattern to said antigens indicates that said subject has SS, a significantly different reactivity pattern of the sample obtained from said subject to a plurality of antigens selected from Table 5 compared to a SS control reactivity pattern to said antigens indicates that said subject has SSc, a significantly different reactivity pattern of the sample obtained from said subject to a plurality of antigens selected from Table 6 compared to a RA control reactivity pattern to said antigens indicates that said subject has SS, and/or a significantly different reactivity pattern of the sample obtained from said subject to a plurality of antigens selected from Table 6 compared to a SS control reactivity pattern indicates that said subject has RA.

a significantly different reactivity pattern of the sample obtained from said subject to a plurality of antigens selected from Table 7 compared to a SS control reactivity pattern to said antigens indicates that said subject has SLE, and/or a significantly different reactivity pattern of the sample obtained from said subject to a plurality of antigens selected from Table 7 compared to a SLE control reactivity pattern indicates that said subject has SS.

Subjects and Autoimmune Diseases

Subjects to be diagnosed by the methods according to the principles of the invention are suspected of having an autoimmune disease, such as an autoimmune rheumatic disorder (ARD).

SLE patients usually display at least one, and in the majority of cases several, of the following symptoms: painful, pale or purple fingers or toes triggered by cold temperature or emotional stress (Raynaud's phenomenon), joint pain, joint stiffness, joint swelling, joint redness, joint tenderness, joint warmth, loss of joint range of motion, fatigue, muscle pain, vasculitis (inflammation of blood vessels), dry eyes, dry mouth, and inflammation (determined by C-reactive protein (CRP), erythrocyte sedimentation rate (ESR) tests).

RA patients usually display at least one, and in the majority of cases several, of the following symptoms: painful, pale or purple fingers or toes triggered by cold temperature or emotional stress (Raynaud's phenomenon), joint pain, joint stiffness, joint swelling, joint redness, joint tenderness, joint warmth, loss of joint range of motion, fatigue, vasculitis (inflammation of blood vessels), dry eyes, dry mouth, inflammation (determined by C-reactive protein (CRP), erythrocyte sedimentation rate (ESR) tests), fever, anemia, and shortness of breath/lung involvement.

SS patients usually display at least one, and in the majority of cases several, of the following symptoms: painful, pale or purple fingers or toes triggered by cold temperature or emotional stress (Raynaud's phenomenon), joint pain, joint stiffness, joint swelling, joint redness, joint tenderness, joint warmth, loss of joint range of motion, fatigue, muscle pain, vasculitis (inflammation of blood vessels), dry eyes, dry mouth, fever, anemia, shortness of breath/lung involvement and inflammation (determined by C-reactive protein (CRP), erythrocyte sedimentation rate (ESR) tests).

SSc patients display one or more of the following symptoms: skin thickening, stiffness, poor blood flow to the fingers or toes with cold exposure, fatigue, areas of dilated small blood vessels, and weight loss.

APS patients display one or more of the following symptoms: blood clots (thrombosis) in arteries and/or veins, pregnancy-related complications such as miscarriage, stillbirth, preterm delivery, and severe preeclampsia.

According to embodiments of the invention, the patient population to be diagnosed and optionally treated by the methods of the invention includes subjects displaying inflammation and optionally at least one rheumatic symptom, e.g. joint pain, joint stiffness, joint swelling, joint redness, joint tenderness, joint warmth, and loss of joint range of motion. According to particular embodiments, the methods include a step of obtaining or deriving a sample from a subject suspected of having an autoimmune rheumatic disease due to inflammation and at least one rheumatic symptom selected from the group consisting of: joint pain, joint stiffness, joint swelling, joint redness, joint tenderness, joint warmth, and loss of joint range of motion. The methods of the invention allow for early and effective diagnosis and selection of appropriate treatment for a subject while minimizing undue trial and error, associated with existing methods based on e.g. clinical symptom evaluation.

Antibodies, Samples and Immunoassays

In some embodiments of the invention, the methods are preceded by a step of obtaining a sample from the subject. In certain embodiments, the sample is obtained from the subject by non-invasive means or methods.

According to additional embodiments of the invention, the sample obtained from the subject is a biological fluid. According to some embodiments, the sample is selected from the group consisting of plasma, serum, blood, cerebrospinal fluid, synovial fluid, sputum, urine, saliva, tears, lymph specimen, or any other antigen-containing biological fluid known in the art. Each possibility represents a separate embodiment of the invention. According to one embodiment, the sample is a serum sample. In certain embodiments, the sample is obtained or derived from the subject by non-invasive means or methods.

According to some embodiments of the invention, the control sample is selected from the group consisting of a sample from at least one healthy individual, a panel of control samples from a set of healthy individuals, and a stored set of data obtained from healthy individuals. Each possibility represents a separate embodiment of the invention.

According to additional embodiments of the invention, the control sample is selected from the group consisting of a sample from at least one diagnosed individual, a panel of control samples from a set of similarly-diagnosed individuals, and a stored set of data obtained from similarly-diagnosed individuals. Each possibility represents a separate embodiment of the invention. Typically, a diagnosed individual is a subject afflicted with an autoimmune disease such as SLE (or any other form of lupus), RA, SSc, APS or SS.

According to further embodiments, the method comprises determining the reactivity of antibodies in the sample to a plurality of antigens (e.g. peptide, protein, lipid and/or nucleotide antigens as disclosed herein). According to some embodiments, the plurality of antigens is in one of the following forms: an antigen probe set, an antigen probe array, an antigen chip, dipstick, a lateral flow test, an ELISA plate, or in any other form known to those skilled in the art.

In certain embodiments, the plurality of antigens is in the form of a kit which further includes means for determining the reactivity of antibodies in a sample to a plurality of antigens. According to some embodiments, the kit further includes means for comparing reactivity of antibodies in different samples to a plurality of antigens. According to another embodiment, the kit further includes instructions for use of the kit for diagnosing whether a subject is afflicted with an autoimmune disease such as an ARD or for differentially diagnosing a specific autoimmune disease, e.g., SLE, RA, SSc, SS or APS.

According to another aspect, there is provided use of plurality of antigens described above for the preparation of a diagnostic kit for diagnosing whether a subject has an autoimmune disease, or for differentially diagnosing SLE, SS, RA, APS or SSc in a subject. Each possibility represents a separate embodiment of the invention. The diagnostic kit is, in some embodiments, useful for determining the reactivity of antibodies in a sample, thereby determining the reactivity pattern of the sample to plurality of antigens.

As used herein, the "reactivity of antibodies in a sample to a plurality of antigens" refers to the immune reactivity of each antibody in the sample to at least three specific antigens selected from a plurality of antigens. The immune reactivity of the antibody to the antigen, i.e. its ability to specifically bind the antigen, can be used to determine the amount of the antibody in the sample. The calculated levels of each one of the tested antibodies in the sample are selectively referred to as the reactivity pattern of the sample to these antigens.

An antibody "directed to" an antigen, as used herein is an antibody which is capable of specifically binding the antigen.

It should be understood that when the terms "antibody" or "antibodies" are used, this is intended to include intact antibodies, such as polyclonal antibodies or monoclonal antibodies (mAbs), as well as proteolytic fragments thereof such as the Fab or F(ab')2 fragments. Further included within the scope of the invention are chimeric antibodies; recombinant and engineered antibodies, and fragments thereof.

Exemplary functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

The term "antigen" as used herein is a molecule or a portion of a molecule capable of being bound by an antibody. The antigen is typically capable of inducing an animal to produce antibody capable of binding to an epitope of that antigen. An antigen may have one or more epitopes. The specific reaction referred to above is meant to indicate that the antigen will react, in a highly selective manner, with its corresponding antibody and not with the multitude of other antibodies which may be evoked by other antigens. An "antigenic peptide" or an "antigenic oligonucleotide" is a peptide or an oligonucleotide, respectively, which is capable of specifically binding an antibody.

In some embodiments, detection of the capacity of an antibody to specifically bind an antigen probe may be performed by quantifying specific antigen-antibody complex formation. The term "specifically bind" as used herein means that the binding of an antibody to an antigen probe is not competitively inhibited by the presence of non-related molecules.

In accordance with the principles of the invention, any suitable immunoassay can be used with the antigens. Such techniques are well known to the ordinarily skilled artisan and have been described in many standard immunology manuals and texts. In certain preferable embodiments, determining the capacity of the antibodies to specifically bind the antigen probes is performed using an antigen probe array-based method. Preferably, the array is incubated with suitably diluted serum sample of the subject (e.g. diluted 1:10) so as to allow specific binding between the antibodies contained in the diluted serum sample and the immobilized antigen probes, washing out unbound serum from the array, incubating the washed array with a detectable label-conjugated antibodies of the desired isotype, washing out unbound label from the array, and measuring levels of the label bound to each antigen probe.

In other embodiments, various immunoassays may be used, including, without limitation, enzyme-linked immunosorbent assay (ELISA), flow cytometry with multiplex beads (such as the system made by Luminex), surface plasmon resonance (SPR), elipsometry, and various other immunoassays which employ, for example, laser scanning, light detecting, photon detecting via a photo-multiplier, photographing with a digital camera based system or video system, radiation counting, fluorescence detecting, magnetic detecting and any other system that allows quantitative measurement of antigen-antibody binding.

Various methods have been developed for preparing arrays suitable for the methods of the invention. State-of-the-art methods involve using a robotic apparatus to apply or "spot" distinct solutions containing antigen probes to closely spaced specific addressable locations on the surface of a planar support, typically a glass support, such as a microscope slide, which is subsequently processed by suitable thermal and/or chemical treatment to attach antigen probes to the surface of the support. Suitable supports may also include silicon, nitrocellulose, paper, cellulosic supports and the like.

Preferably, each antigen probe, or distinct subset of antigen probes that may be used in embodiments of the invention, which is attached to a specific addressable location of the array, is attached independently to at least two, more preferably to at least three separate specific addressable locations of the array in order to enable generation of statistically robust data.

In addition to antigen probes, the array may advantageously include control antigen probes or other standard chemicals. Such control antigen probes may include normalization control probes. The signals obtained from the normalization control probes provide a control for variations in binding conditions, label intensity, "reading" efficiency and other factors that may cause the signal of a given antibody-antigen probe interaction to vary. For example, signals, such as fluorescence intensity, read from all other antigen probes of the antigen probe array are divided or subtracted or shifted according to difference in mean intensities by the signal (e.g., fluorescence intensity) from the normalization control probes thereby normalizing the measurements. Normalization control probes can be bound to various addressable locations on the antigen probe array to control for spatial variation in antibody-antigen probe efficiency. Normalization control probes can be located at the corners or edges of the array to control for edge effects, as well as in the middle of the array.

The labeled antibodies or the ligand antibodies or the secondary antibodies may be of any of various suitable types of antibodies. Preferably, the secondary antibody is an antibody which is capable of specifically binding the Fc portion of the antibodies of the subject used. For example, where the antibodies of the subject are of the IgG isotype, the secondary antibody is preferably an antibody capable of specifically binding to the Fc region of IgG antibodies of the subject.

The secondary antibodies may be conjugated to any of various types of detectable labels. Preferably the label is a fluorophore, most preferably Cy3. Alternately, the fluorophore may be any of various fluorophores, including Cy5, fluorescein isothiocyanate (FITC), phycoerythrin (PE), rhodamine, Texas red, and the like. Suitable fluorophore-conjugated antibodies specific for antibodies of a specific isotype are widely available from commercial suppliers and methods of their production are well established.

Antibodies of the subject may be isolated for analysis of their antigen probe binding capacity in any of various ways, depending on the application and purpose. While the subject's antibodies may be suitably and conveniently in the form of blood serum or plasma or a dilution thereof (e.g., 1:10 dilution), the antibodies may be subjected to any desired degree of purification prior to being tested for their capacity to specifically bind antigen probes. The method of the invention may be practiced using whole antibodies of the subject, or antibody fragments of the subject which comprises an antibody variable region.

Diagnostic Methods

As disclosed herein, diagnostic methods according to the invention may generally include:
  i. obtaining a sample from a subject;
  ii. determining the reactivity of antibodies in the sample obtained from said subject to a plurality of antigens comprising one or more antigens selected from a Table as disclosed herein, thereby obtaining a reactivity pattern of said sample to the plurality of antigens;
  comparing the reactivity pattern of said sample to a control reactivity pattern to said plurality of antigens by a supervised classification algorithm.

In various exemplary embodiments, Tables 1, 16 and 30 disclose antigens for differentiating between autoimmune rheumatic diseased patients and healthy control (HC) subjects; Tables 2, 25 and 31 disclose antigens for differentiating between SLE patients and RA patients; Tables 3, 22 and 32 disclose antigens for differentiating between SLE patients and SSc patients; Tables 4 and 23 disclose antigens for differentiating between SLE patients and APS patients; Tables 5 and 26 discloses antigens for differentiating between SS patients and SSc patients; Tables 6 and 28 disclose antigens for differentiating between SS patients and RA patients; Tables 7 and 24 disclose antigens for differentiating between SLE patients and SS patients; Tables 8, 17 and 34 disclose antigens for differentiating between SLE patients and HC subjects; Tables 9 and 18 disclose antigens for differentiating between SSc patients and HC subjects; Tables 10 and 19 disclose antigens for differentiating between APS patients and HC subjects; Tables 11 and 20 disclose antigens for differentiating between SS patients and HC subjects; Tables 12 and 21 disclose antigens for differentiating between RA patients and HC subjects; Table 27 disclose antigen for differentiating between. APS and SS patients; and Table 33 disclose antigen for differentiating between SSc patients and RA patients.

According to certain embodiments, advantageous antigens for differentiating between autoimmune rheumatic diseased patients and HC subjects include LAIR1, MICA, RO60calf, CD62P, Ferritin, Chromatin, and CENPB. In other embodiments, advantageous antigens for differentiating between SLE patients and RA patients include DLST, RNPsm, RO60calf, H1 and RPP0.

In a particular embodiment, the plurality of antigens used in methods of the invention include LAIR1. In another embodiment, said plurality of antigens do not include LAIR1.

Methods of Treatment

The invention provides methods for treating a subject diagnosed as having a specific autoimmune disease including ARD with at least one autoimmune disease-specific treatment. Exemplary methods of the invention allow for early and effective selection of appropriate treatment for a subject suspected of having an ARD, while minimizing undue trial and error, thereby minimizing both suffering for the patient and therapeutic costs alike.

In some embodiments, the SLE-specific treatment is selected from the group consisting of NSAIDs, Ibuprofen, Naproxen, Prednisone, Methylprednisolone (A-Methapred, Medrol, Solu-Medrol, Depo-Medrol), Cellcept, Methotrexate, Imuran, mycophenolate mofetil, Abatacept, Arava, Immune globulin intravenous (Hizentra, Gammagard, Octagam, Privigen), Plaquenil, Myfortic, Endoxan, Cytoxan, Neosar, Procytox, Revimmune, Benilimumab (Benlysta), Rituximab, Cyclosporine (Gengraf, Neoral, Sandimmune).

In additional embodiments, the RA-specific treatment is selected from the group consisting of Etanercept (Enbrel®), Adalimumab (Humira®), Infliximab (Remicade®), Certolizumab pegol (Cimzia®), Golimumab (Simponi®), Anakinra (Kineret®), Tocilizumab (Actemra®), Tofacitinib (Xeljanz®), and any combination thereof. Each possibility represents a separate embodiment of the invention.

In further embodiments, the SS-specific treatment is selected from the group consisting of pilocarpine (Salagen®), cevimeline (Evoxac®), cyclosporine (Restasis®), and any combination thereof. Each possibility represents a separate embodiment of the invention.

In yet further embodiments, the SSc-specific treatment is selected from the group consisting of Ibuprofen, Naproxen, Prednisone, Cellcept, Methotrexate, Imuran, Cytoxan, Rituximab, Penicillamine (Cuprimine, Depen), Bosentan (Tracleer), Ambrisentan (Letairis), Macitentan (Opsumit), Tadalafil (Adcirca), Sildenafil (Revatio).

In still further embodiments, the APS-specific treatment is selected from the group consisting of warfarin, rivaroxaban (Xarelto), dabigatran (Pradaxa), apixaban (Eliquis), edoxaban (Lixiana), heparin, aspirin, clopidogrel, Rituximab.

Doses and treatment regimens for disease-specific treatments e.g. as listed above are known in the art and may be determined and adjusted by the skilled artisan (e.g. treating physician) according to the patient's characteristics and disease manifestations. For example, NSAIDs inhibit the generation of prostaglandins by blocking cyclooxygenase enzymes, COX-1 and COX-2. The major effect of these agents is to reduce acute inflammation thereby decreasing pain and improving function. All of these drugs also have mild to moderate analgesic properties independent of their anti-inflammatory effect. There are a large number of NSAIDs, some over the counter including ibuprofen (Advil®, Motrin®, Nuprin®) and naproxen (Aleve®) and many others are available by prescription including meloxicam (Mobic®), etodolac (Lodine®), nabumetone (Relafen®), sulindac (Clinoril®), tolementin (Tolectin®), choline magnesium salicylate (Trilasate®), diclofenac (Cataflam®, Voltaren®, Arthrotec®), diflusinal (Dolobid®), indomethacin (Indocin®), ketoprofen (Orudis®, Oruvail®), meloxicam (Mobic®), oxaprozin (Daypro®), and piroxicam (Feldene®). Longer acting NSAIDs that allow daily or twice daily dosing may improve compliance. The NSAID class also includes drugs known as COX-2 inhibitors that are also effective in controlling inflammation, e.g. celecoxib, Celebrex®; etoricoxib, Arcoxia®; lumiracoxib, Prexige®. These drugs were designed to decrease the gastrointestinal risk of NSAIDS, but concerns of possible increases in cardiovascular risk with these agents has led to the withdrawal of two of these drugs from the market (rofecoxib, Vioxx®; valdecoxib, Bextra®). NSAID doses for the treatment of SLE are known in the art. For example, ibuprofen may be used as needed or in doses up to 3000 mg a day, and naproxen is typically used as 500 mg twice a day.

Corticosteroids (such as prednisone; methylprednisolone, Medrol®) have both anti-inflammatory and immunoregulatory activity. They can be given orally, intravenously, intramuscularly or can be injected directly into the joint. In mild SLE, prednisolone is given in doses starting at 0.1-0.3 mg/kg/day followed by a gradual tapering dose regimen according to clinical response. The dose rises to 0.4-0.6 mg/kg/day in moderate disease and as high as 0.7-1.5 mg/kg/day in very severe disease. At such high doses, pulse therapy with intravenous (IV) methylprednisolone (MP; 500-1000 mg on one to three occasions) is deemed by many physicians to be safer with fewer associated side effects. IV therapy is considered in patients that have not responded to oral therapy and/or have serious manifestations of SLE such as lupus nephritis, neuropsychiatric disease, severe refractory thrombocytopenia, hemolytic anemia, severe vasculitis and cardiopulmonary disease.

Azathioprine (Imuran®) is an immunosuppressive agent commonly used for the induction of remission and as a steroid-sparing agent in mild-to-moderate disease. It works by affecting cell-mediated and humoral immune responses via the inhibition of lymphocyte proliferation, reduction in antibody production and suppression of natural killer cell activity. In severe disease, it is used as maintenance therapy and data from lupus nephritis trials show significant improvement in disease activity following induction therapy with cyclophosphamide or mycophenolate mofetil.

Other biological agents and immunomodulators include for example monoclonal antibodies targeting several surface molecules on B cells, to reduce the formation of autoantibodies. Such exemplary drugs include rituximab (anti-CD20), ocrelizumab (humanized anti-CD20), belimumab (anti-BAFF/BLyS), atacicept (anti-BLys/APRIL) and epratuzumab (humanized anti-CD22). In addition, other key cell-surface markers have been developed to interfere with costimulatory molecules such as cytotoxic T lymphocyte antigen 4 (abatacept). In addition, Leflunomide (original brand name Arava) is an immunosuppressive pyrimidine synthesis inhibitor that works by inhibiting dihydroorotate dehydrogenase. Leflunomide is an immunomodulatory drug that inhibits the reproduction of rapidly dividing cells, especially lymphocytes. In addition, TNF-α inhibitors, e.g. Etanercept or Infliximab, may be used in some cases.

Exemplary treatment schedules for rheumatoid arthritis include 50 mg/week s.c. Etanercept, 40 mg every other week s.c. Adalimumab, 3 mg/kg-10 mg/kg i.v. for 2-3 hrs. every 4-8 weeks Infliximab, 200 mg-400 mg every 2-4 weeks Certolizumab Pegol, 50 mg/month Golimumab, and 4 mg/kg or 8 mg/kg/month Tocilizumab.

In another embodiment, a method for determining a disease-specific treatment for a subject comprises:

diagnosing the subject as having an autoimmune disease selected from the group consisting of SLE, RA, SSc, SS, and APS, by a method as disclosed herein, and determining that said subject is amenable for receiving a treatment specific to said autoimmune disease. In various embodiments, said treatment is selected from the SLE-specific, RA-specific, SSc-specific, SS-specific, and APS-specific treatments as disclosed herein.

Data Analysis

Advantageously, the methods of the invention can employ the use of learning and pattern recognition analyzers, clustering algorithms and the like, in order to discriminate between reactivity patterns of healthy subjects and patients having different autoimmune diseases including ARDs. For example, the methods can comprise determining the reactivity of antibodies in a test sample to a plurality of antigens, and comparing the resulting pattern to the reactivity patterns of negative and positive control samples using such algorithms and/or analyzers.

In certain embodiments, one or more algorithms or computer programs may be used for comparing the amount of each antibody quantified in the test sample against a predetermined cutoff (or against a number of predetermined cutoffs). Alternatively, one or more instructions for manually performing the necessary steps by a human can be provided.

Algorithms for determining and comparing pattern analysis include, but are not limited to, Support Vector Machine (SVM), Quadratic Discriminant Analysis (QDA), Naïve Bayesian Classifier (NBC), principal component analysis, Fischer linear analysis, neural network algorithms, genetic algorithms, fuzzy logic pattern recognition, and the like. After analysis is completed, the resulting information can, for example, be displayed on a display, transmitted to a host computer, or stored on a storage device for subsequent retrieval.

Many of the algorithms are neural network based algorithms. A neural network has an input layer, processing layers and an output layer. The information in a neural network is distributed throughout the processing layers. The processing layers are made up of nodes that simulate the neurons by the interconnection to their nodes. Similar to statistical analysis revealing underlying patterns in a collection of data, neural networks locate consistent patterns in a collection of data, based on predetermined criteria.

Suitable pattern recognition algorithms include, but are not limited to, principal component analysis (PCA), Fisher linear discriminant analysis (FLDA), soft independent modeling of class analogy (SIMCA), K-nearest neighbors (KNN), neural networks, genetic algorithms, fuzzy logic, and other pattern recognition algorithms. In some embodiments, the Fisher linear discriminant analysis (FLDA) and canonical discriminant analysis (CDA) as well as combinations thereof are used to compare the output signature and the available data from the database.

In other embodiments, principal component analysis is used. Principal component analysis (PCA) involves a mathematical technique that transforms a number of correlated variables into a smaller number of uncorrelated variables. The smaller number of uncorrelated variables is known as principal components. The first principal component or eigenvector accounts for as much of the variability in the data as possible, and each succeeding component accounts for as much of the remaining variability as possible. The main objective of PCA is to reduce the dimensionality of the data set and to identify new underlying variables.

Principal component analysis compares the structure of two or more covariance matrices in a hierarchical fashion. For instance, one matrix might be identical to another except that each element of the matrix is multiplied by a single constant. The matrices are thus proportional to one another. More particularly, the matrices share identical eigenvectors (or principal components), but their eigenvalues differ by a constant. Another relationship between matrices is that they share principal components in common, but their eigenvalues differ. The mathematical technique used in principal component analysis is called eigenanalysis. The eigenvector associated with the largest eigenvalue has the same direction as the first principal component. The eigenvector associated with the second largest eigenvalue determines the direction of the second principal component. The sum of the eigenvalues equals the trace of the square matrix and the maximum number of eigenvectors equals the number of rows of this matrix.

In another embodiment, the algorithm is a classifier. One type of classifier is created by "training" the algorithm with data from the training set and whose performance is evaluated with the test set data. Examples of classifiers used in conjunction with the invention are discriminant analysis, decision tree analysis, receiver operator curves or split and score analysis.

The term "decision tree" refers to a classifier with a flow-chart-like tree structure employed for classification. Decision trees consist of repeated splits of a data set into subsets. Each split consists of a simple rule applied to one variable, e.g., "if value of "variable 1" larger than "threshold 1"; then go left, else go right". Accordingly, the given feature space is partitioned into a set of rectangles with each rectangle assigned to one class.

The terms "test set" or "unknown" or "validation set" refer to a subset of the entire available data set consisting of those entries not included in the training set. Test data is applied to evaluate classifier performance.

The terms "training set" or "known set" or "reference set" refer to a subset of the respective entire available data set. This subset is typically randomly selected, and is solely used for the purpose of classifier construction.

Advantageously, the discrimination between patients having a disease (e.g. SS) and control individuals (e.g. individuals afflicted with SLE) is performed in multi-dimensional space. Conveniently, such analysis is performed by dividing the space into a region characteristic of patients and one for control individuals.

The following examples are presented in order to more fully illustrate some embodiments of the invention. They should, in no way be construed, however, as limiting the broad scope of the invention.

Example 1

Methods:
Patient Samples:

Disease serum samples and clinical information were obtained from the repositories of three independent medical centers and were approved by each respective IRB. SLE (N=30); SS (N=20); RA (N=30); SSc (N=40); and APS (N=16) control patients. The samples were collected from both males and females, females not known to be pregnant, between 18-81 years of age at the time of sample collection.

Self-declared healthy control (N=136) samples were collected in a manner compliant with the HIPPA and with appropriate informed consent. Healthy samples were collected from subjects who had no record of immunologically active disease or steroid use within three months of sample collection, and no first-degree relatives with autoimmune disease.

Study Design:

Testing was performed on 5 manufactured microarray print lots and 6 test sessions. To eliminate biases, samples were assigned to each test session based upon disease class, subject demographics and sample source. Samples were then randomized across microarray print lots, test days and operators Microarray Preparation:

Glass slides were coated with an epoxy silane organic layer, using a YES1224p oven (Yield Engineering Systems, CA, USA). After coating, the slides were packed into slide boxes and vacuum-sealed until printing. Antigens were printed on the coated slides using a Scienion S11 non-contact arrayer (Scienion AG, Germany). The 8 frames slides were blocked with 250 uL of 1% casein (Sigma) and incubated on a rocker (1 h, room temperature, 17 rpm), blocking solution was removed and the diluted serum was added as described below.

Antigen Array:

The microarray was used to display 519 protein and oligonucleotide antigens. Each slide includes 8 identical wells. Testing was performed using 8 well-frame.

Serum Testing:

The slides were allowed to reach room temperature and serum specimens were fully thawed before testing. Serum samples were diluted 1:75 in freshly filtered 1% casein. Diluted serum (150 μl) was dispensed in each well and then incubated (1 h, 37° C.). Each well was then washed with 250 uL PBS, PBS-T, and PBS (5 minutes, room temperature, 17 rpm).

Secondary Antibody Application:

Slides were incubated with goat anti-human IgG-Cy3 (Jackson ImmunoResearch Laboratory) and goat anti-human IgM-Dy5 (Jackson ImmunoResearch Laboratory) diluted 1:2300 in 1% casein in PBS. 150 μl of mixed secondary antibody was dispensed in each well and then incubated (1 hour, 37° C., 8 rpm). Each well was then washed with 250 uL PBS, PBS-T, PBS (5 minutes, room temperature, 17 rpm) and ROW (1 minute, room temperature, 17 rpm). Slides are then centrifuged for 10 min at 2500 rpm at room temperature (23° C.).

Slide Scanning and Data Processing:

The slides were scanned at two wavelengths (532 nm and 633 nm) using an Agilent scanner (Agilent Technologies, Santa Clara, Calif.) and images were extracted using the GenePix 7.0 feature extraction (FE) software (Molecular Devices, Sunnyvale, Calif.), using default settings. All scanned images were preprocessed.

Data preprocessing involved these major steps: subtraction of background, data transformation, removal of outliers, combination of replicates, adjustment of overall intensity per slide and correction of print lot effect. Specifically, the pre-processing procedure included the following steps:

Determining representation of each spot through subtraction of background intensity from the foreground intensity; imputing negative values with low intensity spots, as negative spots have no meaning in the context of the platform; performing log transformation on each spot and combining spot replicates per array, wherein outliers spots were removed based on Grubb's test; adjusting the mean per array per channel, wherein the mean per array was calculated based on a set of antigens per channel, and the mean may then be adjusted against a constant value and the correction was applied to all antigens; and correcting for print lot and test session effect using reference sera, wherein the correction was performed per test session per print lot, by subtraction of reference serum intensities from corresponding antigens in order to express all intensities as relative to the reference serum.

Results:

The samples were tested for their intensity of binding to the arrayed antigens as described herein above and univariate analysis (FDR adjusted p-values) was used to determine the ability of each antigen to separate between healthy controls (HC) and autoimmune diseased patients or between specific autoimmune rheumatic diseased patients, for example, SLE and RA, SLE and SSC, SLE and APS, SLE and SS, SS and SSc, SS and RA.

Table 13 summarized the univariate FDR adjusted p-values between healthy subjects and individuals having an autoimmune disease.

TABLE 13

Examples of univariate separation between healthy subjects and individuals having an autoimmune disease.

| Antigen | Isotype | HC vs SSC, APS, SS, RA and SLE patients (FDR-adjusted p-values) |
|---|---|---|
| LAIR-1 | IgG | 2.78E−63 |
| Collagen II | IgG | 5.02E−22 |
| CD62P | IgG | 4.37E−17 |
| TGM2 | IgG | 2.41E−15 |
| Chromatin | IgG | 6.63E−15 |

Next, the multivariate comparisons as follows were addressed:

Healthy controls (HCs) vs all autoimmune rheumatic diseases patients, including SSc, APS, SS, RA, and SLE; HCs vs SLE; HCs vs SSC; HCs vs APS; HCs vs SS; HCs vs RA; SLE vs SSc; SLE vs APS; SLE vs SS; SLE vs RA; SSC vs APS; SSc vs. SS; SSC vs RA; APS vs SS; APS vs RA; and SS vs RA.

Multivariate analysis procedure used three models: SVM, QDA and Naïve Bayes classifier. Classifier training and testing were performed based on 10-fold cross validation on all samples, and the performance of each classifier was determined. The classifiers typically included up to 20 antigens on average.

Tables 1-12, presented at Example 2 below, list exemplary antigens against which the antibody reactivity between the indicated groups was found to be significantly different. The results of some of the comparisons obtained mean accuracy, mean sensitivity and mean specificity as listed in Table 14. Table 15 lists the antibody reactivities (IgG or IgM) significance (FDR adjusted p-values) of some of the comparisons listed above. Tables 16-28, presented at Example 2 below, list additional exemplary antigens against which the antibody reactivity between the indicated groups was found to be significantly different.

TABLE 14

Mean accuracy per specific comparisons.

| Question | Mean accuracy | Mean Sensitivity | Mean Specificity |
|---|---|---|---|
| HCs vs RA | 0.98 | 0.97 | 0.99 |
| HCs vs APS | 0.97 | 0.85 | 0.91 |
| HCs vs SLE | 0.96 | 0.89 | 0.98 |
| HCs vs SS | 0.96 | 0.90 | 0.97 |
| SLE vs RA | 0.95 | 0.92 | 0.98 |
| HCs vs SSc, APS, SS, RA, and SLE | 0.95 | 0.93 | 0.96 |
| APS vs SS | 0.94 | 0.90 | 0.98 |
| HCs vs SSC | 0.93 | 0.86 | 0.95 |
| SLE vs SSC | 0.92 | 0.92 | 0.93 |

Example 2

Tables 1-12 and 16-28, summarizing the antigens identified in the experiments described in Example 1, are presented below.

TABLE 1

Exemplary antigens against which antibody reactivity was found to be significantly different between autoimmune rheumatic diseased patients (SLE, SSc, APS, SS, and RA) and healthy control subjects.

| Antigen | Antibody | Antigen details |
|---|---|---|
| BPI | IgG | Bactericidal permeability-increasing protein |
| C1s | IgG | Complement component C1s |
| C4 | IgM | Complement component C4 |
| C4c | IgM | Complement Component C4c |
| CA125 | IgG | Cancer Antigen 125 |
| CD137 | IgM | TNF receptor superfamily member 9 |
| CD62P | IgG, IgM | P-Selectin/CD62P |
| CENPB | IgG | Centromere Protein-B, rh |
| CHD4 | IgM | Chromodomain helicase DNA binding protein 4 |
| Chromatin | IgG | chromatin |
| collagenII | IgG | Collagen II |
| CTLA4 | IgM | Cytotoxic T-Lymphocyte Associated Antigen-4/Fc Chimera |
| DT | IgG | Diphtheria Toxin from *Corynebacterium diphtheriae* |
| EPO | IgM | Erythropoietin |
| ESD | IgG | Esterase-D |
| EXOSC10 | IgM | Exosome component 10 |
| Ferritin | IgG | Ferritin |
| FPR1 | IgG | formyl peptide receptor 1 |
| FSCN1 | IgM | fascin homolog 1, actin-bundling protein |
| H1 | IgM | Histone H1 |
| H3 | IgG | Histone-H3 |
| HLAB | IgG | *Homo sapiens* major histocompatibility complex, class I, B |
| HLAC | IgG | Major Histocompatibility Complex Class I-C |
| IL35 | IgM | Interleukin 35 |
| LAIR1 | IgG | Leukocyte-associated immunoglobulin-like receptor 1 |

TABLE 1-continued

Exemplary antigens against which antibody reactivity was found to be significantly different between autoimmune rheumatic diseased patients (SLE, SSc, APS, SS, and RA) and healthy control subjects.

| Antigen | Antibody | Antigen details |
| --- | --- | --- |
| LeptintA | IgG | Leptin Antagonist Triple |
| MICA | IgM | MHC class I polypeptide-related sequence A |
| MX1 | IgG | myxovirus (influenza virus) resistance 1, p78 interferon-inducible protein |
| MYH1 | IgG | Myosin heavy chain 1 |
| NAP1L1 | IgM | Nucleosome Assembly Protein 1-Like 1 |
| RO60 | IgG | TROVE Domain Family Member 2 |
| TGM2 | IgG | Tissue Transglutaminase |
| TgondiiP24 | IgM | Toxoplasma Gondii p24 (GRA1) |
| THBS1 | IgG | thrombospondin 1 |
| Tyk2 | IgG | tyrosine kinase 2 |
| YLK40 | IgM | Chitinase-3-like protein 1 |

TABLE 2

Exemplary antigens against which antibody reactivity was found to be significantly different between SLE patients and RA patients.

| Antigen | Reactivity | Antigen details |
| --- | --- | --- |
| APEX1 | IgG | APEX Nuclease-1 |
| ATF2 | IgG | Activating Transcription Factor 2 |
| B7H4 | IgG | V-Set Domain Containing T Cell Activation Inhibitor 1 |
| BCOADC-E2 | IgG | 2-Oxo-Acid Dehydrogenase Complex E2 Human |
| BDNF | IgG | Brain-Derived Neurotrophic Factor rec hu |
| BPI | IgM | Bactericidal permeability-increasing protein |
| BST2 | IgG | bone marrow stromal antigen 2 |
| C2 | IgG | Complement component C2 |
| C3b | IgG | Complement C3b protein |
| CD29 | IgG | Integrin subunit beta 1 |
| CD3E | IgG | CD3 ε,CD3e molecule, epsilon (CD3-TCR complex) Protein |
| CD62P | IgG | P-Selectin/CD62P |
| CRYAB | IgG | Alpha-crystallin B chain |
| CX3CL1 | IgG | Fractalkine/CX3CL1 |
| chromatin | IgG | Chromatin |
| DLST | IgG | 2-oxoglutarate dehydrogenase complex component E2 |
| FABP1 | IgG | fatty acid binding protein 1, liver |
| FASLG | IgG | Recombinant Human FAS Ligand |
| FRP1 | IgG | formyl peptide receptor 1 |
| Factor II | IgG | Clotting Factor II, hum prothrombin |
| Factor P | IgG | Complement Factor P (Properdin) |
| Ferritin | IgG | Ferritin |
| GBE1 | IgG | Alpha-1,4-glucan branching enzyme 1 |
| H1 | IgG | Histone H1 |
| H2BQ | IgG | Human Histone cluster 2 H2BE |
| H2B | IgG | Histone H2B, |
| H4 | IgG | Histone H4 |
| HNRNPA1 | IgG | Heterogeneous nuclear ribonucleoprotein A1 |
| IL35 | IgG | Interleukin 35 |
| JO-1 | IgG | Histidyl tRNA Synthetase |
| LIGHT | IgG | Tumor Necrosis Factor (Ligand) Superfamily Member 14 |
| NOR90 | IgG | Nucleolar transcription factor 1 |
| OX40 | IgG | Tumor necrosis factor receptor superfamily member 4 |
| PL-12 | IgG | Alanyl t-RNA Synthetase, rh |
| RANTES | IgM | RANTES (CCL5), rh |
| RNPsm | IgM, IgG | RNP-Sm complex |
| RO60 | IgG | TROVE Domain Family Member 2 |
| RPLP1 | IgG | 60S acidic ribosomal protein P1 |
| RLP2 | IgG | Receptor-like protein 2 |
| RPPO | IgG | Ribosomal Phosphoprotein P0 rh |
| RibosomalP | IgG | Ribosomal P Antigen |
| SAP | IgG | Serum Amyloid P |
| SDF1a | IgG | Stromal Cell-Derived Factor-1 alpha (CXCL12) |
| SNRPA | IgG | U1 small nuclear ribonucleoprotein A |
| SNRPB | IgG, IgM | small nuclear ribonucleoprotein polypeptides B and B1 |

TABLE 2-continued

Exemplary antigens against which antibody reactivity was found to be significantly different between SLE patients and RA patients.

| Antigen | Reactivity | Antigen details |
| --- | --- | --- |
| SNRPC | IgM, IgG | U1 small nuclear ribonucleoprotein C |
| SP100 | IgG | Nuclear autoantigen Sp-100 |
| SPTAN1 | IgG | Alpha II-spectrin |
| STAT1 | IgG | STAT1 rh |
| STAT4 | IgG | signal transducer and activator of transcription 4 |
| STAT5a | IgG | Signal transducer and activator of transcription 5A |
| Sm-D1 | IgG | Small nuclear ribonucleoprotein D1 |
| SmD | IgG | Small nuclear ribonucleoprotein (D1, D2 and D3) |
| THBS1 | IgG | thrombospondin 1 |
| WNV | IgM | West Nile Virus |
| Zyxin | IgG | Zyxin |

TABLE 3

Exemplary antigens against which antibody reactivity was found to be significantly different between SLE patients and SSc patients.

| Antigen | Reactivity | Antigen details |
| --- | --- | --- |
| B7H4 | IgG | V-Set Domain Containing T Cell Activation Inhibitor 1 |
| BDNF | IgG | Brain-Derived Neurotrophic Factor rec hu |
| C2 | IgG | Complement component C2 |
| C3b | IgG | Complement C3b protein |
| CD62P | IgG | P-Selectin/CD62P |
| chromatin | IgG, IgM | chromatin |
| DLST | IgG | 2-oxoglutarate dehydrogenase complex component E2 |
| FABP1 | IgG | fatty acid binding protein 1, liver |
| FASLG | IgG | Recombinant Human FAS Ligand |
| Factor II | IgG | Clotting Factor II, hum prothrombin |
| Factor P | IgG | Complement Factor P (Properdin) |
| GBE1 | IgG | Alpha-1,4-glucan branching enzyme 1 |
| H1 | IgG | Histone H1 |
| H2B | IgG | Histone H2B |
| H4 | IgG | Histone H4 |
| HNRNPA1 | IgG | Heterogeneous nuclear ribonucleoprotein A1 |
| IL35 | IgG | Interleukin 35 |
| LIGHT | IgG | Tumor Necrosis Factor (Ligand) Superfamily Member 14 |
| LMNB1 | IgG | Lamin B1 |
| RNPsm | IgM, IgG | RNP-Sm complex |
| RO60 | IgG | TROVE Domain Family Member 2 |
| RLPLP1 | IgG | Receptor-like protein 1 |
| RPLP2 | IgG | 60S acidic ribosomal protein P2 |
| RPPO | IgG | Ribosomal Phosphoprotein P0 rh |
| RibosomalP | IgG | Ribosomal P Antigen |
| SAP | IgG | Serum Amyloid P |
| SDF1a | IgG | Stromal Cell-Derived Factor-1 alpha (CXCL12) |
| SM-D3 | IgG | Small nuclear ribonucleoprotein D3 polypeptide |
| SNRPA | IgG | U1 small nuclear ribonucleoprotein A |
| SNRPB | IgM | small nuclear ribonucleoprotein polypeptides B and B1 |
| SNRPC | IgM, IgG | U1 small nuclear ribonucleoprotein C |
| SPTAN1 | IgG | Alpha II-spectrin |
| STAT5a | IgG | Signal transducer and activator of transcription 5A |
| Sm-Dl | IgG | Small nuclear ribonucleoprotein D1 |
| SmD | IgG | Small nuclear ribonucleoprotein (D1, D2 and D3) |

TABLE 4

Exemplary antigens against which antibody reactivity was found to be significantly different between SLE patients and APS patients.

| Antigen | Reactivity | Antigen details |
|---|---|---|
| OX40 | IgG | Tumor necrosis factor receptor superfamily member 4 |
| SNRPA | IgG | U1 small nuclear ribonucleoprotein A |
| SNRPB | IgG | small nuclear ribonucleoprotein polypeptides B and B1 |
| STAT5a | IgG | Signal transducer and activator of transcription 5A |

TABLE 5

Exemplary antigens against which antibody reactivity was found to be significantly different between SS patients and SSc patients.

| Antigen | Reactivity | Antigen details |
|---|---|---|
| AITRL | IgG | Tumor necrosis factor ligand superfamily member 18 |
| C2 | IgG | Complement component C2 |
| CRYAB | IgG | Alpha-crystallin B chain |
| CXCL2 | IgG | C-X-C motif chemokine ligand 2 |
| Endostatin P1 | IgG, IgM | Collagen XVIII (1154-1335) |
| FASLG | IgG | Recombinant Human FAS Ligand |
| FGFb | IgG | Fibroblast Growth Factor-basic rh |
| Factor II | IgG | Clotting Factor II, hum prothrombin |
| GCSF | IgG | Granulocyte-Colony Stimulating Factor |
| H1 | IgG | Histone H1 |
| H2B | IgG | Histone H2B |
| H4 | IgG | Histone H4 |
| IL3 | IgG | Interleukin-3 rh |
| LFA1 | IgG | Lymphocyte function-associated antigen 1 |
| MIP1b | IgG | Macrophage Inflammatory Protein-1 beta |
| OX40L | IgG | Tumor necrosis factor ligand superfamily member 4 |
| RO60 | IgG, IgM | TROVE Domain Family Member 2 |
| SDF1a | IgG | Stromal Cell-Derived Factor-1 alpha (CXCL12) |
| STAT5a | IgG | Signal transducer and activator of transcription 5A |
| Sm-D1 | IgG | Small nuclear ribonucleoprotein D1 |
| SmD | IgG | Small nuclear ribonucleoprotein (D1, D2 and D3) |

TABLE 6

Exemplary antigens against which antibody reactivity was found to be significantly different between SS patients and RA patients.

| Antigen | Reactivity | Antigen details |
|---|---|---|
| BDNF | IgG | Brain-Derived Neurotrophic Factor rec hu |
| C2 | IgG | Complement component C2 |
| CRYAB | IgG | Alpha-crystallin B chain |
| CX3CL1 | IgG | Fractalkine/CX3CL1 |
| CXCL2 | IgG | C-X-C motif chemokine ligand 2 |
| Endostatin P1 | IgG, IgM | Collagen XVIII (1154-1335) |
| FASLG | IgG | Recombinant Human FAS Ligand |
| FGFb | IgG | Fibroblast Growth Factor-basic rh |
| Factor II | IgG | Clotting Factor II, hum prothrombin |
| GCSF | IgG | Granulocyte-Colony Stimulating Factor |
| Glypican6 | IgG | Glypican6 |
| H1 | IgG | Histone H1 |
| H2B | IgG | Histone H2B |
| H4 | IgG | Histone H4 |
| HNRNPA1 | IgG | Heterogeneous nuclear ribonucleoprotein A1 |
| IL3 | IgG | Interleukin-3 rh |
| LFA1 | IgG | Lymphocyte function-associated antigen 1 |
| MIP1b | IgG | Macrophage Inflammatory Protein-1 beta |
| OX40L | IgG | Tumor necrosis factor ligand superfamily member 4 |
| RO60 | IgG, IgM | TROVE Domain Family Member 2 |
| RPLP1 | IgG | 60S acidic ribosomal protein P1 |
| RibosomalP | IgG | Ribosomal P Antigen |
| SDF1a | IgG | Stromal Cell-Derived Factor-1 alpha (CXCL12) |
| SNRPB | IgG | small nuclear ribonucleoprotein polypeptides B and B1 |
| STAT1 | IgG | STAT1 rh |
| STAT5a | IgG | Signal transducer and activator of transcription 5A |
| SmD | IgG | Small nuclear ribonucleoprotein (D1, D2 and D3) |

TABLE 7

Exemplary antigen against which antibody reactivity was found to be significantly different between SLE patients and SS patients.

| Antigen | Reactivity | Antigen details |
|---|---|---|
| RNPsm | IgG | RNP-Sm complex |

TABLE 8

Exemplary antigens against which antibody reactivity was found to be significantly different between SLE patients and healthy control subjects.

| Antigen | Reactivity | Antigen details |
|---|---|---|
| APEX | IgG | APEX Nuclease-1 |
| B7-2 | IgM | B-lymphocyte antigen B7-2 |
| B7H4 | IgG | V-Set Domain Containing T Cell Activation Inhibitor 1 |
| BCOADC-E2 | IgG | 2-Oxo-Acid Dehydrogenase Complex E2 Human |
| BDNF | IgG, IgM | Brain-Derived Neurotrophic Factor rec hu |
| BMP7 | IgM | Bone Morphogenetic protein-7 |
| BST2 | IgG | bone marrow stromal antigen 2 |
| C1s | IgG | Complement component C1s |
| C2 | IgG | Complement component C2 |
| C3b | IgG | Complement C3b protein |
| C3c | IgG | Complement Component C3c |
| CD3e | IgG | CD3 ε,CD3e molecule, epsilon (CD3-TCR complex) Protein, |
| CD46 | IgG | Membrane cofactor protein |
| CD62P | IgG | P-Selectin/CD62P |
| CD80 | IgM | B-lymphocyte Activation Antigen B7-1 (CD80/B7-1) Protein |
| CTLA4 | IgM | Cytotoxic T-Lymphocyte Associated Antigen-4/Fc Chimera |
| chromatin | IgG, IgM | chromatin |
| collagen II | IgG | collagen II |
| DLST | IgG | 2-oxoglutarate dehydrogenase complex component E2 |
| Factor P | IgG | Complement Factor P (Properdin) |
| H1 | IgG, IgM | Histone H1 |

TABLE 8-continued

Exemplary antigens against which antibody reactivity was found to be significantly different between SLE patients and healthy control subjects.

| Antigen | Reactivity | Antigen details |
|---|---|---|
| H2BQ | IgG, IgM | Human Histone cluster 2 H2BE |
| H2B | IgG, IgM | Histone H2B, |
| H4 | IgG, IgM | Histone H4 |
| IFNa2 | IgG | Interferon-alpha 2 rhu |
| IL4 | IgG, IgM | Interleukin-4 rh |
| LAIR1 | IgG | Leukocyte-associated immunoglobulin-like receptor 1 |
| LIGHT | IgG | Tumor Necrosis Factor (Ligand) Superfamily Member 14 |
| MICA | IgM | MHC class I polypeptide-related sequence A |
| MitoAg | IgG | Mitochondrial Antigen-Pyruvate dehydrogenase complex |
| NFkB | IgG | Transcription Regulator NFkB, NF kappa B rh, |
| OX40 | IgG | Tumor necrosis factor receptor superfamily member 4 |
| RANTES | IgM | RANTES (CCL5), rh |
| RNPsm | IgM, IgG | RNP-Sm complex |
| RO60 | IgG | TROVE Domain Family Member 2 |
| RPLP1 | IgG | 60S acidic ribosomal protein P1 |
| RPLP2 | IgG | 60S acidic ribosomal protein P2 |
| RPPO | IgG | Ribosomal Phosphoprotein P0 rh |
| RibosomalP | IgG, IgM | Ribosomal P Antigen |
| CENPB | IgG | Centromere Protein-B, rh |
| HSV2 | IgM | Herpes Simplex Virus-2 gD |
| Tgondii24 | IgM | Toxoplasma Gondii p24 (GRA1) |
| YLK | IgM | Chitinase-3-like protein 1 |
| SAP | IgM | Serum Amyloid P |
| SDF1a | IgG | Stromal Cell-Derived Factor-1 alpha (CXCL12) |
| SNRPA | IgG, IgM | U1 small nuclear ribonucleoprotein A |
| SNRPB | IgG, IgM | small nuclear ribonucleoprotein polypeptides B and B1 |
| SNRPC | IgM, IgG | U1 small nuclear ribonucleoprotein C |
| SP100 | IgG | Nuclear autoantigen Sp-100 |
| SPTAN1 | IgM, IgG | Alpha II-spectrin |
| SYND1 | IgM | syndecan 1 |
| Sm-D1 | IgG, IgM | Small nuclear ribonucleoprotein D1 |
| SmD | IgG, IgM | Small nuclear ribonucleoprotein (D1, D2 and D3) |
| TGM2 | IgG | Tissue Transglutaminase |
| TNFb | IgG | Tumor Necrosis Factor-beta (TNF-b), rh |
| TRAIL | IgG | TNF-Related Apoptosis Inducing Ligand/Apo2L rh |
| XRcc5 | IgG | X-ray repair complementing defective repair in Chinese hamster cells 5 |
| oxLDL | IgG | Oxidized low-density lipoprotein |
| pADPr | IgG | Poly (ADP) Ribose Polymer-PAR |

TABLE 9

Exemplary antigens against which antibody reactivity was found to be significantly different between SSc patients and healthy control subjects.

| Antigen | Reactivity | Antigen details |
|---|---|---|
| ATF2 | IgG | Activating Transcription Factor 2 |
| BPI | IgG | Bactericidal permeability-increasing protein |
| CA125 | IgG | Cancer Antigen 125 |
| CD29 | IgG | Integrin subunit beta 1 |
| CD31 | IgG | PECAM1: platelet/endothelial cell adhesion molecule (CD31 antigen) |
| CD8A | IgG | T-cell surface glycoprotein CD8 alpha chain |
| CRYAB | IgG | Alpha-crystallin B chain |
| Catalase | IgG | Catalase (bovine) |
| collagen II | IgG | collagen II |
| DT | IgG | Diphtheria Toxin from Corynebacterium diphtheriae |
| ESD | IgG | Esterase-D |
| FPR1 | IgG | formyl peptide receptor 1 |
| Ferritin | IgG | Ferritin |
| H2BQ | IgG | Human Histone cluster 2 H2BE |
| H3 | IgG | Histone-H3 |
| HLAB | IgG | *Homo sapiens* major histocompatibility complex, class I, B |
| HLAC | IgG | Major Histocompatibility Complex Class I-C |
| Haptoglobin 2-2 | IgG | Haptoglobin 2-2 |
| IL4 | IgG | Interleukin-4 rh |
| Ki67 | IgG | Ki67 |
| LAIR1 | IgG | Leukocyte-associated immunoglobulin-like receptor 1 |
| LeptinA | IgG | Leptin Antagonist Triple |

TABLE 9-continued

Exemplary antigens against which antibody reactivity was found to be significantly different between SSc patients and healthy control subjects.

| Antigen | Reactivity | Antigen details |
|---|---|---|
| MASP2 | IgG | Mannan-binding lectin serine protease 2 |
| MX1 | IgG | myxovirus (influenza virus) resistance 1, interferon-inducible protein p78 |
| MYH1 | IgG | Myosin heavy chain 1 |
| Neurofilament 68 | IgG | Neurofilament 68 from ARP American Research Products, Inc. |
| RibosomalP | IgG | Ribosomal P Antigen |
| CENPB | IgG | Centromere Protein-B, rh |
| EXOSC10 | IgM | Exosome component 10 |
| Tgondii24 | IgM | Toxoplasma Gondii p24 (GRA1) |
| YLK40 | IgM | Chitinase-3-like protein 1 |
| SerpinG1 | IgG | C1 esterase inhibitor |
| TGM2 | IgG | Tissue Transglutaminase |
| THBS1 | IgG | hrombospondin 1 |
| Tyk2 | IgG | tyrosine kinase 2 |
| oxLDL | IgG | Oxidized low-density lipoprotein |

TABLE 10

Exemplary antigens against which antibody reactivity was found to be significantly different between APS patients and healthy control subjects.

| Antigen | Reactivity | Antigen details |
|---|---|---|
| BCM01$^{p6-206}$ | IgG | beta-carotene oxygenase 1 |
| BPI | IgG | Bactericidal permeability-increasing protein |
| Chromatin | IgM | chromatin |
| Ferritin | IgG | Ferritin |
| H1 | IgM | Histone H1 |
| HLAC | IgG | Major Histocompatibility Complex Class I-C |
| LAIR1 | IgG | Leukocyte-associated immunoglobulin-like receptor 1 |
| MYH1 | IgG | Myosin heavy chain 1 |
| Sm-D1 | IgM | Small nuclear ribonucleoprotein D1 |
| SmD | IgM | Small nuclear ribonucleoprotein (D1, D2 and D3) |
| TGM2 | IgG | Tissue Transglutaminase |
| Tyk2 | IgG | tyrosine kinase 2 |

TABLE 11

Exemplary antigens against which antibody reactivity was found to be significantly different between SS patients and healthy control subjects.

| Antigen | Reactivity | Antigen details |
|---|---|---|
| APEX | IgG | APEX Nuclease-1 |
| C2 | IgG | Complement component C2 |
| CD137L | IgG | Tumor Necrosis Factor (ligand) Superfamily Member 9 |
| CRYAB | IgG | Alpha-crystallin B chain |
| CXCL2 | IgG | C-X-C motif chemokine ligand 2 |
| Chromatin | IgG | chromatin |
| Endostatin | IgG, IgM | Collagen XVIII (1154-1335) |
| P1 | | |
| H1 | IgG | Histone H1 |
| H2B | IgG | Histone H2B |
| H4 | IgG | Histone H4 |
| IL3 | IgG | Interleukin-3 rh |
| LAIR1 | IgG | Leukocyte-associated immunoglobulin-like receptor 1 |
| La | IgG | la-like antigen, LA/SS-B, rh, |
| MIP1b | IgG | Macrophage Inflammatory Protein-1 beta |
| OX40L | IgG, IgM | Tumor necrosis factor ligand superfamily member 4 |
| RO60 | IgG, IgM | TROVE Domain Family Member 2 |
| C4c | IgM | Complement Component C4c |
| EXOSC10 | IgM | Exosome component 10 |
| EXOSC9 | IgM | Exosome component 9 |
| Tgondii24 | IgM | Toxoplasma Gondii p24 (GRA1) |
| SDF1a | IgG | Stromal Cell-Derived Factor-1 alpha (CXCL12) |
| SNRPB | IgG | small nuclear ribonucleoprotein polypeptides B and B1 |
| Sm-D1 | IgG | Small nuclear ribonucleoprotein D1 |
| SmD | IgG, IgM | Small nuclear ribonucleoprotein (D1, D2 and D3) |

TABLE 12

Exemplary antigens against which antibody reactivity was found to be significantly different between RA patients and healthy control subjects.

| Antigen | Reactivity | Antigen details |
|---|---|---|
| ATF2 | IgG | Activating Transcription Factor 2 |
| BPI | IgG | Bactericidal permeability-increasing protein |
| C4c | IgM | Complement Component C4c |
| CA125 | IgG | Cancer Antigen 125 |
| CD137 | IgM | TNF receptor superfamily member 9 |
| CD29 | IgG | Integrin subunit beta 1 |
| collagen II | IgG | collagen II |
| CRYAB | IgG | Alpha-crystallin B chain |
| DT | IgG | Diphtheria Toxin from Corynebacterium diphtheriae |
| Entactin | IgG | Entactin/Nidogen |
| EPO | IgM | Erythropoietin |
| ESD | IgG | Esterase-D |

TABLE 12-continued

Exemplary antigens against which antibody reactivity was found to be significantly different between RA patients and healthy control subjects.

| Antigen | Reactivity | Antigen details |
| --- | --- | --- |
| EXOSC10 | IgM | Exosome component 10 |
| Ferritin | IgG | Ferritin |
| FPR1 | IgG | formyl peptide receptor 1 |
| GSTP1 | IgG | glutathione S-transferase pi 1 |
| H2BQ | IgG | Human Histone cluster 2 H2BE |
| H3 | IgG | Histone-H3 |
| HLAB | IgG | *Homo sapiens* major histocompatibility complex, class I, B |
| HLAC | IgG | Major Histocompatibility Complex Class I-C |
| LAG3 | IgG | Lymphocyte activation gene 3 protein |
| LAIR1 | IgG | Leukocyte-associated immunoglobulin-like receptor 1 |
| Leptin A | IgG | Leptin Antagonist Triple |
| LIGHT | IgG | Tumor Necrosis Factor (Ligand) Superfamily Member 14 |
| MASP2 | IgG | Mannan-binding lectin serine protease 2 |
| Mi-2 | IgG | Chromodomain-helicase-DNA-binding protein Mi-2 homolog |
| MX1 | IgG | myxovirus (influenza virus) resistance 1, interferon-inducible protein p78 |
| MYH1 | IgG | Myosin heavy chain 1 |
| NAP1L1 | IgG, IgM | Nucleosome Assembly Protein 1-Like 1 |
| Neurofilament[68] | IgG | Neurofilament 68 from ARP American Research Products, Inc. |
| NGAL | IgM | Neutrophil Gelatinase Associated rh |
| NRBF2 | IgG | Nuclear receptor-binding factor 2 |
| RibosomalP | IgG | Ribosomal P Antigen |
| STAT1 | IgG | STAT1 rh |
| STAT4 | IgG | signal transducer and activator of transcription 4 |
| STAT6 | IgG | STAT6 |
| THBS 1 | IgG | thrombospondin 1 |
| Tyk2 | IgG | tyrosine kinase 2 |
| YLK40 | IgM | Chitinase-3-like protein 1 |

TABLE 16

Additional exemplary antigens against which antibody reactivity was found to be significantly different between autoimmune rheumatic diseased patients (SLE, SSc, APS, SS, and RA) and healthy control subjects.

| Antigen | Reactivity | Antigen details |
| --- | --- | --- |
| C1q | IgG | Complement component C1Q |
| DNAds | IgM, IgG | DNA double strand |
| DNAss | IgM, IgG | DNA single strand |
| H2a | IgM | Histone H2A |
| Histone3S calf | IgG, IGM | Histone from calf thymus Type III-S |
| Oligo 9 | IgG, IGM | GGG GGG GGG GGG GG |
| CHMP2A | IgM | chromatin modifying protein 2A |
| Collagen III | IgM | Collagen III |
| EBV | IgG | Epstein-Barr Virus |
| EXOSC5 | IgM | Exosome component 5 |
| FABP | IgM | Fatty Acid Binding Protein, rh FABP3 |
| HGF | IgM | Hepatocyte Growth Factor |
| INFg | IgM | Interferon gamma |
| LPS | IgG | Lipopolysaccharide |
| Ro52 | IgG, IgM | Tripartite Motif Containing 21 (RO52) |
| TPO | IgM | Thyroid Peroxidase |
| Thyro-globulin | IgM | Thyroglobulin from bovine thyroid |
| VEGF | IgM | Vascular Endothelial Growth Factor, rh, |
| Vimentin | IgM | Vimentin from bovine lens |
| Oligo 21 | IgM | TTA GGG TTA GGG TTA GGG TTA GGG |
| Sm | IgG | smith antigen |
| U1snRNP | IgG | U1 small nuclear ribo-nucleoprotein 70 kDa |
| Oligo 10 | IgG | GGG GGG GGG GGG GGG GG |
| Oligo 11 | IgG | GGG GGG GGG GGG GGG GGG GG |
| Oligo 27 | IgM | GGG GGG GGG GGG GGG GT |
| Oligo 27 | IgG | GGG GGG GGG GGG GGG GT |
| Oligo 28 | IgG, IgM | GGG GGG G |
| Oligo 29 | IgG, IgM | GGG GGG GGG |

TABLE 16-continued

Additional exemplary antigens against which antibody reactivity was found to be significantly different between autoimmune rheumatic diseased patients (SLE, SSc, APS, SS, and RA) and healthy control subjects.

| Antigen | Reactivity | Antigen details |
|---|---|---|
| Oligo 30 | IgM, IgG | TGG GGG GGG GGG GGG GG |
| Oligo 5 | IgG | CGC GCG CGC GCG CGC GCG CG |
| Oligo 7 | IgG | GAG AGA GAG AGA GAG AGA GA |

TABLE 17

Additional exemplary antigens against which antibody reactivity was found to be significantly different between SLE patients and healthy control subjects.

| Antigen | Reactivity | Antigen details |
|---|---|---|
| C1q | IgG | Complement component C1Q |
| DNAds | IgM, IgG | DNA double strand |
| DNAss | IgG | DNA single strand |
| H2a | IgG, IGM | Histone H2A |
| Histone 3S calf | IgG, IgM | Histone from calf thymus Type III-S |
| IL4 | IgG, IGM | Interleukin-4 rh |
| Laminin | IgG | Laminin |
| Oligo 22 | IgG | GTT TTT TTT TTT TTT TTG |
| Oligo 26 | IgG | TTT TTT TTT TTT TTT TGG |
| Oligo 4 | IgG | CCC CCC CCC CCC CCC CCC CC |
| Oligo 8 | IgG | GTG TGT GTG TGT GTG TGT GT |
| Oligo 9 | IgG | GGG GGG GGG GGG GG |
| PARP1 | IgG | Poly (ADP-Ribose) Polymerase 1 Human |
| CENPH | IgM | centromere protein H |
| CHMP2A | IgM | chromatin modifying protein 2A |
| Collagen III | IgM | Collagen III |
| EBV | IgG | Epstein-Barr Virus |
| EXOSC5 | IgM | Exosome component 5 |
| PARP | IgM | Poly (ADP-Ribose) Polymerase 1 Human |
| HGF | IgM | Hepatocyte Growth Factor |
| Ro52 | IgG | Tripartite Motif Containing 21 (RO52) |
| Oligo 21 | IgM, IgG | TTA GGG TTA GGG TTA GGG TTA GGG |
| SM-D3 | IgG, IgM | Small nuclear ribonucleoprotein D3 polypeptide |
| Sm | IgG, IGM | smith antigen |
| U1snRNP | IgG | U1 small nuclear ribonucleoprotein 70 kDa |
| huIgG | IgG | human IgG |
| oligo 10 | IgG | GGG GGG GGG GGG GGG GG |
| oligo 11 | IgG | GGG GGG GGG GGG GGG GGG GG |
| oligo 16 | IgG | CCA TAA TTG CAA ACG TTC TG |
| oligo 17 | IgG | CCA TAA TTG CAA AGC TTC TG |
| oligo 19 | IgG | TTG GGG GGG GGG GGG GGG TT |
| oligo 1 | IgG | AAA AAA AAA AAA AAA AAA AA |
| oligo 20 | IgG | CCA TAA TTC GAA ACG TTC TG |
| oligo 27 | IgM | GGG GGG GGG GGG GGG GT |
| oligo 27 | IgG | GGG GGG GGG GGG GGG GT |
| oligo 28 | IgG | GGG GGG G |
| oligo 28 | IgM | GGG GGG G |
| oligo 29 | IgG, IgM | GGG GGG GGG |
| oligo 30 | IgM, IgG | TGG GGG GGG GGG GGG GG |
| oligo 5 | IgG | CGC GCG CGC GCG CGC GCG CG |
| oligo 7 | IgG | GAG AGA GAG AGA GAG AGA GA |

TABLE 18

Additional exemplary antigens against which antibody reactivity was found to be significantly different between SSc patients and healthy control subjects.

| Antigen | Reactivity | Antigen details |
|---|---|---|
| B2GP 1 | IgG | B2GP1 Human Glycoprotein 1 Beta-2 Human, Glycoprotein 1, β2 |
| C1q | IgG | Complement component C1Q |
| Collagen III | IgM | Collagen III |
| EBV | IgG | Epstein-Barr Virus |
| EXOSC5 | IgM | Exosome component 5 |
| Ro52 | IgG | Tripartite Motif Containing 21 (RO52) |
| VEGF | IgM | Vascular Endothelial Growth Factor, rh, |

TABLE 19

Additional exemplary antigens against which antibody reactivity was found to be significantly different between APS patients and healthy control subjects.

| Antigen | Reactivity | Antigen details |
|---|---|---|
| EXOSC5 | IgM | Exosome component 5 |
| H2a | IgM | Histone H2A |
| Histone 3S calf | IgM | Histone from calf thymus Type III-S |
| Oligo 27 | IgM | GGG GGG GGG GGG GGG GT |
| Oligo 28 | IgM | GGG GGG G |
| SM-D3 | IgG | Small nuclear ribonucleo-protein D3 polypeptide |
| TNFRSF 12A | IgG | human TNF ligand receptor superfamily member12A |

TABLE 20

Additional exemplary antigens against which antibody reactivity was found to be significantly different between SS patients and healthy control subjects.

| Antigen | Reactivity | Antigen details |
|---|---|---|
| Collagen III | IgM | Collagen III |
| Collagen X | IgG | Collagen X |
| EXOSC5 | IgM | Exosome component 5 |
| H2a | IgG, IgM | Histone H2A |
| Histone 3S calf | IgG, IgM | Histone from calf thymus Type III-S |
| Oligo 27 | IgM | GGG GGG GGG GGG GGG GT |
| Ro52 | IgG, IgM | Tripartite Motif Containing 21 (RO52) |
| Sm | IgG | smith antigen |
| SM-D3 | IgG | Small nuclear ribo-nucleoprotein D3 polypeptide |
| Thyroglobulin | IgM | Thyroglobulin from bovine thyroid |
| U1snRNP | IgG | U1 small nuclear ribonucleoprotein 70 kDa |

TABLE 21

Additional exemplary antigens against which antibody reactivity was found to be significantly different between RA patients and healthy control subjects.

| Antigen | Reactivity | Antigen details |
|---|---|---|
| B2GP 1 | IgG | B2GP1 Human Glycoprotein 1 Beta-2 Human, Glycoprotein 1, β2 |
| C1q | IgG | Complement component C1Q |
| Collagen III | IgM | Collagen III |
| Collagen X | IgG | Collagen X |
| EXOSC5 | IgM | Exosome component 5 |
| Histone 3S calf | IgM | Histone from calf thymus Type III-S |
| INFg | IgM | Interferon gamma |
| Sm | IgM | smith antigen |
| Thyroglobulin | IgM | Thyroglobulin from bovine thyroid |
| TNFa | IgG | Tumor Necrosis Factor-alpha |

TABLE 22

Additional exemplary antigens against which antibody reactivity was found to be significantly different between SLE patients and SSc patients.

| Antigen | Reactivity | Antigen details |
|---|---|---|
| C1Q | IgG | Complement component C1Q |
| DNAds | IgG | DNA double strand |
| DNAss | IgG | DNA single strand |
| H2a | IgG | Histone H2A |
| Histone 3S calf | IgG | Histone from calf thymus Type III-S |
| HSP90 | IgG | HSP90 bovine, Hsp90 Native Human Protein, |
| Laminin | IgG | Laminin |
| Oligo 1 | IgG | AAA AAA AAA AAA AAA AAA AA |
| Oligo 16 | IgG | CCA TAA TTG CAA ACG TTC TG |
| Oligo 17 | IgG | CCA TAA TTG CAA AGC TTC TG |
| Oligo 18 | IgG | TTT TTT TTT TTT TTT TTT TT |
| Oligo 20 | IgG | CCA TAA TTC GAA ACG TTC TG |
| Oligo 21 | IgG | TTA GGG TTA GGG TTA GGG TTA GGG |
| Oligo 22 | IgG | GTT TTT TTT TTT TTT TTG |
| Oligo 28 | IgG, IgM | GGG GGG G |

TABLE 22-continued

Additional exemplary antigens against which antibody reactivity was found to be significantly different between SLE patients and SSc patients.

| Antigen | Reactivity | Antigen details |
|---|---|---|
| Oligo 29 | IgG | GGG GGG GGG |
| Oligo 7 | IgG | GAG AGA GAG AGA GAG AGA GA |
| PARP1 | IgG | Poly (ADP-Ribose) Polymerase 1 Human |
| Sm | IgG | smith antigen |
| Sm-D3 | IgG | Small nuclear ribonucleo-protein D3 polypeptide |
| U1snRNP | IgG | U1 small nuclear ribo-nucleoprotein 70 kDa |

TABLE 23

Additional exemplary antigen against which antibody reactivity was found to be significantly different between SLE patients and APS patients.

| Antigen | Reactivity | Antigen details |
|---|---|---|
| Oligo 22 | IgG | GTT TTT TTT TTT TTT TTG |

TABLE 24

Additional exemplary antigen against which antibody reactivity was found to be significantly different between SLE patients and SS patients.

| Antigen | Reactivity | Antigen details |
|---|---|---|
| Sm | IgG | smith antigen |

TABLE 25

Additional exemplary antigens against which antibody reactivity was found to be significantly different between SLE patients and RA patients.

| Antigen | Reactivity | Antigen details |
|---|---|---|
| C1q | IgM | Complement component C1Q |
| Collagen X | IgG | Collagen X |
| DNAds | IgG | DNA double strand |
| DNAss | IgG | DNA single strand |
| H2a | IgG | Histone H2A |
| Histone 3S calf | IgG | Histone from calf thymus Type III-S |
| HSP90 | IgG | HSP90 bovine, Hsp90 Native Human Protein, |
| Laminin | IgG | Laminin |
| Oligo 1 | IgG | AAA AAA AAA AAA AAA AAA AA |
| Oligo 16 | IgG | CCA TAA TTG CAA ACG TTC TG |
| Oligo 17 | IgG | CCA TAA TTG CAA AGC TTC TG |
| Oligo 19 | IgG | TTG GGG GGG GGG GGG GGG TT |
| Oligo 20 | IgG | CCA TAA TTC GAA ACG TTC TG |
| Oligo 21 | IgG | TTA GGG TTA GGG TTA GGG TTA GGG |
| Oligo 22 | IgG | GTT TTT TTT TTT TTT TTG |
| Oligo 26 | IgG | TTT TTT TTT TTT TTT TGG |
| Oligo 7 | IgG | GAG AGA GAG AGA GAG AGA GA |
| PARP1 | IgG | Poly (ADP-Ribose) Polymerase 1 Human |
| Sm | IgG | smith antigen |
| SM-D3 | IgG | Small nuclear ribonucleo-protein D3 polypeptide |
| U1snRNP | IgG | U1 small nuclear ribo-nucleoprotein 70 kDa |

TABLE 26

Additional exemplary antigens against which antibody reactivity was found to be significantly different between SSc patients and SS patients.

| Antigen | Reactivity | Antigen details |
|---|---|---|
| Collagen X | IgG | Collagen X |
| H2a | IgG | Histone H2A |
| Histone 3S calf | IgG | Histone from calf thymus Type III-S |
| Ro52 | IgG | Tripartite Motif Containing 21 (RO52) |
| SM-D3 | IgG | Small nuclear ribonucleoprotein D3 polypeptide |
| U1snRNP | IgG | U1 small nuclear ribonucleoprotein 70 kDa |

TABLE 27

Additional exemplary antigen against which antibody reactivity was found to be significantly different between APS patients and SS patients.

| Antigen | Reactivity | Antigen details |
|---|---|---|
| Ro52 | IgG | Tripartite Motif Containing 21 (R052) |

TABLE 28

Additional exemplary antigens against which antibody reactivity was found to be significantly different between SS patients and RA patients.

| Antigen | Reactivity | Antigen details |
|---|---|---|
| Collagen X | IgG | Collagen X |
| H2a | IgG | Histone H2A |
| Histone 3S calf | IgG | Histone from calf thymus Type III-S |
| Microglobulin-b2 | IgG | microglobulin beta2, monocyte chemoattractant protein |
| Ro52 | IgG | Tripartite Motif Containing 21 (RO52) |
| SM-D3 | IgG | Small nuclear ribonucleoprotein D3 polypeptide |
| Sm | IgG | smith antigen |

Table 29 lists the sequences of the oligonucleotide antigens presented in Table 15.

TABLE 29

Sequences of oligonucleotide antigens

| Oligo-nucleotide | SEQ ID NO | Sequence |
|---|---|---|
| Oligo1 | 1 | AAA AAA AAA AAA AAA AAA AA |
| Oligo10 | 2 | GGG GGG GGG GGG GGG GG |
| Oligo11 | 3 | GGG GGG GGG GGG GGG GGG GG |
| Oligo16 | 4 | CCA TAA TTG CAA ACG TTC TG |
| Oligo17 | 5 | CCA TAA TTG CAA AGC TTC TG |
| Oligo18 | 6 | TTT TTT TTT TTT TTT TTT TT |
| Oligo19 | 7 | TTG GGG GGG GGG GGG GGG TT |
| Oligo20 | 8 | CCA TAA TTC GAA ACG TTC TG |
| Oligo21 | 9 | TTA GGG TTA GGG TTA GGG TTA GGG |
| Oligo22 | 10 | GTT TTT TTT TTT TTT TTG |
| Oligo23 | 11 | GTT TTT TTT TTT TTT TT |
| Oligo24 | 12 | TTT TTT TTT TTT TTT TG |
| Oligo26 | 13 | TTT TTT TTT TTT TTT TGG |
| Oligo27 | 14 | GGG GGG GGG GGG GGG GT |
| Oligo28 | 15 | GGG GGG G |
| Oligo29 | 16 | GGG GGG GGG |
| Oligo30 | 17 | TGG GGG GGG GGG GGG GG |
| Oligo4 | 18 | CCC CCC CCC CCC CCC CCC CC |
| Oligo5 | 19 | CGC GCG CGC GCG CGC GCG CG |
| Oligo7 | 20 | GAG AGA GAG AGA GAG AGA GA |
| Oligo8 | 21 | GTG TGT GTG TGT GTG TGT GT |
| Oligo9 | 22 | GGG GGG GGG GGG GG |

Example 3

In a separate experiment, performed as described in Example 1 on 55 HC subjects, 30 SLE patients, 19 RA patients, and 20 SSc patients, the following groups were compared:

HC (N=55) vs all autoimmune rheumatic diseases patients (AI), including SSc, RA, and SLE (N=69); SLE vs RA; SLE vs SSc; SSc vs RA; and SLE vs HC.

The results are presented in Tables 30-34, which list the antigens found to be effective in distinguishing between the test groups, along with their antibody reactivities and FDR corrected t-test p values for the comparisons.

As can be seen from Tables 30-34 several antigens were identified with IgG and/or IgM reactivities that could significantly distinguish between the groups compared.

TABLE 30

Exemplary antigens against which antibody reactivity was found to be significantly different between autoimmune rheumatic diseased patients (SLE, SSc, and RA) and healthy control subjects (HC).

| Antigen | Reactivity | AI N69 vs HC N55 Corrected Ttest p | Antigen details |
|---|---|---|---|
| AITRL-Pepro | IgM | 6.79E-03 | Tumor necrosis factor ligand superfamily member 18 |
| ANXA1 | IgM | 3.82E-03 | Annexin A1 |
| B2GP1 | IgG | 9.98E-03 | B2GP1 Human Glycoprotein 1 |
| C1q | IgG | 1.24E-03 | Complement component C1Q |
| C3b-Native | IgG | 8.93E-03 | Complement C3b protein |

TABLE 30-continued

Exemplary antigens against which antibody reactivity was found to be significantly different between autoimmune rheumatic diseased patients (SLE, SSc, and RA) and healthy control subjects (HC).

| Antigen | Reactivity | AI N69 vs HC N55 Corrected Ttest p | Antigen details |
| --- | --- | --- | --- |
| Cardiolipin | IgM | 8.93E-03 | Cardiolipin |
| CD46 | IgG | 8.93E-03 | Membrane cofactor protein |
| CD62P | IgG | 4.44E-03 | P-Selectin/CD62P |
| CENPB | IgG | 8.93E-03 | Centromere Protein-B, rh |
| Chromatin | IgG | 7.62E-03 | chromatin |
| CollagenX | IgG | 1.24E-03 | CollagenX |
| CXCL2 | IgM | 1.36E-03 | C-X-C motif chemokine ligand 2 |
| DDX21 | IgG | 2.16E-03 | Nucleolar RNA helicase 2 |
| DNAdsCalf | IgG | 3.82E-03 | DNA double strand |
| DNAssCalf | IgG | 3.40E-03 | DNA single strand |
| EIF4E$^{p855-1205}$ | IgG | 9.79E-03 | Eukaryotic translation initiation factor 4E |
| Entactin | IgG | 7.18E-03 | Entactin/Nidogen |
| FactorP | IgG | 1.24E-03 | Complement Factor P (Properdin) |
| Ferritin | IgG | 4.44E-03 | Ferritin |
| FGFb | IgM | 8.57E-03 | Fibroblast Growth Factor-basic rh |
| Fibrillarin | IgG | 1.19E-03 | Fibrillarin |
| GangliosideGD3 | IgM | 8.93E-03 | Disialoganglioside GD3 |
| GSTP1 | IgM | 1.88E-03 | glutathione S-transferase pi 1 |
| H1N1 | IgM | 1.24E-03 | Influenza A (H1N1) Antigen |
| HNRNPC | IgM | 8.06E-03 | Heterogeneous nuclear ribonucleoproteins C1/C2 |
| HSP27 | IgM | 6.02E-03 | Heat shock protein 27 |
| HTLVcore | IgG | 7.18E-03 | human T-cell lymphotropic virus (HTLV) core |
| ICOS | IgM | 9.32E-03 | inducible T-cell co-stimulator |
| IFN-γ | IgM | 1.19E-03 | Interferon gamma |
| IL-12 | IgM | 1.24E-03 | Interleukin 12 |
| IL-18 | IgM | 1.19E-03 | Interferon gamma |
| IL-18 | IgG | 8.93E-03 | Disialoganglioside GD3 |
| IMP2 | IgM | 4.44E-03 | Insulin-like growth factor 2 mRNA-binding protein 2 |
| LAIR1 | IgG | 1.65E-05 | Leukocyte-associated immunoglobulin-like receptor 1 |
| LDH2 | IgM | 1.57E-03 | Lactate Dehydrogenase 2 |
| LeptintA | IgM | 3.58E-03 | Leptin Antagonist Triple |
| MICA | IgM | 2.13E-03 | MHC class I polypeptide-related sequence A |
| MMP1 | IgG | 9.45E-03 | Matrix Metalloproteinase-1 |

TABLE 30-continued

Exemplary antigens against which antibody reactivity was found to be significantly different between autoimmune rheumatic diseased patients (SLE, SSc, and RA) and healthy control subjects (HC).

| Antigen | Reactivity | AI N69 vs HC N55 Corrected Ttest p | Antigen details |
| --- | --- | --- | --- |
| NGFb | IgG | 7.97E-03 | Nerve Growth Factor-beta |
| oligo10 | IgG | 8.58E-03 | GGG GGG GGG GGG GGG GG |
| oligo11 | IgG | 6.79E-03 | GGG GGG GGG GGG GGG GGG GG |
| oligo27 | IgG | 7.62E-03 | GGG GGG GGG GGG GGG GT |
| oligo29 | IgG | 5.42E-03 | GGG GGG GGG |
| OVA | IgG | 1.19E-03 | Ovalbumin |
| PARP1 | IgG | 8.93E-03 | Poly (ADP-Ribose) Polymerase 1 Human |
| RO52 | IgG | 1.24E-03 | Tripartite Motif Containing 21 (RO52) |
| Ro52 | IgG | 8.93E-03 | Tripartite Motif Containing 21 (RO52) |
| RO60calf | IgG | 2.18E-03 | TROVE Domain Family Member 2 |
| RPP0 | IgG | 7.18E-03 | Ribosomal Phosphoprotein P0 |
| SNRPB | IgG | 8.57E-03 | small nuclear ribonucleoprotein polypeptides B and B1 |
| TgondiiROP4 | IgM | 3.07E-03 | Toxoplasma Gondii ROP4 (RH2) Mosaic |
| TPM2 | IgG | 5.42E-03 | tropomyosin beta chain |

TABLE 31

Additional exemplary antigens against which antibody reactivity was found to be significantly different between SLE patients and RA patients

| Antigen | Reactivity | AI N69 vs HC N55 Corrected Ttest p | Antigen details |
| --- | --- | --- | --- |
| BCMO1 | IgG | 5.37E-03 | beta-carotene oxygenase 1 |
| C1r | IgG | 3.25E-02 | Complement component C1R |
| C1s | IgG | 5.37E-03 | Complement component C1s |
| CD46 | IgG | 3.25E-02 | Membrane cofactor protein |
| DLST | IgG | 3.14E-05 | 2-oxoglutarate dehydrogenase complex component E2 |
| FactorBa | IgG | 3.64E-02 | Ba fragment of factor B |
| GM2M | IgG | 3.25E-02 | Monosialoganglioside GM2 bovine brain |
| H1 | IgG | 3.25E-02 | Histone H1 |
| HSV1 | IgM | 4.40E-02 | Herpes Simplex Virus-1 |
| HSV1gG | IgG | 3.25E-02 | Herpes Simplex Virus (HSV)-1 gG |
| HSV1gG | IgM | 3.25E-02 | Herpes Simplex Virus (HSV)-1 gG |
| RNPsm | IgG | 1.14E-02 | RNP-Sm complex |
| RNPsm | IgM | 1.14E-02 | RNP-Sm complex |
| RO60calf | IgG | 1.56E-02 | TROVE Domain Family Member 2 |
| RPP0 | IgG | 3.92E-02 | Ba fragment of factor B |
| SC5b9 | IgG | 4.40E-02 | Serum Complement Membrane Attack Complex |
| Sm | IgG | 3.64E-02 | smith antigen |

TABLE 32

Additional exemplary antigens against which antibody reactivity was found to be significantly different between SLE patients and SSc patients

| Antigen (IgG reactivity) | SLE N30 vs SSc N20 Corrected Ttest p | Antigen details |
|---|---|---|
| CD23 | 4.19E-02 | Fc epsilon RII |
| CENPB | 1.74E-02 | Centromere Protein-B, rh |
| DT | 1.83E-02 | Diphtheria Toxin from *Corynebacterium diphtheriae* |
| RO60calf | 1.83E-02 | TROVE Domain Family Member 2 |

TABLE 33

Additional exemplary antigen against which antibody reactivity was found to be significantly different between SSc patients and RA patients

| Antigen (IgG reactivity) | SSC N20 vs RA N19 Corrected Ttest p | Antigen details |
|---|---|---|
| CENPB | 2.14E-02 | Centromere Protein-B, rh |

TABLE 34

Additional exemplary antigens against which antibody reactivity was found to be significantly different between SLE patients and HC subjects

| Antigen | Reactivity | SLE N30 vs HC N55 Corrected Ttest p | Antigen details |
|---|---|---|---|
| CCR2 | IgM | 8.41E-04 | Chemokine (C-C motif) receptor 2 |
| CD46 | IgG | 2.08E-05 | Membrane cofactor protein |
| Chromatin | IgG | 5.15E-05 | chromatin |
| DLST | IgG | 9.43E-04 | 2-oxoglutarate dehydrogenase complex component E2 |
| FactorII | IgM | 7.06E-04 | Clotting Factor II, hum prothrombin |
| Fibrillarin | IgG | 5.61E-04 | Fibrillarin |
| H1 | IgG | 5.74E-05 | Histone H1 |
| IL-12 | IgM | 2.33E-04 | Interleukin 12 |
| IL-18 | IgM | 2.33E-04 | Interleukin 18 |
| IMP2 | IgM | 7.06E-04 | Insulin-like growth factor 2 mRNA-binding protein 2 |
| LDH2 | IgM | 6.83E-04 | Lactate Dehydrogenase 2 |
| MICA | IgM | 6.35E-04 | MHC class I polypeptide-related sequence A |
| oligo11 | IgG | 7.06E-04 | GGG GGG GGG GGG GGG GGG GG |
| oligo29 | IgG | 1.81E-04 | GGG GGG GGG |
| RNPsm | IgG | 6.84E-04 | RNP-Sm complex |
| RNPsm | IgM | 6.35E-04 | RNP-Sm complex |
| Ro52 | IgG | 9.78E-04 | Tripartite Motif Containing 21 (RO52) |
| RO60calf | IgG | 5.82E-10 | TROVE Domain Family Member 2 |
| RPP0 | IgG | 8.69E-06 | Lactate Dehydrogenase 2 |
| SNRPA | IgG | 2.33E-04 | U1 small nuclear ribonucleoprotein A |
| SNRPB | IgG | 2.08E-05 | small nuclear ribonucleoprotein polypeptides B and B1 |
| SNRPC | IgG | 1.71E-04 | U1 small nuclear ribonucleoprotein C |
| U1snRNP | IgG | 9.43E-04 | U1 small nuclear ribonucleoprotein 70 kDa |

Thus, the results presented herein demonstrate that classifiers comparing the reactivity patterns of the subjects to a plurality of antigens as set forth in any one of Tables 1-12, 16-28 and 30-34, using supervised classification algorithms, would be highly effective in differential diagnosis as disclosed herein.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

---

The invention claimed is:

1. A method for differential diagnosing and treating an autoimmune rheumatic disease selected from the group consisting of systemic lupus erythematosus (SLE), rheumatoid arthritis (RA), scleroderma (SSc), Sjogren's Syndrome (SS), and anti-phospholipid syndrome (APS) in a subject, the method comprising:
  i. obtaining a sample from a subject suspected of having an autoimmune rheumatic disease due to inflammation and at least one rheumatic symptom selected from the group consisting of: joint pain, joint stiffness, joint swelling, joint redness, joint tenderness, joint warmth, and loss of joint range of motion;
  ii. determining the reactivity of antibodies in the sample obtained from the subject to a plurality of antigens, thereby obtaining a reactivity pattern of said sample to the plurality of antigens, wherein said plurality of antigens consisting of: Bactericidal permeability-increasing protein (BPI), Complement Component C1s (C1s), Complement Component C4 (C4), Complement Component C4c (C4c), Cancer Antigen 125 (CA125), TNF receptor superfamily member 9 (CD137), P-Selectin (CD62P), Centromere Protein-B (CENPB), Chromodomain helicase DNA binding protein 4 (CHD4), Chromatin, collagen II, Cytotoxic T-Lymphocyte Associated Antigen-4/Fc Chimera (CTLA4), Diphtheria Toxin from *Corynebacterium diphtheriae* (DT), Erythropoietin (EPO), Esterase-D (ESD), Exosome component 10 (EXOSC10), Ferritin, formyl peptide receptor 1 (FPR1), fascin homolog 1, actin-bundling protein (FSCN1), Histone H1 (H1), Histone H3 (H3), *Homo sapiens* major histocompatibility complex, class I, B (HLAB), Major Histocompatibility Complex Class I-C (HLAC), Interleukin 35 (IL35), Leukocyte-associated immunoglobulin-like receptor 1 (LAIR1), Leptin Antagonist Triple (Leptin A), MHC class I polypeptide-related sequence A (MICA), myxovirus resistance 1, interferon-inducible protein p78 (MX1), Myosin heavy chain 1 (MYH1), Nucleosome Assembly Protein 1-Like 1 (NAP1L1), TROVE Domain Family Member 2 (RO60), Tissue Transglutaminase (TGM2), *Toxoplasma Gondii* p24 (TgondiiP24), thrombospondin 1 (THBS1), tyrosine kinase 2 (Tyk2), and Chitinase-3-like protein (YLK40);
  iii. comparing the reactivity pattern of said sample to a healthy control reactivity pattern to said plurality of antigens by a supervised classification algorithm, wherein a significantly different reactivity pattern of the sample obtained from the subject compared to the healthy control reactivity pattern indicates that said subject has the autoimmune rheumatic disease, and
  iv. treating said subject diagnosed as having the autoimmune rheumatic disease with a disease-specific treatment selected from the group consisting of nonsteroidial anti-inflammatory drugs (NSAIDs), corticosteroids, glucocorticoids, immunosuppressants, hydroxychloroquine, cyclophosphamide, TNF-α inhibitors, chelating agents, endothelin receptor antagonist, PAH, PDE-5 inhibitors, gastrointestinal agents, immunomodulators, analgesics, anticoagulants, antiplatelet and other biologic medications,
wherein the method further comprises identifying the autoimmune disease in said subject by the steps comprising:
  a. determining the reactivity of antibodies in the sample obtained from the subject to a second plurality of antigens, thereby obtaining a reactivity pattern of said sample to the second plurality of antigens;
  b. comparing the reactivity pattern of said sample to a healthy control reactivity pattern to said second plurality of antigens, by a supervised classification algorithm,
  wherein:
    said second plurality of antigens is selected from the group consisting of: APEX Nuclease-1 (APEX), B-lymphocyte antigen B7-2 (B7-2), V-Set Domain Containing T Cell Activation Inhibitor 1 (B7H4), 2-Oxo-Acid Dehydrogenase Complex E2 (BCOADC-E2), Brain-Derived Neurotrophic Factor (BDNF), Bone Morphogenetic protein-7 (BMP7), bone marrow stromal antigen 2 (BST2), C1s, Complement component C2 (C2), Complement component C3b (C3b), Complement component C3c (C3c), CD3 epsilon Protein (CD3e), Membrane cofactor protein (CD46), CD62P, B-lymphocyte Activation Antigen B7-1 Protein (CD80), CTLA4, chromatin, collagen II, 2-oxoglutarate dehydrogenase complex component E2 (DLST), Complement Factor P (Factor P), H1, Human Histone cluster 2 H2BE (H2BQ), Histone H2B (H2B), Histone H4 (H4), Interferon-alpha 2 (IFNa2), Interleukin-4 (IL4), LAIR1, Tumor Necrosis Factor Ligand Superfamily Member 14 (LIGHT), MICA, Mitochondrial Antigen-Pyruvate dehydrogenase complex (MitoAg), NFkB, Tumor necrosis factor receptor superfamily member 4 (OX40), RANTES, RNP-Sm complex (RNPsm), RO60, 60S acidic ribosomal protein P1 (RPLP1), 60S acidic ribosomal protein P2 (RPLP2), Ribosomal Phosphoprotein P0 (RPPO), Ribosomal P Antigen (RibosomalP), CENPB, HSV2, *Toxoplasma Gondii* p24 (Tgondii24), Chitinase-3-like protein 1 (YLK), Serum Amyloid P (SAP), Stromal Cell-Derived Factor-1 alpha (SDF1a), U1 small nuclear ribonucleoprotein A (SNRPA), small nuclear ribonucleoprotein polypeptides B and B1 (SNRPB), U1 small nuclear ribonucleoprotein C (SNRPC), Nuclear autoantigen Sp-100 (SP100), Alpha II-spectrin (SPTAN1), syndecan 1 (SYND1), Small nuclear ribonucleoprotein D1 (Sm-D1), Small nuclear ribonucleoprotein D1/D2/D3 (SmD), TGM2, Tumor Necrosis Factor-beta (TNFb), TNF-Related Apoptosis Inducing Ligand/Apo2L (TRAIL), X-ray repair complementing defective repair in Chinese hamster cells 5 (XRcc5), Oxidized low-density lipoprotein (oxLDL), Poly ADP Ribose Polymer-PAR (pADPr), and a significantly different reactivity pattern of the sample obtained from the subject to said second plurality of antigens compared to the healthy control reactivity pattern indicates that said subject has SLE;
    said second plurality of antigens is selected from the group consisting of: Activating Transcription Factor 2 (ATF2), BPI, CA125, Integrin subunit beta 1 (CD29), platelet/endothelial cell adhesion molecule CD31 (CD31), T-cell surface glycoprotein CD8 alpha chain (CD8A), Alpha-crystallin B chain (CRYAB), Catalase, collagen II, DT, ESD, FPR1, Ferritin, H2BQ, H3, HLAB, HLAC, Haptoglobin 2-2, IL4, Ki67, LAIR1, Leptin A, Mannan-binding lectin serine protease 2 (MASP2), MX1, MYH1, Neurofilament 68, RibosomalP, CENPB, EXOSC10, Tgondii24, YLK40, C1 esterase inhibitor (SerpinG1), TGM2, THBS1, Tyk2, oxLDL and a significantly different reactivity pattern of the sample obtained from the subject to said second plurality of antigens-compared to the healthy control reactivity pattern indicates that said subject has SSc;
    said second plurality of antigens is selected from the group consisting of: beta-carotene oxygenase 1 (BCM01$^{p6-206}$), BPI, Chromatin, Ferritin, H1, HLAC, LAIR1, MYH1, Sm-D1, SmD, TGM2, and Tyk2 and a significantly different reactivity pattern of the sample obtained from the subject to said second plurality of antigens compared to the healthy control reactivity pattern indicates that said subject has APS;
    said second plurality of antigens is selected from the group consisting of: APEX, C2, Tumor Necrosis Factor ligand Superfamily Member 9 (CD137L), CRYAB, C-X-C motif chemokine ligand 2 (CXCL2), Chromatin, Collagen XVIII$^{1154-1335}$ (Endostatin P1), H1, H2B, H4, Interleukin-3 (IL3), LAIR1, Ia-like antigen, LA/SS-B (La), Macrophage Inflammatory Protein-1 beta (MIP1b), Tumor necrosis factor ligand superfamily member 4 (OX40L), RO60, C4c, EXOSC10, Exosome component 9 (EXOSC9), Tgondii24, SDF1a, SNRPB, Sm-D1, and SmD, and a significantly different reactivity pattern of the sample obtained from the subject to said second plurality of antigens compared to the healthy control reactivity pattern indicates that said subject has SS; and/or
    said second plurality of antigens is selected from the group consisting of: ATF2, BPI, C4c, CA125, CD137, CD29, collagen II, CRYAB, DT, Entactin, EPO, ESD, EXOSC10, Ferritin, FPR1, glutathione S-transferase (GSTP1), H2BQ, H3, HLAB, HLAC, Lymphocyte activation gene 3 protein (LAG3), LAIR1, Leptin A, LIGHT, MASP2, Chromodomain-helicase-DNA-binding protein Mi-2 homolog (Mi-2), MX1, MYH1, NAP1L1, Neurofilament68, Neutrophil Gelatinase Associated (NGAL), Nuclear receptor-binding factor 2 (NRBF2), RibosomalP, STAT1, signal transducer and activator of transcription 4 (STAT4), STATE, THBS1, Tyk2, and YLK40, and a significantly different reactivity pattern of the sample obtained from the subject to said second plurality of antigens-compared to the healthy control reactivity pattern indicates that said subject has RA.

2. The method of claim 1, wherein said disease is RA and said disease-specific treatment is selected from the group consisting of Etanercept, Adalimumab, Infliximab, Certolizumab pegol, Golimumab, Anakinra, Tocilizumab, Tofacitinib, and any combination thereof.

3. The method of claim 1, wherein said disease is SS and said disease-specific treatment is selected from the group consisting of pilocarpine, cevimeline, cyclosporine, and any combination thereof.

4. The method of claim 1, wherein said disease is SLE and said disease-specific treatment is selected from the group consisting of NSAIDs, Ibuprofen, Naproxen, Prednisone, Methylprednisolone, Cellcept, Methotrexate, Imuran, mycophenolate mofetil, Abatacept, Arava, Immune globulin intravenous, Plaquenil, Myfortic, Endoxan, Cytoxan, Neosar, Procytox, Revimmune, Benilimumab, Rituximab, Cyclosporine.

5. The method of claim 1, wherein said disease is APS and said disease-specific treatment is selected from the group consisting of warfarin, rivaroxaban, dabigatran, apixaban, edoxaban, heparin, aspirin, clopidogrel, Rituximab.

6. The method of claim 1, wherein said disease is SSc and said disease-specific treatment is selected from the group consisting of Ibuprofen, Naproxen, Prednisone, Cellcept, Methotrexate, Imuran, Cytoxan, Rituximab, Penicillamine, Bosentan, Ambrisentan, Macitentan, Tadalafil, Sildenafil.

7. The method according to claim 1, wherein the sample is selected from the group consisting of a serum sample, a plasma sample, and a blood sample, and the reactivity of antibodies comprises IgM reactivity, IgG reactivity, or a combination thereof.

8. The method according to claim 1, wherein the supervised classification algorithm is selected from the group consisting of Support Vector Machine (SVM), Quadratic Discriminant Analysis (QDA), and Nave Bayesian Classifier (NB).

9. The method according to claim 1, wherein the reactivity of the antibodies to the plurality of antigens in the sample obtained from a control subject is selected from the group consisting of reactivity of antibodies in multiple samples of control subjects, and a stored set of data from control subjects, and wherein the antigens are in the form of an antigen probe set, an antigen array, or an antigen chip.

* * * * *